(12) United States Patent
Yue et al.

(10) Patent No.: US 6,333,338 B1
(45) Date of Patent: Dec. 25, 2001

(54) BISPIPERIDINES AS ANTITHROMBOTIC AGENTS

(75) Inventors: Christophe Yue; Marguerite Henry, both of Maisons Alfort; Thierry Giboulot, Vincennes; Brigitte Lesur, Champs-sur-Marne, all of (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/743,910
(22) PCT Filed: Jul. 16, 1999
(86) PCT No.: PCT/FR99/01745
§ 371 Date: Jan. 17, 2001
§ 102(e) Date: Jan. 17, 2001
(87) PCT Pub. No.: WO00/03986
PCT Pub. Date: Jan. 27, 2000

(30) Foreign Application Priority Data

Jul. 17, 1998 (FR) .................................................. 98 09166

(51) Int. Cl.$^7$ ...................... A61K 31/4545; C07D 401/06
(52) U.S. Cl. ........................... 514/316; 546/190; 546/189; 546/187; 546/186
(58) Field of Search ........................... 514/316; 546/190, 546/189, 187, 186

(56) References Cited

FOREIGN PATENT DOCUMENTS 0 478 362  4/1992  (EP) .

OTHER PUBLICATIONS

M. E. Duggan et al., "Non–Peptide Fibrinogen Receptor Antagonists 7 Design and Syntesis of A Potent, Orally Active Fibrinogen Receptr Antagonist", *Journal of Medicinal Chemistry*, 1995, vol. 38, No. 17, pp. 3332–3341.

*Primary Examiner*—Charanjit S. Aulakh
(74) *Attorney, Agent, or Firm*—Young & Thompson

(57) ABSTRACT

Novel compounds which are inhibitors of the binding of fibrinogen to the Gp IIb/IIIa platelet receptors, and which can be used therepeutically as antithrombotic agents

14 Claims, No Drawings

BISPIPERIDINES AS ANTITHROMBOTIC AGENTS

The present invention relates to novel compounds which are inhibitors of the binding of fibrinogen to the Gp IIb/IIIa platelet receptors, and which can be used therapeutically as antithrombotic agents.

In the course of the pathological processes which lead to the formation of a thrombus (clot) and then to its extension, platelet aggregation represents a key step since it is the source of the seriousness of the phenomenon. Specifically, from the initiation of the thrombus, in particular in the arterial blood circulation, the intervention of several interdependent biochemical reactions induces the aggregation of an increasingly large number of platelets via the conversion of soluble fibrinogen into insoluble fibrin filaments which increase the size of the mass of platelets, first at the actual site of the arterial vascular lesion, and then increasingly in the lumen of the vessel.

In this mechanism of platelet aggregation, activation of the Gp IIb/IIIa receptors is the source of the amplification of the platelet aggregation. Fibrinogen, which can bind via its two dimers to these receptors, amplifies the binding-together of the platelets and thus induces the formation of a platelet mass forming a thrombus at the site of rupture of the atheroma plaque.

This mechanism of platelet aggregation is particularly active in all arterial thromboses, whether they appear in the course of performing interventional cardiology (transluminal percutaneous angioplasty; insertion of stents), heart surgery (aorto-coronary bypass; valve surgery), in the course of acute heart diseases (myocardial infarction, unstable angina, acute coronary syndromes, etc.) or in the course of certain cerebral ischaemias, or finally in the course of myocardial ischaemias which may complicate the follow-up of an antithrombotic treatment.

Reducing or preventing the activation of platelets in contact with a broken atherosclerotic plaque thus represents a novel and effective therapeutic approach to the treatment of thrombosis, in particular arterial thrombosis, and thus an efficient means for preventing acute coronary syndromes, including unstable angina and myocardial infarction.

The present invention is directed towards providing novel competitive inhibitors of the binding of fibrinogen to the Gp IIb/IIIa receptors.

The present invention is also directed towards providing compounds which can be administered orally, thus allowing a prolonged duration of action to be obtained and avoiding the risks of bleeding.

One subject of the present invention is compounds of general formula (I):

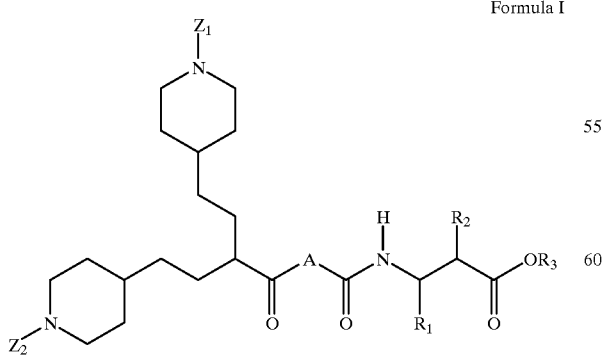

Formula I in which
i) either $R_1$ is selected from:

$C_1$–$C_4$ alkyl, $C_3$–$C_{12}$ mono- or bicyclic cycloalkyl, $C_2$–$C_4$ alkenyl or $C_2$–$C_4$ alkynyl groups, these groups optionally being substituted with groups selected from halogens and the hydroxyl group;

mono-, bi- or tricyclic $C_6$–$C_{14}$ aryl groups, heteroaryl groups selected from pyridyl, thienyl, furyl, quinolyl, benzodioxanyl, benzodioxolyl, benzothienyl, benzofuryl and pyrazinyl groups;

phenyl($C_1$–$C_4$)alkyl and naphthyl ($C_1$–$C_4$)alkyl groups optionally substituted on the aryl nucleus, the aryl and heteroaryl groups possibly being substituted with one or more groups selected independently from halogens, $C_1$–$C_4$ alkyl, trifluoromethyl, $C_1$–$C_4$ alkylthio, $C_1$–$C_4$ alkylsulphonyl, $C_1$–$C_4$ alkyloxy, nitro, and groups —COOR, —CH$_2$COOR or —O— CH$_2$—COOR, R being a $C_1$–$C_4$ alkyl group, the groups of formula:

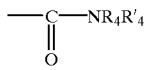

in which $R_4$ and $R'_4$ are selected from $C_1$–$C_8$ alkyl and mono- or polycyclic $C_3$–$C_2$ cycloalkyl groups, these groups optionally being substituted with groups selected from halogens and the hydroxyl group, $R'_4$ also possibly being hydrogen, or alternatively $R_4$ and $R'_4$ together form a tetramethylene or pentamethylene group, these last two groups themselves possibly being substituted, in particular with a $C_6$–$C_{14}$ aryl or $(C_6$–$C_{14})$ aryl($C_1$–$C_4$)alkyl residue;

the groups of formula:

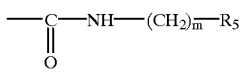

in which m=1 to 4 and $R_5$ is selected from phenyl, methoxyphenyl, indolyl, benzodioxolyl, benzodioxanyl, benzothienyl and benzofuryl groups, and $R_2$ is hydrogen, ii) or $R_1$ is hydrogen and $R_2$ is selected from the groups of formula:

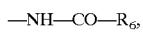

—NH—CO—R$_6$, $R_6$ being selected from $C_1$–$C_4$ alkoxy, $C_3$–$C_7$ cycloalkoxy, benzyloxy, methoxyphenyl, dimethoxyphenyl, benzodioxolyl and benzodioxanyl groups, and the groups of formula:

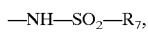

—NH—SO$_2$—R$_7$, $R_7$ being selected from:
$C_1$–$C_5$ alkyl groups optionally substituted with one or more groups selected from halogens, hydroxyl groups and the trifluoromethyl group;
$C_2$–$C_5$ alkenyl groups;
mono- or bicyclic $C_3$–$C_{12}$ cycloalkyl groups;
mono-, bi- or tricyclic $C_6$–$C_{14}$ aryl groups;

heteroaryl groups selected from pyridyl, furyl, thienyl, quinolyl, benzodioxanyl, benzodioxolyl, isoxazolyl, benzodioxinyl, benzothienyl, thiazolyl, pyrazolyl, benzofuryl and benzothiazolyl groups;

phenyl($C_1$–$C_4$)alkyl and naphthyl ($C_1$–$C_4$)alkyl groups;

and the groups of formula:

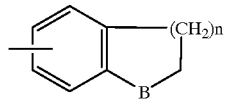

in which n=1, 2 or 3 and B is selected from —$CH_2$—, O or S and —NH—, the aryl or heteroaryl groups optionally being substituted with one or more groups selected independently from halogens, $C_1$–$C_4$ alkyl, $C_3$–$C_7$ cycloalkyl, trifluoromethyl, $C_1$–$C_4$ alkylthio, $C_1$–$C_4$ alkyloxy, $C_1$–$C_4$ alkylsulphonyl, nitro, di(($C_1$–$C_4$)alkyl)amino and groups —COOR, —$CH_2$—COOR or —O—$CH_2$COOR, R being a $C_1$–$C_4$ alkyl group, phenyl and naphthyl groups and heteroaryl groups selected from thienyl, furyl and pyridyl groups, iii) $R_3$ is selected from a hydrogen atom, a $C_1$–$C_4$ alkyl group and a phenyl($C_1$–$C_4$)alkyl group;

iv) A is selected from groups —NH—$CHR_{10}$—, —NH—$CHR_{10}$—$CH_2$— and

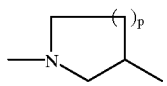

with p=1 or 2, $R_{10}$ being selected from hydrogen, a $C_1$–$C_4$ alkyl group and a $C_6$–$C_{14}$ aryl group, v) and $Z_1$ and $Z_2$ are hydrogen or an amine-protecting group, and the addition salts thereof with pharmaceutically acceptable acids.

One specific group of compounds of formula (I) is represented by the compounds of formula (Ia):

Formula Ia

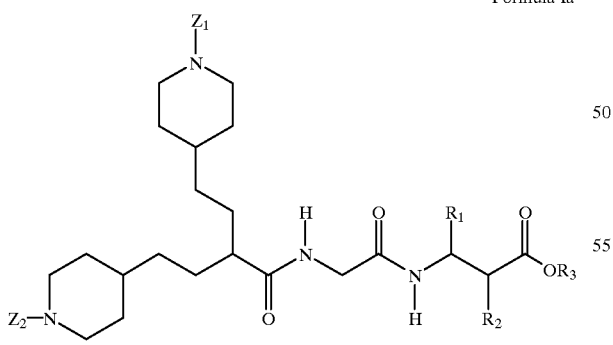

in which:

i) either $R_1$ is selected from:

$C_1$–$C_4$ alkyl, $C_3$–$C_{12}$ mono- or bicyclic cycloalkyl, $C_2$–$C_4$ alkenyl or $C_2$–$C_4$ alkynyl groups, these groups optionally being substituted with groups selected from halogens and the hydroxyl group;

mono-, bi- or tricyclic $C_6$–$C_{14}$ aryl groups, heteroaryl groups selected from pyridyl, thienyl, furyl, quinolyl, benzodioxanyl, benzodioxolyl, benzothienyl, benzofuryl and pyrazinyl groups;

phenyl($C_1$–$C_4$)alkyl and naphthyl($C_1$–$C_4$)alkyl groups optionally substituted on the aryl nucleus, the aryl and heteroaryl groups possibly being substituted with one or more groups selected independently from halogens, $C_1$–$C_4$ alkyl, trifluoromethyl, $C_1$–$C_4$ alkylthio, $C_1$–$C_4$ alkylsulphonyl, $C_1$–$C_4$ alkyloxy, nitro and groups —COOR, —$CH_2$COOR or —O— $CH_2$–COOR, R being a $C_1$–$C_4$ alkyl group, the groups of formula:

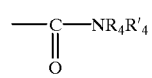

in which $R_4$ and $R'_4$ are selected from $C_1$–$C_8$ alkyl and mono- or polycyclic $C_3$–$C_{12}$ cycloalkyl groups, these groups optionally being substituted with groups selected from halogens and the hydroxyl group, $R'_4$ also possibly being hydrogen, or alternatively $R_4$ and $R'_4$ together form a tetramethylene or pentamethylene group, these last two groups themselves possibly being substituted, in particular with a $C_6$–$C_{14}$ aryl or ($C_6$–$C_{14}$)aryl($C_1$–$C_4$)alkyl residue;

the groups of formula:

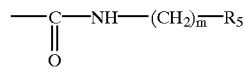

in which m=1 to 4 and $R_5$ is selected from phenyl, methoxyphenyl, indolyl, benzodioxolyl, benzodioxanyl, benzothienyl and benzofuryl groups, and $R_2$ is hydrogen, ii) or $R_1$ is hydrogen and $R_2$ is selected from the groups of formula:

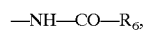

$R_6$ being selected from $C_1$–$C_4$ alkoxy, $C_3$–$C_7$ cycloalkoxy, benzyloxy, methoxyphenyl, dimethoxyphenyl, benzodioxolyl and benzodioxanyl groups, and the groups of formula:

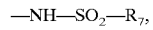

$R_7$ being selected from:

$C_1$–$C_5$ alkyl groups optionally substituted with one or more groups selected from halogens, hydroxyl groups and the trifluoromethyl group;

mono- or bicyclic $C_3$–$C_{12}$ cycloalkyl groups;

mono-, bi- or tricyclic $C_6$–$C_{14}$ aryl groups;

heteroaryl groups selected from pyridyl, thienyl, quinolyl, benzodioxanyl, benzodioxolyl and isoxazolyl groups;

phenyl ($C_1$–$C_4$)alkyl and naphthyl ($C_1$–$C_4$)alkyl groups;

and the groups of formula:

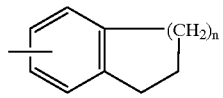

in which n=1, 2 or 3;

the aryl or heteroaryl groups optionally being substituted with one or more groups selected independently from halogens, $C_1$–$C_4$ alkyl, trifluoromethyl, $C_1$–$C_4$ alkylthio, $C_1$–$C_4$ alkyloxy, $C_1$–$C_4$ alkylsulphonyl, nitro, di(($C_1$–$C_4$)alkyl)amino and groups —COOR, —CH$_2$—COOR or —O—CH$_2$COOR, R being a $C_1$–$C_4$ alkyl group, iii) $R_3$ is selected from a hydrogen atom, a $C_1$–$C_4$ alkyl group and a phenyl($C_1$–$C_4$)alkyl group, iv) and $Z_1$ and $Z_2$ are hydrogen or an amine-protecting group, and the addition salts thereof with pharmaceutically acceptable acids.

One preferred group of compounds is represented by the compounds in which $R_1$=H and $R_2$ is a group of formula —NH—SO$_2$—$R_7$.

The compounds that are preferred most particularly are the ones of this type in which $R_7$ is a group selected from naphthyl, substituted naphthyl, biphenyl and phenylthienyl groups.

As examples of aryl groups, mention may be made of phenyl, α-naphthyl, β-naphthyl, fluorenyl and biphenyl groups.

The $C_1$–$C_5$ alkyl groups may be linear or branched. Examples which may be mentioned are methyl, ethyl, propyl, isopropyl, butyl, isobutyl, tert-Butyl and pentyl groups.

The monocyclic cycloalkyl groups may be, for example, cyclopentyl or cyclohexyl groups.

The polycyclic cycloalkyl groups may be, for example, adamantyl, norbornyl and camphoryl groups.

The alkynyl groups may be, for example, ethynyl, propargyl and butynyl groups.

The alkenyl groups may be, for example, vinyl, pentenyl and allyl groups.

The $C_1$–$C_4$ alkoxy groups may similarly be linear or branched. Examples which may be mentioned are methoxy, ethoxy, propoxy, isopropoxy, butoxy, isobutoxy and tert-butoxy groups.

The halogens may be selected from fluorine, chlorine, bromine and iodine.

The amine-protecting groups which may be mentioned are ethoxycarbonyl, benzyloxycarbonyl, p-nitrobenzyloxycarbonyl and t-butoxycarbonyl groups.

The "addition salts with pharmaceutically acceptable acids" denote salts which give the biological properties of the free bases without having an undesirable effect. These salts may be, in particular, those formed with mineral acids, such as hydrochloric acid, hydrobromic acid, sulphuric acid, nitric acid or phosphoric acid; acidic metal salts such as disodium orthophosphate and monopotassium sulphate, and organic acids.

The compounds of formula (I) can be prepared by:

a$_1$) reacting an acid of formula:

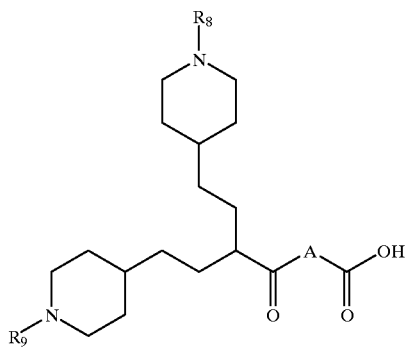

Formula II in which $R_8$ and $R_9$ are protecting groups, with an amine of formula

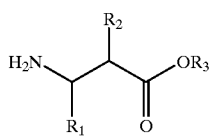

Formula III or a$_2$) reacting an acid of formula

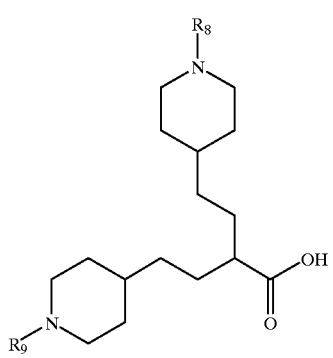

Formula IV in which $R_8$ and $R_9$ are protecting groups, with an amine of formula

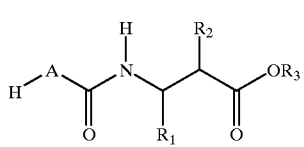

Formula V to give compounds of formula (Ib):

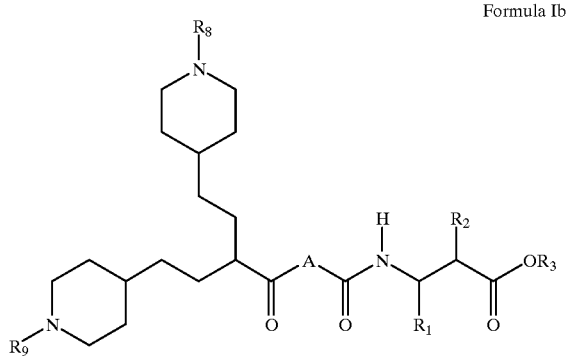

Formula Ib b) optionally, converting a group $R_2$ into another group $R_2$, c) and, optionally, removing the protecting groups.

The compounds of formula (II) can be prepared according to the reaction scheme below (when $R_8$ and $R_9$=Boc):

SCHEME 1

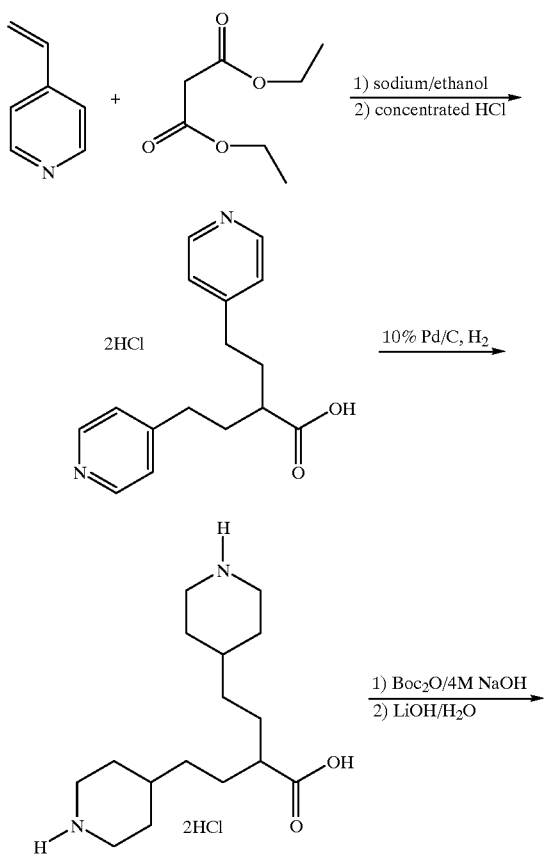

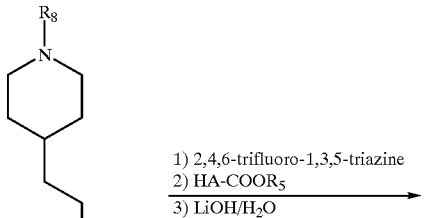

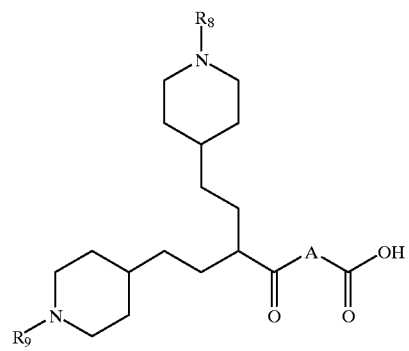

Formula II

The addition salts are obtained conventionally by reacting the compound of formula (I) with a pharmaceutically acceptable acid in a suitable solvent. Conversely, the bases can be obtained from addition salts by treatment with a strong base.

The examples which follow illustrate the preparation of the compounds of formula (I).

A—Preparation of the Acid of Formula IV

Synthesis of 4-[1-(Tert-butoxycarbonyl)-4-piperidyl]-2-{2-[1-(tert-butoxycarbonyl)-4-piperidyl]ethyl}butanoic Acid (Compound 3)

A-1 Synthesis of 4-(4-Pyridyl-2-[2-(4-pyridyl)ethyl] butanoic Acid Dihydrochloride (Compound 1)

Sodium (3.5 g, 0.15 mol) is added to a solution of 4-vinylpyridine (165 g, 1.49 mol) and diethyl malonate (120 g, 0.75 mol) in 400 ml of ethanol. The mixture is refluxed for 18 hours. Most of the ethanol is evaporated off and the residue is taken up in ether (about 300 ml) and then washed with brine. The solvent is evaporated off to give an oil, which is refluxed in 400 ml of 12 N hydrochloric acid for 12 hours. The resulting mixture is evaporated to dryness to give a red-brown oil which is taken up in about 1 l of isopropanol and left to stand at room temperature. The resulting solution is filtered, rinsed with isopropanol and acetone and dried under vacuum to give 190 g of a beige-coloured solid.

Yield=74%; Melting point=172° C.; $^1$H-NMR (400 MHz, CD$_3$OD): δ 2.1(m, 4H), 2.5 (m, 1H), 3.0 (t, 4H), 8.0 (d, 4H), 8.7 (d, 4H).

A-2 Synthesis of 4-(4-Piperidyl)-2-[2-(4-piperidyl)ethyl] butanoic Acid Dihydrochloride (Compound 2)

A mixture of 4-(4-pyridyl-2-[2-(4-pyridyl)ethyl] butanoic acid dihydrochloride (118 g, 0.344 mol) in 1.5 l of acetic acid is hydrogenated in the presence of 10% palladium-on-charcoal (10 g) under 100 psi at 60° C. for 24 hours. The mixture is filtered and evaporated to give an oil, which is slurried in ether to give a suspension. This suspension is filtered, rinsed with ether and dried to give 126 g of a beige-coloured solid.

Yield=104% (containing acetic acid); Melting point=180° C.; $^1$H-NMR (400 MHz, CD$_3$OD) δ 1.35 (m, 8H), 1.6 (m, 6H), 2.0 (bd, 4H), 2.3 (m, 1H), 3.0 (bt, 4H), 3.4 (bd, 4H).

A-3 Synthesis of 4-[1-(Tert-butoxycarbonyl)-4-piperidyl]-2-{2-[1-(tert-butoxycarbonyl)-4-piperidyl]ethyl}butanoic Acid (Compound 3)

Di-tert-Butyl dicarbonate (90 g, 0.413 mol) is added, at room temperature, to a solution of 4-(4-piperidyl)-2-[2-(4-piperidyl)ethyl]butanoic acid dihydrochloride (71.5 g, 0.203 mol) in 300 ml (1.2 mol) of 4M NaOH and 300 ml of tert-butanol. Stirring is continued for 4 hours. The organic phase is separated out and then washed with 1N HCl and water, dried over sodium sulphate and evaporated to give the crude product. Cyclohexane is added and the mixture is left to crystallize at about 0° C. The product is filtered off, rinsed with cyclohexane and dried under vacuum to give 71 g of a white solid.

Yield=73%; Melting point=162° C.; $^1$H-NMR (400 MHz, CDCl$_3$): δ 1.05 (m, 4H), 1.25 (m, 4H), 1.35 (m, 3H), 1.45 (s, 19H), 1.6 (bd, 6H), 2.25 (m, 1H), 2.88 (bt, 4H), 4.05 (bs, 4H).

B—Preparation of the Compounds of Formula II

B-1 Synthesis of 2-[(4-[1-(Tert-butoxycarbonyl)-4-piperidyl]-2-{2-[1-(tert-butoxycarbonyl)-4-piperidyl]ethyl}butanoyl)amino]acetic Acid (Compound 4)

2,4,6-Trifluoro-1,3,5-triazine (3.6 g, 26.7 mmol) are added, at room temperature, to a solution of 4-[1-(tert-butoxycarbonyl)-4-piperidyl]-2-{2-[1-(tert-butoxycarbonyl)-4-piperidyl]ethyl}butanoic acid (18.6 g, 38.6 mmol) in 150 ml of dichloromethane and pyridine (3.1 g, 39.2 mmol). After stirring for 3 hours, water is added. The organic phase is washed with water, dried over sodium sulphate and then filtered. The filtrate is used directly in the next step.

The solution is added to a mixture of methyl glycinate hydrochloride (4.9 g, 39 mmol) and diisopropylethylamine (11 g, 85.3 mmol) in 50 ml of dichloromethane. Stirring is continued at room temperature for one hour and then 1N hydrochloric acid is added. The organic phase is washed with water, dried over sodium sulphate and evaporated to give an oil, which is hydrolysed directly.

A solution of the product obtained above in 150 ml of tetrahydrofuran, 30 ml of water and lithium hydroxide monohydrate (4.2 g, 100 mmol) is stirred at room temperature for 30 minutes. The organic solvent is evaporated off and the residue is taken up in water, acidified to pH 2 and extracted with ethyl acetate. The extracts are washed with water, dried over sodium sulphate and evaporated to give 18.2 g of a white solid.

Yield=88% (for the three steps). $^1$H-NMR (400 MHz, CDCl$_3$): δ 0.95–1.65 (m, 36H), 2.04 (m, 1H), 2.65 (bt, 4H), 4.0 (bd, 6H), 6.39 (bs, 1H).

Synthesis B-1 was used for preparation of the following compounds:

B-2 3-[(4-[1-(Tert-butoxycarbonyl)-4-piperidyl]-2-{2-[1-(tert-butoxycarbonyl)- 4-piperidyl]ethyl}butanoyl)amino)propanoic Acid (Compound 5)
Starting Material: ethyl 3-aminopropanoate hydrochloride
Yield=86%.

B-3 3-[(4-[1-(Tert-butoxycarbonyl)-4-piperidyl]-2-{2-[1-(tert-butoxycarbonyl)-4-piperidyl]ethyl}butanoyl)amino]-3-methylpropanoic Acid (Compound 6)

Starting Material: ethyl 3-aminobutanoate
Yield=49%; $^1$H-NMR (400 MHz, CDCl$_3$): δ 1.03 (m, 4H), 1.15 (m, 4H), 1.25 (d, 3H), 1.35 (m, 2H), 1.45 (s, 20H), 1.63 (bd, 6H), 1.95 (m, 1H), 2.55 (dd, 2H), 2.65 (bt, 4H), 4.0 (bs, 4H), 4.35 (m, 1H), 6.25 (d, 1H).

B-4 3-[(4-[1-(Tert-butoxycarbonyl)-4-piperidyl]-2-{2-[1-(tert-butoxycarbonyl)-4-piperidyl]ethyl}butanoyl)amino]-3-phenylpropanoic Acid (Compound 7)
Starting Material: ethyl 3-amino-3-phenylpropanoate hydrochloride
Yield=68%; $^1$H-NMR (400 MHz, CDCl$_3$): δ 0.9~1.35 (m, 10H), 1.45 (s, 20H), 1.58 (m, 6H), 2.00 (m, 1H), 2.60 (bq, 4H), 2.90 (dq, 2H), 4.0 (bd, 4H), 5.45 (q, 1H), 6.78 (d, 1H), 7.25 (m, 5H).

B-5 (3R)-1-(4-[1-(Tert-butoxycarbonyl)-4-piperidyl]-2-{2-[1-(tert-butoxycarbonyl)-4-piperidyl]ethyl}butanoyl) hexahydro-3-pyridinecarboxylic Acid (Compound 8)
Starting Material: ethyl (R)-nipecotate L-tartrate
Yield=66%.

C—Preparation of the Compounds of Formula Ib

C-1 Preparation of the Compounds of Formula Ib ($R_1 \neq H$, $R_2 = H$)

1) tert-Butyl 4-{3-{[1-(1,3-Benzodioxol-5-yl)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (Compound 9)

Isobutyl chloroformate (1.5 g, 11 mmol) is added, at room temperature, to a solution of 4-[1-(tert-butoxycarbonyl)-4-piperidyl]-2-{2-[1-(tert-butoxycarbonyl)-4-piperidyl]ethyl}butanoyl)amino]acetic acid (compound 4) (5.4 g, 10 mmol) in 50 ml of ethyl acetate and N-methylmorpholine (2.2 g, 22 mmol). After stirring for 10 minutes, ethyl 3-amino-3-(1,3-benzodioxol-5-yl)propionate hydrochloride (2.8 g, 10 mmol) is added. Stirring is continued at 50° C. for 2 hours and 2N hydrochloric acid is then added. The organic phase is washed with water, dried over sodium sulphate, evaporated and purified by flash chromatography (20/1 dichloromethane/methanol) to give 6.7 g of a white solid.

Yield=88%; $^1$H-NMR (400 MHz, CDCl$_3$): δ 0.9~1.7 (m, 39H), 2.05 (m, 1H), 2.6 (bs, 4H), 2.8 (dq, 2H), 4.0 (m, 8H), 5.3 (q, 1H), 6.55 (t, 1H), 6.75 (m, 3H), 7.55 (d, 1H).

The method described above was used to prepare the following compounds:

2) tert-Butyl 4-(5-[1-(tert-Butoxycarbonyl)-4-piperidyl]-3-{[(2-{[3-ethoxy-1-(4-isopropylphenyl)-3-oxopropyl]amino}-2-oxoethyl)amino]carbonyl}pentyl)tetrahydro-1(2H)-pyridinecarboxylate (Compound 10)
Starting Material: ethyl 3-amino-3-(4-isopropyl-phenyl) propionate hydrochloride
Yield=82%; $^1$H-NMR (400 MHz, CDCl$_3$): δ 0.9~1.7 (m, 45H), 2.05 (m, 1H), 2.6 (bs, 4H), 2.8 (m, 3H), 4.0 (m, 8H), 5.4 (q, 1H), 6.5 (t, 1H), 7.15 (d, 2H), 7.2 (d, 2H), 7.45 (d, 1H).

3) Tert-Butyl 4-(5-[1-(tert-Butoxycarbonyl)-4-piperidyl]-3-{[(2-{[3-ethoxy-1-(4-methoxyphenyl)-3-oxopropyl] amino)-2-oxoethyl)amino]carbonyl}pentyl)tetrahydro-1 (2H)-pyridinecarboxylate (Compound 11)
Starting Material: ethyl 3-amino-3-(4-methoxyphenyl)-propionate hydrochloride
Yield=59%; $^1$H-NMR (400 MHz, CDCl$_3$): δ 0.9~1.7 (m, 39H), 2.05 (m, 1H), 2.6 (bs, 4H), 2.8 (dq, 2H), 3.75 (s, 3H), 4.0 (m, 8H), 5.38 (q, 1H), 6.55 (t, 1H), 6.85 (d, 2H), 7.2 (d, 2H), 7.45 (d, 1H).

4) tert-Butyl 4-(5-[1-(tert-Butoxycarbonyl)-4-piperidyl]-3-{[(2-{[3-ethoxy-1-(3,4-dimethoxyphenyl)-3-oxopropyl] amino}-2-oxoethyl)amino]carbonyl}pentyl)tetrahydro-1 (2H)-pyridinecarboxylate (Compound 12)

Starting Material: ethyl 3-amino-3-(3,4-dimethoxyphenyl) propionate hydrochloride Yield=82%.

5) tert-Butyl 4-[5-[1-(tert-Butoxycarbonyl)-4-piperidyl]-3-({[2-({3-ethoxy-1-[3-(2-ethoxy-2-oxoethoxy)phenyl]-3-oxopropyl}amino)-2-oxoethyl]amino}carbonyl)pentyl] tetrahydro-1(2H)-pyridinecarboxylate (Compound 13)

Starting Material: ethyl 3-amino-3-(3-(2-ethoxy-2-oxoethoxy)phenyl)propionate hydrochloride Yield=61%; $^1$H-NMR (400 MHz, CDCl$_3$) δ 0.9~1.7 (m, 42H), 2.05 (m, 1H), 2.6 (bs, 4H), 2.8 (dq, 2H), 4.0 (m, 8H), 4.28 (q, 2H), 4.6 (s, 2H), 5.4 (q, 1H), 6.5 (t, 1H), 6.8 (dd, 1H), 6.9 (m, 2H), 7.2 (d, 1H), 7.45 (d, 1H).

6) tert-Butyl 4-(5-[1-(tert-Butoxycarbonyl)-4-piperidyl]-3-{[(2-{[3-ethoxy-1-(3-methoxyphenyl)-3-oxopropyl] amino}-2-oxoethyl)amino]carbonyl}pentyl)tetrahydro-1(2H)-pyridinecarboxylate (Compound 14)

Starting Material: ethyl 3-amino-3-(3-methoxyphenyl) propionate hydrochloride

Yield=78%; $^1$H-NMR (400 MHz, CDCl$_3$): δ 0.9~1.7 (m, 39H), 2.05 (m, 1H), 2.6 (bs, 4H), 2.83 (dq, 2H), 3.8 (s, 3H), 4.0 (m, 8H), 5.4 (q, 1H), 6.5 (t, 1H), 6.8 (dd, 1H), 6.85 (m, 2H), 7.2 (t, 1H), 7.45 (d, 1H).

7) tert-Butyl 4-{3-{[1-(2,3-Dihydro-1,4-benzodioxin-6-yl)-3-ethoxy-3-oxopropyl]amino}-2-oxoethyl)amino] carbonyl}-5-[1-(tert-butoxycarbonyl)-4-piperidyl] pentyl}tetrahydro-1(2H)-pyridinecarboxylate (Compound 15)

Starting Material: ethyl 3-amino-3-(2,3-dihydro-1,4-benzodioxin-6-yl)propionate hydrochloride Yield=83%; $^1$H-NMR (400 MHz, CDCl$_3$): δ 0.9~1.7 (m, 39H), 2.05 (m, 1H), 2.65 (bs, 4H), 2.8 (dq, 2H), 4.0 (m, 8H), 4.25 (s, 4H), 5.3 (m, 1H), 6.55 (t, 1H), 6.79 (s, 1H), 6.81 (d, 2H), 7.5 (d, 1H).

8) tert-Butyl 4-(5-[1-(tert-Butoxycarbonyl)-4-piperidyl]-3-{[(2-{[3-ethoxy-1-(3-pyridyl)-3-oxopropyl]amino}-2-oxoethyl)amino]carbonyl}pentyl)tetrahydro-1(2H)-pyridinecarboxylate (Compound 16)

Starting Material: ethyl 3-amino-3-(3-pyridyl)propionate dihydrochloride

Yield=69%;

9) tert-Butyl 4-(5-[1-(tert-Butoxycarbonyl)-4-piperidyl]-3-{[(2-{[3-ethoxy-3-oxopropyl]amino}- 2-oxoethyl)amino] carbonyl}pentyl)tetrahydro-1(2H)-pyridinecarboxylate (Compound 17)

Starting Material: ethyl 3-aminopropionate hydrochloride

Yield=69%; $^1$H-NMR (400 MHz, CDCl$_3$): δ 1.05 (m, 4H), 1.2 (m, 4H), 1.25 (t, 3H), 1.3 (m, 2H), 1.4 (s, 20H), 1,6 (m, 6H), 2.05 (m, 1H), 2.5 (t, 2H), 2.6 (bt, 4H), 3.5 (q, 2H), 3.9 (d, 2H), 4.0 (bs, 4H), 4.15 (q, 2H), 6.4 (bt, 1H), 6.65 (bt, 1H).

10) tert-Butyl 4-(5-[1-(tert-Butoxycarbonyl)-4-piperidyl]-3-{[(2-{[3-ethoxy-1-methyl-3-oxopropyl]amino}-2-oxoethyl)amino]carbonyl}pentyl)tetrahydro-1(2H)-pyridinecarboxylate (Compound 18)

Starting Material: ethyl 3-aminobutanoate hydrochloride

Yield=70%; $^1$H-NMR (400 MHz, CDCl$_3$): δ 1.0 (m, 4H), 1.1~1.35 (m, 13H), 1.4 (s, 19H), 1.55 (m, 6H), 2.05 (m, 1H), 2.5 (m, 2H), 2.6 (bt, 4H), 3.85 (m, 2H), 4.0 (bs, 4H), 4.1 (q, 2H), 4.3 (m, 1H), 6.4 (t, 1H), 6.75 (d, 1H).

11) tert-Butyl 4-(5-[1-(tert-Butoxycarbonyl)-4-piperidyl]-3-{[(2-{[3-ethoxy-3-oxo-1-phenethylpropyl]amino}-2-oxoethyl)amino]carbonyl}pentyl)tetrahydro-1(2H)-pyridinecarboxylate (Compound 19)

Starting Material: ethyl 3-amino-5-phenylpentanoate hydrochloride

Yield=27%; $^1$H-NMR (400 MHz, CDCl$_3$): δ 1.0 (m, 4H), 1.1~1.3 (m, 10H), 1.4 (s, 19H), 1.55 (m, 6H), 1.85 (m, 2H), 2.0 (m, 1H), 2.5 (d, 2H), 2.6 (m, 6H), 3.85 (d, 2H), 4.0 (bs, 4H), 4.1 (q, 2H), 4.25 (m, 1H), 6.25 (t, 1H), 6.6 (d, 1H), 7.1 (m, 3H), 7.2 (t, 2H).

12) Synthesis of tert-Butyl 4-{3-({[2-({1-[(1-Adamantylamino)carbonyl]-(1S)-3-benzyloxy-3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 20)

Isobutyl chloroformate (1.7 g, 12.4 mmol) is added, at room temperature, to a solution of 2-[(4-[1-(tert-butoxycarbonyl)-4-piperidyl]-2-{2-[1-(tert-butoxycarbonyl)-4-piperidyl]ethyl}butanoyl)amino]acetic acid (compound 4) (6.9 g, 11 mmol) in 150 ml of ethyl acetate and N-methylmorpholine (5 g, 49.5 mmol). A white suspension is obtained. After stirring for 10 minutes, a solution of benzyl (3S)-3-amino-4-(1-adamantylamino)-4-oxobutanoate trifluoroacetate (6.9 g, 11.2 mmol) in 20 ml of ethyl acetate is added. Stirring is continued at room temperature for 18 hours. 2N hydrochloric acid is added. The organic phase is washed with water, dried over sodium sulphate and evaporated to give the crude product, which is purified by flash chromatography (20/1 dichloromethane/methanol) to give 6.6 g of a beige-coloured solid.

Yield=68%.

The method described above was used to prepare the following compounds:

13) tert-Butyl 4-{3-({[2-({1-[[2-(1H-Indol-4-yl)ethyl] amino]carbonyl]-(1S)-3-benzyloxy-3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 21)

Starting Material: benzyl (3S)-3-amino-4-[2-(1H-indol-4-yl)ethylamino]-4-oxobutanoate trifluoroacetate Yield=49%; $^1$H-NMR (400 MHz, CDCl$_3$): δ 1.05 (m, 4H), 1.25 (m, 6H), 1.45 (s, 20H), 1.6 (m, 6H), 2.05 (m, 1H), 2.65 (m, 5H), 2.95 (m, 3H), 3.55 (m, 2H), 3.78 (dq, 2H), 4.05 (bs, 4H), 4.8 (m, 1H), 5.05 (s, 2H), 6.3 (t, 1H), 6.8 (t, 1H), 7.0 (d, 1H), 7.1 (t, 1H), 7.2 (m, 2H), 7.35 (m, 6H), 7.6 (d, 1H), 8.2 (s, 1H).

14) tert-Butyl 4-{3-({[2-({1-[{(4-Methoxyphenethyl) amino}carbonyl]-(1S)-3-benzyloxy-3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 22)

Starting Material: benzyl (3S)-3-amino-4-[(4-methoxyphenethyl)amino]-4-oxobutanoate trifluoroacetate Yield=59%; $^1$H-NMR (400 MHz, CDCl$_3$): δ 1.05 (m, 4H), 1.25 (m, 6H), 1.45 (s, 20H), 1.6 (m, 6H), 2.05 (m, 1H), 2.65 (m, 7H), 3.05 (dd, 1H), 3.4 (m, 2H), 3.75 (s, 3H), 3.85 (d, 2H), 4.05 (bs, 4H), 4.78 (m, 1H), 5.1 (s, 2H), 6.4 (t, 1H), 6.8 (m, 3H), 7.1 (d, 2H), 7.2 (d, 1H), 7.4 (m, 5H).

15) tert-Butyl 4-{3-({[2-({1-[{(3-Phenylpropyl) amino}carbonyl]-(1S)-3-benzyloxy-3-oxopropyl}amino)-2-oxoethyl]amino}carbonyl)-5-[1-(tert-butoxycarbonyl)-4-piperidyl]-pentyl}tetrahydro-1(2H)-pyridinecarboxylate (Compound 23)

Starting Material: benzyl (3S)-3-amino-4-[(3-phenylpropyl)amino]-4-oxobutanoate trifluoroacetate Yield=79%.

16) tert-Butyl 4-{3-({[2-({1-[{(1,3-Benzodioxol-5-ylmethyl)amino}carbonyl]-(1S)-3-benzyloxy-3-oxoproyl}amino)-2-oxoethyl]amino}carbonyl)-5-[1-(tert-butoxycarbonyl)-4-piperidyl]pentyl}tetrahydro-1(2H)-pyridinecarboxylate (Compound 24)

Starting Material: benzyl (3S)-3-amino-4-[(1,3-benzodioxol-5-ylmethyl)amino]-4-oxobutanoate trifluoroacetate Yield=54%.

17) tert-Butyl 4-{3-({[2-({1-[{(3-Methoxyphenethyl)amino}carbonyl]-(1S)-3-benzyloxy- 3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 25)
Starting Material: benzyl (3S)-3-amino-4-[(3-methoxyphenethyl)amino]-4-oxobutanoate trifluoroacetate Yield=65%; $^1$H-NMR (400 MHz, CDCl$_3$): δ 0.95~1.25 (m, 7H), 1.25~1.5 (m, 23H), 1.6 (m, 6H), 2.05 (m, 1H), 2.65 (m, 4H), 2.75 (t, 2H), 3.05 (dd, 1H), 3.45 (q, 2H), 3.8 (s, 3H), 3.85 (d, 2H), 4.05 (bs, 4H), 4.78 (m, 1H), 5.1 (s, 2H), 6.48 (t, 1H), 6.75 (m, 3H), 6.9 (t, 1H), 7.4 (m, 6H).

18) tert-Butyl 4-{3-({[2-({1-[{(2-Hydroxy-1,1-dimethylethyl)amino}carbonyl]-(1S)-3-benzyloxy-3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 26)
Starting Material: benzyl (3S)-3-amino-4-[(2-hydroxy-1,1-dimethylethyl)amino]-4-oxobutanoate trifluoroacetate Yield=34%; $^1$H-NMR (400 MHz, CDCl$_3$): δ 1.05 (m, 5H), 1.15~1.35 (m, 12H), 1.45 (s, 20H),1.65 (m, 7H), 2.1 (m, 1H), 2.62 (m, 6H), 3.08 (dd, 1H), 3.5 (q, 2H), 3.8 (dd, 2H), 4.0 (bs, 4H), 4.8 (m, 1H), 5.1 (s, 2H), 6.8 (s, 1H), 6.9 (t, 1H), 7.8 (m, 6H).

19) tert-Butyl 4-{3-({[2-({1-[{(1-Isopropyl-2-methylpropyl)amino}carbonyl]-(1S)-3-benzyloxy-3-oxopropyl}amino)-2-oxoethyl]amino}carbonyl)-5-[1-(tert-butoxycarbonyl)-4-piperidyl]pentyl}tetrahydro-1(2H)-pyridinecarboxylate (Compound 27)
Starting Material: benzyl (3S)-3-amino-4-[(1-isopropyl-2-methylpropyl)amino]-4-oxobutanoate trifluoroacetate Yield=59%; $^1$H-NMR (400 MHz, CDCl$_3$): δ 0.9 (m, 9H), 1.0~1.35 (m, 11H), 1.4 (s, 20H), 1.6 (bs, 6H), 1.79 (m, 2H), 2.05 (m, 1H), 2.65 (m, 6H), 3.1 (dd, 1H), 3.55 (m, 1H), 3.9 (d, 2H), 4.05 (bs, 5H), 4.82 (m, 1H), 5.15 (dd, 2H), 6.3 (t, 1H), 6.45 (d, 1H), 7.3 (m, 6H).

20) tert-Butyl 4-{3-({[2-({(1S)-3-(Benzyloxy)-3-oxo-1-[(4-benzylpiperidino)carbonyl]-propyl}amino)-2-oxoethyl]amino}carbonyl)-5-[1-(tert-butoxycarbonyl)-4-piperidyl]pentyl}tetrahydro-1(2H)-pyridinecarboxylate (Compound 28)
Starting Material: benzyl (3S)-3-amino-4-oxo-4-(4-benzylpiperidino)butanoate trifluoroacetate Yield=55%.

C-2-Preparation of the Compounds of Formula Ib (R$_1$=H, R$_2$≠H)

1) Synthesis of tert-Butyl 4-[(10S)-3-{2-[1-(tert-Butoxycarbonyl)-4-piperidyl]ethyl}-10-(ethoxycarbonyl)-4,7,12-trioxo-14-phenyl-13-oxa-5,8,11-triazatetradec-1-yl]tetrahydro-1(2H)-pyridinecarboxylate (Compound 29)

Isobutyl chloroformate (13 g, 95.2 mmol) is added, at room temperature, to a solution of 2-[(4-[1-(tert-butoxycarbonyl)-4-piperidyl]-2-{2-[1-(tert-butoxycarbonyl)-4-piperidyl]ethyl}butanoyl)amino]acetic acid (compound 4) (46 g, 85.2 mmol) in 550 ml of ethyl acetate and N-methylmorpholine (19 g, 188 mmol), and a suspension is obtained. After stirring for 20 minutes, ethyl (2S)-3-amino-2-{[(benzyloxy)carbonyl]amino}propanoate hydrochloride (26.3 g, 86.9 mmol) is added. Stirring is continued for 18 hours at room temperature and the reaction medium is then washed with water, with 1N hydrochloric acid and with water and then dried over sodium sulphate and evaporated to give the crude product, which is purified by flash chromatography (20/1 dichloromethane/methanol) to give 61 g of a white solid.

Yield=91%; $^1$H-NMR (400 MHz, CDCl$_3$): δ 1.0 (m, 4H), 1.15 (m, 4H), 1.25 (m, 5H), 1.4 (s, 20H), 1.65 (m, 6H), 2.0 (m, 1H), 2.62 (bt, 4H), 3.62 (bs, 2H), 3.85 (m, 2H), 4.05 (bs, 4H), 4.2 (bt, 2H), 4.4 (m, 1H), 5.08 (s, 2H), 5.95 (d, 1H), 6.4 (bs, 1H), 6.9 (bs, 1H), 7.4 (bs, 5H).

The method described above was used to prepare the following compounds:

2) tert-Butyl 4-[5-[1-(tert-Butoxycarbonyl)-4-piperidyl]-3-({[2-({2-[(cyclohexylsulphonyl)amino]-3-methoxy-3-oxopropyl}amino)-2-oxoethyl]amino}carbonyl)pentyl]tetrahydro-1(2H)-pyridinecarboxylate (Compound 30)
Starting Material: methyl 3-amino-2-[(cyclohexylsulphonyl)amino]propanoate trifluoroacetate Yield=81%; $^1$H-NMR (400 MHz, CDCl$_3$): δ 1.05 (m, 4H), 1.1~1.5 (m, 31H), 1.6 (m, 6H), 1.7 (bd, 1H), 1.85 (bd, 2H), 2.05 (m, 1H), 2.2 (bt, 2H), 2.60 (bt, 4H), 2.85 (m, 1H) 3.55 (m, 1H), 3.7 (m, 1H), 3.80 (s, 3H), 3.95 (m, 2H), 4.05 (bs, 4H), 4.2 (m, 1H), 5.7 (d, 1H), 6.55 (t, 1H), 6.95 (t, 1H).

3) tert-Butyl 4-[5-[1-(tert-Butoxycarbonyl)-4-piperidyl]-3-({[2-({2-[(isopropylsulphonyl)amino]-3-ethoxy-3-oxopropyl}amino)-2-oxoethyl]amino}carbonyl)pentyl]tetrahydro-1(2H)-pyridinecarboxylate (Compound 31)
Starting Material: ethyl 3-amino-2-[(isopropylsulphonyl)amino]propanoate trifluoroacetate Yield 60%; $^1$H-NMR (400 MHz, CDCl$_3$): δ 1.05 (m, 4H), 1.2 (m, 4H), 1.3 (t, 3H), 1.35 (dd, 6H), 1.45 (s, 21H), 1.6 (m, 6H), 2.05 (m, 1H), 2.65 (bt, 4H), 3.15 (m, 1H), 3.55 (m, 1H), 3.75 (m, 1H), 3.95 (t, 2H), 4.05 (bs, 4H), 4.20 (m, 1H), 4.25 (q, 2H), 5.6 (d, 1H), 6.45 (t, 1H), 6.85 (t, 1H).

4) tert-Butyl 4-{3-({[2-({2-[(1,3-Benzothiazol-2-ylsulphonyl)amino]-3-ethoxy-3-oxoproyl}amino)-2-oxoethyl]amino}carbonyl)-5-[1-(tert-butoxycarbonyl)-4-piperidyl]pentyl}tetrahydro-1(2H)-pyridinecarboxylate (Compound 32)
Starting Material: ethyl 3-amino-2-[(1,3-benzothiazol-2-ylsulphonyl)amino]propanoate hydrochloride Yield=43%; $^1$H-NMR (400 MHz, CDCl$_3$): δ 1.05 (m, 4H), 1.15 (t, 3H), 1.20 (m, 4H), 1.3 (m, 2H), 1.45 (s, 20H), 1.60 (m, 6H), 2.10 (m, 1H), 2.65 (bt, 4H), 3.70 (m, 1H), 3.80 (m, 1H), 3.95 (d, 2H), 4.05 (m, 6H), 4.55 (dd, 1H), 6.50 (t, 1H), 6.85 (bs, 1H), 7.10 (t, 1H), 7.55 (m, 2H), 7.95 (dd, 1H), 8.10 (dd, 1H).

5) tert-Butyl 4-[(11S)-3-{2-[1-(tert-Butoxycarbonyl)-4-piperidyl]ethyl}-11-(ethoxycarbonyl)-4,8,13-trioxo-15-phenyl-14-oxa-5,9,12-triazapentadec-1-yl]tetrahydro-1(2H)-pyridinecarboxylate (Compound 33)
Starting Material: compound 5 and ethyl (2S)-3-amino-2-{[(benzyloxy)carbonyl]amino}propanoate hydrochloride Yield=65%; $^1$H-NMR (400 MHz, CDCl$_3$): δ 1.0 (m, 4H), 1.15 (m, 4H), 1.25 (t, 5H), 1.4 (s, 20H), 1.55 (m, 6H), 1.9 (m, 1H), 2.3 (bt, 2H), 2.60 (bq, 4H), 3.4 (m, 2H), 3.6 (t, 2H), 4.0 (bs, 4H), 4.2 (q, 2H), 4.4 (m, 1H), 5.05 (s, 2H), 5.95 (d, 1H), 6.4 (t, 1H), 6.55 (t, 1H), 7.3 (s, 5H).

6) tert-Butyl 4-[5-[1-(tert-Butoxycarbonyl)-4-piperidyl]-3-({[3-({3-ethoxy-2-[(2-naphthylsulphonyl)amino]-3-oxopropyl}amino)-1-methyl-3-oxopropyl]amino}carbonyl)pentyl]tetrahydro-1(2H)-pyridinecarboxylate (Compound 34)
Starting Materials: compound 6 and ethyl (2S)-3-amino-2-[(2-naphthylsulphonyl)amino]propanoate hydrochloride Yield=75%; $^1$H-NMR (400 MHz, CDCl$_3$): δ 0.9 (t, 3H), 1.05 (m, 3H), 1.20 (m, 8H), 1.30 (m, 2H), 1.45 (s, 20H), 1.60 (m, 6H), 1.95 (m, 1H), 2.40 (dq, 2H), 2.65 (bt, 4H), 3.50 (m, 1H), 3.65 (m, 1H), 3.85 (m, 2H), 4.05 (m, 5H), 4.30 (m, 1H), 6.05 (d, 1H), 6.65 (m, 2H), 7.65 (m, 2H), 7.80 (d, 1H), 7.90 (d, 1H), 8.00 (d, 2H), 8.40 (s, 1H).

7) tert-Butyl 4-[5-[1-(tert-Butoxycarbonyl)-4-piperidyl]-3-({[3-({3-ethoxy-2-[(2-naphthylsulphonyl)amino]-3-oxopropyl}amino)-3-oxo-1-phenylpropyl]amino}carbonyl)pentyl]tetrahydro-1(2H)-pyridinecarboxylate (Compound 35)

Starting Materials: compound 7 and ethyl (2S)-3-amino-2-[(2-naphthylsulphonyl)amino]propanoate hydrochloride
Yield=77%; ¹H-NMR (400 MHz, CDCl₃): δ 0.95 (t,3H), 1.00 (m, 4H), 1.10 (m, 4H), 1.30 (m, 2H), 1.45 (s, 20H), 1.60 (m, 6H), 2.05 (m, 1H), 2.65 (bd, 4H), 2.70 (m, 2H), 3.40 (m, 1H), 3.60 (m, 1H), 3.80 (m, 2H), 4.00 (m, 6H), 5.40 (m, 1H), 5.85 (d, 1H), 6.40 (m, 1H), 7.25 (m, 5H), 7.65 (m, 2H), 7.76 (m, 1H), 7.90 (d, 1H), 7.95 (m, 2H), 8.40 (d, 1H).

8) tert-Butyl 4-[5-[1-(tert-Butoxycarbonyl)-4-piperidyl]-3-{[(3R)-3-[({3-ethoxy-2-[(2-naphthylsulphonyl)amino]-3-oxopropyl}amino)carbonyl]tetrahydro-1(2H)-pyridinyl]carbonyl}pentyl)tetrahydro-1(2H)-pyridinecarboxylate (Compound 36)
Starting Materials: compound 8 and ethyl (2S)-3-amino-2-[(2-naphthylsulphonyl)amino]propanoate hydrochloride
Yield=67%.

9) Synthesis of tert-Butyl 4-{3-{[(2-{[(2S)-2-Amino-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate Hydrochloride (Compound 37)
A mixture of tert-Butyl 4-[(10S)-3-{2-[1-(tert-butoxycarbonyl)-4-piperidyl]ethyl}-10-(ethoxycarbonyl)-4,7,12-trioxo-14-phenyl-13-oxa-5,8,11-triazatetradec-1-yl]tetrahydro-1(2H)-pyridinecarboxylate (compound 29) (60 g, 76.1 mmol), 10% palladium-on-charcoal (5 g) in 400 ml of ethanol and 77 ml of 1N hydrochloric ethanol is hydrogenated at room temperature under about 25 psi for 30 minutes. The resulting mixture is filtered and evaporated to give 52 g of a beige-coloured solid.
Yield=99%; ¹H-NMR (400 MHz, CDCl₃): δ 1.0 (m, 4H), 1.18 (m, 4H), 1.27 (t, 5H), 1.42 (s, 20H), 1.58 (m, 6H), 2.0 (m, 1H), 2.6 (bt, 4H), 3.35 (m, 1H), 3.55 (m, 1H), 3.68 (m, 1H), 3.9 (d, 2H), 4.02 (bs, 4H), 4.18 (q, 2H), 6.38 (bt, 1H), 6.72 (bt, 1H).

The method described above was used to prepare the following compounds:

10) Synthesis of tert-Butyl 4-{3-{[(3-{[(2S)-2-Amino-3-ethoxy-3-oxoproyl]amino}-3-oxopropyl)amino]carbonyl}-5-[1-(tert-butoxycarbonyl)-4-piperidyl]pentyl}tetrahydro-1(2H)-pyridinecarboxylate (Compound 38)
Starting Material: Compound 33
Yield=97%.

11) Synthesis of tert-Butyl 4-[5-[1-(tert-Butoxycarbonyl)-4-piperidyl]-3-({[2-({(2S)-3-ethoxy-3-oxo-2-[(phenylsulphonyl)amino]propyl}amino)-2-oxoethyl]amino}carbonyl)pentyl]tetrahydro-1(2H)-pyridinecarboxylate (Compound 39)
tert-Butyl 4-{3-{[(2-{[(2S)-2-amino-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (compound 37) (3.31 g, 4.8 mmol) is dissolved in 50 ml of dichloromethane containing triethylamine (1.04 g, 5 mmol) and benzenesulphonyl chloride (0.9 g, 5 mmol) is then added at about 5° C. After 2 hours at room temperature, water is added. The organic phase is washed with 1N HCl and then with water, dried over sodium sulphate and then evaporated to give the crude product, which is purified by flash chromatography (15/1 dichloromethane/methanol) to give 2.8 g of a white solid.
Yield=74%; ¹H-NMR (400 MHz, CDCl₃): δ 1.05 (m, 7H), 1.25 (m, 6H), 1.45 (s, 20H), 1.6 (m, 6H), 2.08 (m, 1H), 2.6 (bs, 4H), 3.5 (m, 1H), 3.67 (m, 1H), 4.0 (m, 9H), 6.28 (t, 1H), 6.62 (t, 1H), 7.1 (t, 1H), 7.5 (m, 3H), 7.82 (d, 2H).

The method described above is used to prepare the following compounds:

12) tert-Butyl 4-[5-[1-(tert-Butoxycarbonyl)-4-piperidyl]-3-({[2-({(2S)-3-ethoxy-3-oxo-2-[(1,3-benzodioxol-5-ylcarbonyl)amino]propyl}amino)-2-oxoethyl]amino}carbonyl)pentyl]tetrahydro-1(2H)-pyridinecarboxylate (Compound 40)
Starting Material: piperonylic acid chloride
Yield=74%.

13) tert-Butyl 4-[5-[1-(tert-Butoxycarbonyl)-4-piperidyl]-3-({[2-({(2S)-3-ethoxy-3-oxo-2-[(2-naphthylsulphonyl)amino]propyl}amino)-2-oxoethyl]amino}carbonyl)pentyl]tetrahydro-1(2H)-pyridinecarboxylate (Compound 41)
Starting Material: 2-naphthylsulphonyl chloride
Yield=74%; ¹H-NMR (400 MHz, CDCl₃): δ 0.95 (t, 3H), 1.05 (m, 4H), 1.2 (m, 4H), 1.35 (m, 2H), 1.45 (s, 20H), 1.6 (m, 6H), 2.1 (m, 1H), 2.63 (bt, 4H), 3.55 (m, 1H), 3.7 (m, 1H), 3.9 (q, 2H), 4.0 (m, 7H), 6.3 (bs, 1H), 6.55 (t, 1H), 7.05 (t, 1H), 7.65 (m, 2H), 7.8 (d, 1H), 7.9 (d, 1H), 7.95 (d, 2H), 8.4 (s, 1H).

14) tert-Butyl 4-[5-[1-(tert-Butoxycarbonyl)-4-piperidyl]-3-({[2-({(2S)-3-ethoxy-3-oxo-2-[(4-propylphenylsulphonyl)amino]propyl}amino)-2-oxoethyl]amino}carbonyl)pentyl]tetrahydro-1(2H)-pyridinecarboxylate (Compound 42)
Starting Material: 4-propylphenylsulphonyl chloride
Yield=78%; ¹H-NMR (400 MHz, CDCl₃): δ 0.95 (t, 3H), 1.05~1.4 (m, 15H), 1.5 (s, 18H), 1.65 (m, 8H), 2.15 (m, 1H), 2.65 (bt, 6H), 3.45 (m, 1H), 3.8 (m, 1H), 4.0 (m, 9H), 6.0 (d, 1H), 6.55 (t, 1H), 6.9 (t, 1H), 7.35 (d, 2H), 7.75 (d, 2H).

15) tert-Butyl 4-[5-[1-(tert-Butoxycarbonyl)-4-piperidyl]-3-({[2-({(2S)-3-ethoxy-3-oxo-2-[((1,1'-biphenyl)-4-ylsulphonyl)amino]propyl}amino)-2-oxoethyl]amino}carbonyl)pentyl]tetrahydro-1(2H)-pyridinecarboxylate (Compound 43)
Starting Material: 4-biphenylsulphonyl chloride
Yield=81%; ¹H-NMR (400 MHz, CDCl₃): δ 1.05 (m, 7H), 1.15 (m, 4H), 1.35 (m, 2H), 1.4 (s, 20H), 1.55 (m, 6H), 2.05 (m, 1H), 2.6 (bt, 4H), 3.5 (m, 1H), 3.65 (m, 1H), 3.85~4.1 (m, 9H), 6.25 (bs, 1H), 6.6 (bt, 1H), 7.05 (bt, 1H), 7.4 (m, 3H), 7.55 (d, 2H), 7.65 (d, 2H), 7.85 (d, 2H).

16) tert-Butyl 4-[5-[1-(tert-Butoxycarbonyl)-4-piperidyl]-3-({[2-({(2S)-3-ethoxy-3-oxo-2-[(1-naphthylsulphonyl)amino]propyl}amino)-2-oxoethyl]amino}carbonyl)pentyl]tetrahydro-1(2H)-pyridinecarboxylate (Compound 44)
Starting Material: 1-naphthylsulphonyl chloride
Yield=92%; ¹H-NMR (400 MHz, CDCl₃): δ 0.9 (t, 3H), 1.05 (m, 4H), 1.2 (m, 4H), 1.3 (m, 2H), 1.45 (s, 20H), 1.6 (m, 6H), 2.05 (m, 1H), 2.6 (bt, 4H), 3.45 (m, 1H), 3.6 (m, 1H), 3.75 (m, 2H), 3.8 (m, 2H), 4.0 (m, 5H), 6.3 (d, 1H), 6.4 (bt, 1H), 6.75 (bt, 1H), 7.5 (t, 1H), 7.6 (t, 1H), 7.7 (t, 1H), 7.9 (d, 1H), 8.05 (d, 1H), 8.2 (d, 1H), 8.65 (d, 1H).

17) tert-Butyl 4-[5-[1-(tert-Butoxycarbonyl)-4-piperidyl]-3-({[2-({(2S)-3-ethoxy-3-oxo-2-[(4-(methylsulphonyl)phenylsulphonyl)amino]propyl}amino)-2-oxoethyl]amino}carbonyl)pentyl]tetrahydro-1(2H)-pyridinecarboxylate (Compound 45)
Starting Material: 4-(methylsulphonyl)phenylsulphonyl chloride
Yield=80%; ¹H-NMR (400 MHz, CDCl₃): δ 1.0 (m, 4H), 1.1 (t, 3H), 1.2 (m, 4H), 1.3 (m, 2H), 1.4 (m, 20H), 1.6 (m, 6H), 2.05 (m, 1H), 2.65 (bt, 4H), 3.1 (s, 3H), 3.55 (m, 1H), 3.65 (m, 1H), 3.9 (d, 2H), 4.0 (m, 7H), 6.6 (bt, 2H), 7.05 (bt, 1H), 8.05 (dd, 4H).

18) tert-Butyl 4-[5-[1-(tert-Butoxycarbonyl)-4-piperidyl]-3-({[2-({(2S)-3-ethoxy-3-oxo-2-[(2-thienylsulphonyl)amino]propyl}amino)-2-oxoethyl]amino}carbonyl)pentyl]tetrahydro-1(2H)-pyridinecarboxylate (Compound 46)
Starting Material: 2-thienylsulphonyl chloride
Yield=78%; ¹H-NMR (400 MHz, CDC₃): δ 1.0 (m, 4H), 1.15 (m, 7H), 1.3 (m, 2H), 1.4 (s, 20H), 1.6 (m, 6H), 2.05

(m, 1H), 2.6 (bt, 4H), 3.55 (m, 1H), 3.7 (m, 1H), 3.9 (dq, 2H), 4.05 (m, 7H), 6.25 (bs, 1H), 6.55 (bt, 1H), 6.95 (bt, 1H), 7.05 (dd, 1H), 7.55 (dd, 2H).

19) tert-Butyl 4-{5-[1-(tert-Butoxycarbonyl)-4-piperidyl]-3-[({2-[((2S)-2-{[(4-chlorophenyl)sulphonyl]amino}-3-ethoxy-3-oxopropyl)amino]-2-oxoethyl}amino)carbonyl]pentyl}tetrahydro-1(2H)-pyridinecarboxylate (Compound 47)

Starting Material: 4-chlorophenylsulphonyl chloride

Yield=63%; $^1$H-NMR (400 MHz, CDCl$_3$): δ 1.05 (m, 4H), 1.15 (t, 3H), 1.2 (m, 4H), 1.3 (m, 2H), 1.4 (s, 20H), 1.6 (m, 6H), 2.05 (m, 1H), 2.6 (bt, 4H), 3.45 (m, 1H), 3.7 (m, 1H), 4.0 (m, 9H), 6.1 (bd, 1H), 6.45 (bt, 1H), 6.95 (bt, 1H), 7.45 (d, 2H), 7.75 (d, 2H).

20) tert-Butyl 4-{5-[1-(tert-Butoxycarbonyl)-4-piperidyl]-3-[({2-[((2S)-2-{[(4-fluorophenyl)sulphonyl]amino}-3-ethoxy-3-oxopropyl)amino]-2-oxoethyl}amino)carbonyl]pentyl}tetrahydro-1(2H)-pyridinecarboxylate (Compound 48)

Starting Material: 4-fluorophenylsulphonyl chloride

Yield=82%; $^1$H-NMR (400 MHz, CDCl$_3$): δ 1.05 (m, 4H), 1.15 (t, 3H), 1.2 (m, 4H), 1.3 (m, 2H), 1.45 (s, 20H), 1.6 (m, 6H), 2.1 (m, 1H), 2.65 (bt, 4H), 3.5 (m, 1H), 3.7 (m, 1H), 4.1 (m, 9H), 6.2 (bs, 1H), 6.55 (bt, 1H), 7.0 (bt, 1H), 7.2 (t, 2H), 7.85 (dd, 2H).

21) tert-Butyl 4-[5-[1-(tert-Butoxycarbonyl)-4-piperidyl]-3-({[2-({(2S)-3-ethoxy-3-oxo-2-[(6-methoxy-2-naphthylsulphonyl)amino]propyl}amino)-2-oxoethyl]amino}carbonyl)pentyl]tetrahydro-1(2H)-pyridinecarboxylate (Compound 49)

Starting Material: 6-methoxy-2-naphthylsulphonyl chloride

Yield=71%; $^1$H-NMR (400 MHz, CDCl$_3$): δ 0.95 (t, 3H), 1.0 (m, 4H), 1.15 (m, 4H), 1.25 (m, 2H), 1.45 (s, 20H), 1.6 (m, 6H), 2.05 (m, 1H), 2.6 (bt, 4H), 3.45 (m, 1H), 3.7 (m, 1H), 3.75 (q, 2H), 3.9 (s, 3H), 4.0 (m, 8H), 6.05 (bd, 1H), 6.45 (bt, 1H), 6.75 (bt, 1H), 7.1 (d, 1H), 7.2 (d, 1H), 7.75 (m, 3H), 8.25 (s, 1H).

22) tert-Butyl 4-[5-[1-(tert-Butoxycarbonyl)-4-piperidyl]-3-({[2-({(2S)-3-ethoxy-3-oxo-2-[(mesitylsulphonyl)amino]propyl}amino)-2-oxoethyl]amino}carbonyl)pentyl]tetrahydro-1(2H)-pyridinecarboxylate (Compound 50)

Starting Material: mesitylsulphonyl chloride

Yield=67%; $^1$H-MMR (400 MHz, CDCl$_3$): δ 1.0 (m, 4H), 1.10 (t, 3H), 1.20 (m, 4H), 1.35 (m, 2H), 1.45 (s, 20H), 1.65 (m, 6H), 2.05 (m, 1H), 2.25 (s, 3H), 2.65 (s, 6H), 2.67 (m, 4H), 3.50 (m, 1H), 3.65 (m, 1H), 3.85~4.15 (m, 9H), 5.90 (d, 1H), 6.40 (bt, 1H), 6.70 (bt, 1H), 6.90 (s, 2H).

23) tert-Butyl 4-[5-[1-(tert-Butoxycarbonyl)-4-piperidyl]-3-({[2-({(2S)-3-ethoxy-3-oxo-2-[(butylsulphonyl)amino]propyl}amino)-2-oxoethyl]amino}carbonyl)pentyl]tetrahydro-1(2H)-pyridinecarboxylate (Compound 51)

Starting Material: n-butylsulphonyl chloride

Yield=66%; $^1$H-NMR (400 MHz, CDCl$_3$): δ 0.9 (t, 3H), 1.0 (m, 4H), 1.15 (m, 4H), 1.25~1.4 (s, 27H), 1.6 (m, 6H), 1.75 (m, 2H), 2.05 (m, 1H), 2.65 (bt, 4H), 3.0 (t, 2H), 3.5 (m, 1H), 3.75 (m, 1H), 3.9 (t, 2H), 4.05 (bs, 4H), 4.2 (m, 3H), 5.85 (d, 1H), 6.55 (bt, 1H), 7.0 (bt, 1H).

24) tert-Butyl 4-[5-[1-(tert-Butoxycarbonyl)-4-piperidyl]-3-({[2-({(2S)-3-ethoxy-3-oxo-2-[(4-methylphenylsulphonyl)amino]propyl}amino)-2-oxoethyl]amino}carbonyl)pentyl]tetrahydro-1(2H)-pyridinecarboxylate (Compound 52)

Starting Material: 4-methylphenylsulphonyl chloride

Yield=68%; $^1$H-NMR (400 MHz, CDCl$_3$): δ 1.0 (m, 4H), 1.15 (t, 3H), 1.2 (m, 4H), 1.35 (m, 2H), 1.45 (s, 20H), 1.6 (m, 6H), 2.1 (m, 1H), 2.4 (s, 3H), 2.65 (bt, 4H), 3.45 (m, 1H), 3.75 (m, 1H), 3.85~4.15 (m, 9H), 5.95 (bd, 1H), 6.5 (bt, 1H), 6.85 (bt, 1H), 7.25 (d, 2H), 7.7 (d, 2H).

25) tert-Butyl 4-[5-[1-(tert-Butoxycarbonyl)-4-piperidyl]-3-({[2-({(2S)-3-ethoxy-3-oxo-2-[(3-methylphenylsulphonyl)amino]propyl}amino)-2-oxoethyl]amino}carbonyl)pentyl]tetrahydro-1(2H)-pyridinecarboxylate (Compound 53)

Starting Material: 3-methylphenylsulphonyl chloride

Yield=86%; $^1$H-NMR (400 MHz, CDCl$_3$): δ 1.0 (m, 4H), 1.05 (t, 3H), 1.1 (m, 4H), 1.3 (m, 2H), 1.4 (s, 20H), 1.6 (m, 6H), 2.1 (m, 1H), 2.4 (s, 3H), 2.65 (bt, 4H), 3.4 (m, 1H), 3.75 (m, 1H), 3.85~4.1 (m, 9H), 5.9 (bs, 1H), 6.45 (bt, 1H), 6.8 (bt, 1H), 7.4 (d, 2H), 7.6 (m, 2H).

26) tert-Butyl 4-[(10S)-3-{2-[1-(tert-Butoxycarbonyl)-4-piperidyl]ethyl}-10-(ethoxycarbonyl)-4,7,12,12-tetraoxo-13-phenyl-12λ$^6$-thia-5,8,11-triazatridec-1-yl]tetrahydro-1(2H)-pyridinecarboxylate (Compound 54)

Starting Material: 4-benzylsulphonyl chloride

Yield=49%; $^1$H-NMR (400 MHz, CDCl$_3$): δ 1.0 (m, 4H), 1.2 (m, 4H), 1.25 (m, 5H), 1.45 (s, 20H), 1.6 (m, 6H), 2.05 (m, 1H), 2.6 (bt, 4H), 3.5 (m, 2H), 3.9 (m, 2H), 4.0 (bs, 4H), 4.2 (q, 2H), 4.3 (q, 2H), 5.75 (bd, 1H), 6.4 (bt, 1H), 6.75 (bt, 1H), 7.55 (m, 5H).

27) tert-Butyl 4-[(10S,13E)-3-{2-[1-(tert-Butoxycarbonyl)-4-piperidinyl]ethyl}-10-(ethoxycarbonyl)-4,7,12,12-tetraoxo-14-phenyl-12λ$^6$-thia-5,8,11-triaza-13-tetradecen-1-yl]tetrahydro-1(2H)-pyridinecarboxylate (Compound 55)

Starting Material: trans-β-styrenesulphonyl chloride

Yield=57%; $^1$H-NMR (400 MHz, CDCl$_3$): δ 1.0 (m, 4H), 1.1~1.2 (m, 7H), 1.3 (m, 2H), 1.45 (m, 20H), 1.6 (m, 6H), 2.05 (m, 1H), 2.6 (bt, 4H), 3.5 (m, 1H), 3.8 (m, 1H), 3.85~4.15 (m, 9H), 5.95 (bs, 1H), 6.5 (bt, 1H), 6.75 (d, 1H), 6.95 (bt, 1H), 7.35~7.5 (m, 6H).

28) tert-Butyl 4-[(10S)-3-{2-[1-(tert-Butoxycarbonyl)-4-piperidyl]ethyl}-10-(ethoxycarbonyl)-4,7,12,12-tetraoxo-14-phenyl-12λ$^6$-thia-5,8,11-triazatetradec-1-yl]tetrahydro-1(2H)-pyridinecarboxylate (Compound 56)

Starting Material: the product of hydrogenation of compound 55

Yield=96%; $^1$H-NMR (400 MHz, CDCl$_3$): δ 1.0 (m, 4H), 1.15 (m, 4H), 1.25 (m, 5H), 1.4 (s, 20H), 1.55 (m, 6H), 2.05 (m, 1H), 2.6 (bt, 4H), 3.0~3.3 (m, 3H), 3.55 (m, 1H), 3.75 (m, 1H), 3.9 (d, 2H), 4.05 (bs, 5H), 4.25 (d, 2H), 6.0 (bs, 1H), 6.55 (bt, 1H), 7.0 (bt, 1H), 7.1~7.5 (m, 5H).

29) tert-Butyl 4-[5-[1-(tert-Butoxycarbonyl)-4-piperidyl]-3-{[(2-{[(2S)-3-ethoxy-3-oxo-2-({[3-(trifluoromethyl)phenyl]sulphonyl}amino)propyl]amino}-2-oxoethyl)amino]carbonyl}pentyl)tetrahydro-1(2H)-pyridinecarboxylate (Compound 57)

Starting Material: 3-trifluoromethylphenylsulphonyl chloride

Yield=77%; $^1$H-NMR (400 MHz, CDCl$_3$): δ 1.0 (m, 7H), 1.15 (m, 4H), 1.25 (m, 2H), 1.4 (s, 20H), 1.55 (m, 6H), 2.05 (m, 1H), 2.55 (bt, 4H), 3.5 (m, 1H), 3.65 (m, 1H), 3.85~4.05 (m, 9H), 6.4 (bs, 1H), 6.55 (bt, 1H), 7.0 (bt, 1H), 7.6 (t, 1H), 7.75 (d, 1H), 7.95 (d, 1H), 8.05 (s, 1H).

30) tert-Butyl 4-[5-[1-(tert-Butoxycarbonyl)-4-piperidyl]-3-{[(2-{[(2S)-3-ethoxy-2-({[3-nitrophenyl]sulphonyl}amino)-3-oxopropyl]amino}-2-oxoethyl)amino]carbonyl}pentyl)tetrahydro-1(2H)-pyridinecarboxylate (Compound 58)

Starting Material: 3-nitrophenylsulphonyl chloride

Yield=55%; $^1$H-NMR (400 MHz, CDCl$_3$): δ 1.0 (m, 4H), 1.15 (t, 3H), 1.2 (m, 4H), 1.35 (m, 2H), 1.45 (s, 20H), 1.6 (m, 6H), 2.1 (m, 1H), 2.65 (bt, 4H), 3.65 (m, 2H), 3.9~4.2 (m, 9H), 6.65 (bt, 1H), 7.15 (t, 1H), 7.7 (t, 1H), 8.2 (d, 1H), 8.4 (d, 1H), 8.7 (s, 1H).

31) tert-Butyl 4-[5-[1-(tert-Butoxycarbonyl)-4-piperidyl]-3-{[(2-{[(2S)-3-ethoxy-2-({[3-methoxyphenyl]

sulphonyl}amino)-3-oxopropyl]amino}- 2-oxoethyl)amino]carbonyl}pentyl)tetrahydro-1(2H)pyridinecarboxylate (Compound 59)
Starting Material: 4-methoxyphenylsulphonyl chloride Yield=55%; $^1$H-NMR (400 MHz, CDCl$_3$): δ 1.0 (m, 4H), 1.15 (t, 3H), 1.2 (m, 4H), 1.35 (m, 2H), 1.45 (s, 20H), 1.65 (m, 6H), 2.05 (m, 1H), 2.65 (bt, 4H), 3.45 (m, 1H), 3.75 (m, 1H), 3.85 (s, 3H), 3.9~4.1 (m, 9H), 5.9 (bs, 1H), 6.5 (bt, 1H), 6.85 (bt, 1H), 6.95 (d, 2H), 7.75 (d, 2H).

32) tert-Butyl 4-[5-[1-(tert-Butoxycarbonyl)-4-piperidyl]-3-([{2-({(2S)-3-ethoxy-3-oxo-2-[(8-quinolylsulphonyl)amino]propyl}amino)-2-oxoethyl]amino}carbonyl)pentyl]tetrahydro-1(2H)-pyridinecarboxylate (Compound 60)
Starting Material: 8-quinolinesulphonyl chloride Yield=55%; $^1$H-NMR (400 MHz, CDCl$_3$): δ 0.9 (t, 3H), 1.05 (m, 4H), 1.2 (m, 4H), 1.3 (m, 2H), 1.45 (m, 20H), 1.6 (m, 6H), 2.05 (m, 1H), 2.65 (bt, 4H), 3.5 (m, 1H), 3.65~4.2 (m, 10H), 66.35 (bt, 1H), 6.65 (bt, 1H), 7.2 (bs, 1H), 7.55 (q, 1H), 7.65 (t, 1H), 8.05 (d, 1H), 8.25 (d, 1H), 8.35 (d, 1H), 9.05 (d, 1H).

33) tert-Butyl 4-{5-[1-(tert-Butoxycarbonyl)-4-piperidyl]-3-[({2-[((2S)-2-{[(3,5-dimethyl-4-isoxazolyl)sulphonyl]amino}-3-ethoxy-3-oxopropyl)amino]-2-oxoethyl}amino)carbonyl]pentyl}tetrahydro-1(2H)-pyridinecarboxylate (Compound 61)
Starting Material: 3,5-dimethyl-4-isoxazolylsulphonyl chloride Yield=81%; $^1$H-NMR (400 MHz, CDCl$_3$): δ 1.05 (m, 4H), 1.2 (m, 7H), 1.3 (m, 2H), 1.45 (s, 20H), 1.65 (m, 6H), 2.05 (m, 1H), 2.4 (s, 3H), 2.6 (s, 3H), 2.65 (bt, 4H), 3.5 (m, 1H), 3.7 (m, 1H), 3.85~4.1 (m, 9H), 6.4 (bs, 1H), 6.55 (bt, 1H), 7.0 (bt, 1H).

34) tert-Butyl 4-{5-[1-(tert-Butoxycarbonyl)-4-piperidyl]-3-[({2-[((2S)-2-{[(5-(dimethylamino)-1-naphthyl]sulphonyl)amino}-3-ethoxy-3-oxopropyl)amino]-2-oxoethyl}amino)carbonyl]pentyl}tetrahydro-1(2H)-pyridinecarboxylate (Compound 62)
Starting Material: 5-dimethylamino-1-naphthylsulphonyl chloride Yield=73%; $^1$H-NMR (400 MHz, CDCl$_3$): δ 0.9 (t, 3H), 1.15 (m, 4H), 1.3 (m, 2H), 1.45 (m, 20H), 1.6 (m, 6H), 2.05 (m, 1H), 2.6 (bt, 4H), 2.85 (s, 6H), 3.45 (m, 1H), 3.6 (m, 1H), 3.8 (m, 4H), 3.9~4.1 (m, 5H), 6.15 (bs, 1H), 6.35 (bt, 1H), 6.6 (bt, 1H), 7.2 (d, 1H), 7.5 (t, 1H), 7.6 (t, 1H), 8.2 (d, 1H), 8.25 (d, 1H), 8.55 (d, 1H).

35) tert-Butyl 4-{3-{[(2-{[(2S)-2-({[2-(Acetylamino)-4-methyl-1,3-thiazol-5-yl]sulphonyl}amino)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (Compound 63)
Starting Material: 2-(acetylamino)-4-methyl-1,3-thiazol-5-ylsulphonyl chloride Yield=64%; $^1$H-NMR (400 MHz, CDCl$_3$): δ 1.05 (m, 4H), 1.15~1.4 (m, 9H), 1.45 (s, 20H), 1.6 (bd, 6H), 2.1 (m, 1H), 2.3 (s, 3H), 2.45 (s, 3H), 2.65 (bt, 4H), 3.55 (m, 1H), 3.7 (m, 1H), 3.9~4.2 (m, 9H), 6.85 (bt, 1H), 7.2 (bt, 1H).

36) tert-Butyl 4-{5-[1-(tert-Butoxycarbonyl)-4-piperidyl]-3-[({2-[((2S)-2-{[(3-chloropropyl]-sulphonyl)amino}-3-ethoxy-3-oxopropyl)amino]-2-oxoethyl}amino)carbonyl]pentyl}tetrahydro-1(2H)-pyridinecarboxylate (Compound 64)
Starting Material: 3-chloropropylsulphonyl chloride Yield=68%; $^1$H-NMR (400 MHz, CDCl$_3$): δ 1.05 (m, 4H), 1.2 (m, 4H), 1.35 (m, 5H), 1.45 (s, 20H), 1.6 (m, 6H), 2.05 (m, 1H), 2.3 (m, 2H), 2.65 (bt, 4H), 3.2 (t, 2H), 3.6 (m, 1H), 3.65 (t, 2H), 3.75 (m, 1H), 3.95 (d, 2H), 4.05 (bs, 4H), 4.25 (q, 3H), 6.1 (bd, 1H), 6.6 (bt, 1H), 7.1 (bt, 1H).

37) tert-Butyl 4-{5-[1-(tert-Butoxycarbonyl)-4-piperidyl]-3-[({2-[((2S)-2-{([4-methoxy-1-naphthyl]sulphonyl)amino}-3-ethoxy-3-oxopropyl)amino]-2-oxoethyl}amino)carbonyl]pentyl}tetrahydro-1(2H)-pyridinecarboxylate (Compound 65)
Starting Material: 4-methoxy-1-naphthylsulphonyl chloride Yield=71%; $^1$H-NMR (400 MHz, CDCl$_3$): δ 0.9 (t, 3H), 1.05 (m, 4H), 1.15 (m, 4H), 1.35 (m, 2H), 1.45 (s, 20H), 1.6 (m, 6H), 2.05 (m, 1H), 2.65 (bt, 4H), 3.45 (m, 1H), 3.6 (m, 1H), 3.75~4.05 (m, 9H), 4.1 (s, 3H), 6.2 (d, 1H), 6.35 (bt, 1H), 6.65 (bt, 1H), 6.8 (d, 1H), 7.6 (t, 1H), 7.7 (t, 1H), 8.15 (d, 1H), 8.35 (d, 1H), 8.6 (d, 1H).

38) tert-Butyl 4-{5-[1-(tert-Butoxycarbonyl)-4-piperidyl]-3-[({2-[((2S)-2-{([6,7-dimethoxy-2-naphthyl]sulphonyl)amino}-3-ethoxy-3-oxopropyl)amino]-2-oxoethyl}amino)carbonyl]pentyl}tetrahydro-1(2H)-pyridinecarboxylate (Compound 66)
Starting Material: 6,7-dimethoxy-2-naphthylsulphonyl chloride Yield=63%; $^1$H-NMR (400 MHz, CDCl$_3$): δ 1.0 (t, 3H), 1.05 (m, 4H), 1.2 (m, 4H), 1.35 (m, 2H), 1.45 (s, 20H), 1.6 (m, 6H), 2.1 (m, 1H), 2.65 (bt, 4H), 3.45 (m, 1H), 3.75 (m, 1H), 3.8~4.1 (m, 15H), 6.0 (d, 1H), 6.5 (bt, 1H), 6.9 (bt, 1H), 7.15 (s, 1H), 7.2 (s, 1H), 7.3 (s, 1H), 7.7 (d, 1H), 7.8 (d, 1H), 8.25 (s, 1H).

39) tert-Butyl 4-{5-[1-(tert-Butoxycarbonyl)-4-piperidyl]-3-{[(2-{[(2S)-2-({[2,4-dimethyl-1,3-thiazol-5-yl]sulphonyl}amino)-3-ethoxy-3-oxopropyl]amino}-2-oxoethyl)amino]carbonyl}pentyl}tetrahydro-1(2H)-pyridinecarboxylate (Compound 67)
Starting Material: 2,4-dimethyl-1,3-thiazol-5-ylsulphonyl chloride Yield=54%; $^1$H-NMR (400 MHz, CDCl$_3$): δ 1.05 (m, 4H), 1.2 (m, 7H), 1.35 (m, 2H), 1.45 (s, 20H), 1.6 (m, 6H), 2.1 (m, 1H), 2.6 (s, 3H), 2.7 (m, 7H), 3.55 (m, 1H), 3.7 (m, 1H), 3.85~4.15 (m, 9H), 6.35 (d, 1H), 6.5 (bt, 1H), 6.95 (bt, 1H).

40) tert-Butyl 4-{5-[1-(tert-Butoxycarbonyl)-4-piperidyl]-3-({[2-({(2S)-2-({[3,5-dimethyl-1H-pyrazol-4-yl]sulphonyl}amino)-3-ethoxy-3-oxopropyl]amino}-2-oxoethyl)amino]carbonyl}pentyl}tetrahydro-1(2H)-pyridinecarboxylate (Compound 68)
Starting Material: 3,5-dimethyl-1H-pyrazol-4-ylsulphonyl chloride Yield=50%; $^1$H-NMR (400 MHz, CDCl$_3$): δ 1.05 (m, 4H), 1.2 (m, 7H), 1.3 (m, 2H), 1.45 (s, 20H), 1.65 (m, 6H), 2.1 (m, 1H), 2.4 (s, 6H), 2.65 (bt, 4H), 3.5 (m, 1H), 3.7 (m, 1H), 3.9 (bs, 2H), 4.05 (m, 6H), 6.4 (bd, 1H), 6.75 (bt, 1H), 7.15 (bs, 1H), 11.8 (bs, 1H).

41) tert-Butyl 4-{5-[1-(tert-Butoxycarbonyl)-4-piperidyl]-3-({[2-({2S)-3-ethoxy-3-oxo-2-[(3-pyridylsulphonyl)amino]propyl}amino)-2-oxoethyl]amino}carbonyl)pentyl]tetrahydro-1(2H)-pyridinecarboxylate (Compound 69)
Starting Material: 3-pyridylsulphonyl chloride Yield=61%; $^1$H-NMR (400 MHz, CDCl$_3$): δ 1.05 (m, 4H), 1.15 (t, 3H), 1.2 (m, 4H), 1.35 (m, 2H), 1.45 (m, 20H), 1.65 (m, 6H), 2.1 (m, 1H), 2.75 (bt, 4H), 3.6 (m, 1H), 3.7 (m, 1H), 3.9~4.15 (m, 9H), 6.65 (bt, 1H), 6.7 (d, 1H), 7.15 (bt, 1H), 7.45 (q, 1H), 8.15 (dd, 1H), 8.8 (d, 1H), 9.05 (s, 1H).

42) tert-Butyl 4-{3-{[(2-{[(2S)-2-({1,3-Benzodioxol-5-ylsulphonyl}amino)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (Compound 70)
Starting Material: 1,3-benzodioxol-5-ylsulphonyl chloride Yield=61%; $^1$H-NMR (400 MHz, CDCl$_3$): δ 1.05 (m, 4H), 1.2 (m, 7H), 1.3 (m, 2H), 1.45 (s, 20H), 1.65 (m, 6H), 2.1 (m, 1H), 2.65 (bt, 4H), 3.5 (m, 1H), 3.7 (m, 1H), 3.85~4.1 (m, 9H), 6.05 (d, 1H), 6.1 (s, 2H), 6.55 (bt, 1H), 6.85 (d, 1H), 6.9 (bt, 1H), 7.25 (d, 1H), 7.4 (d, 1H).

43) tert-Butyl 4-{5-[1-(tert-Butoxycarbonyl)-4-piperidyl]-3-{[(2-{[(2S)-2-({2,3-dihydro-1,4-benzodioxin-6-ylsulphonyl}amino)-3-ethoxy-3-oxopropyl]amino}-2-oxoethyl)amino]carbonyl}pentyl}tetrahydro-1(2H)-pyridinecarboxylate (Compound 71)
Starting Material: 2,3-dihydro-1,4-benzodioxin-6-ylsulphonyl chloride
Yield=61%; $^1$H-NMR (400 MHz, CDCl$_3$): δ 1.05 (m, 4H), 1.2 (m, 7H), 1.35 (m, 2H), 1.45 (s, 20H), 1.65 (m, 6H), 2.1 (m, 1H), 2.65 (bt, 4H), 3.45 (m, 1H), 3.75 (m, 1H), 3.9~4.1 (m, 9H), 4.3 (dd, 4H), 5.95 (bs, 1H), 6.5 (bt, 1H), 6.85 (d, 1H), 6.95 (d, 1H), 7.3 (dd, 1H), 7.35 (d, 1H).

44) tert-Butyl 4-{3-{[(2-{[(2S)-2-({1-Benzothiophen-2-ylsulphonyl}amino)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (Compound 72)
Starting Material: 1-benzothiophen-2-ylsulphonyl chloride
Yield=74%; $^1$H-NMR (400 MHz, CDCl$_3$): δ 0.95 (t, 3H), 1.05 (m, 4H), 1.2 (m, 4H), 1.3 (m, 2H), 1.45 (s, 20H), 1.6 (m, 6H), 2.1 (m, 1H), 2.65 (bt, 4H), 3.5 (m, 1H), 3.7 (m, 1H), 3.85 (m, 4H), 4.05 (m, 5H), 6.45 (bt, 2H), 6.9 (bt, 1H), 7.5 (m, 2H), 7.9 (d, 1H), 8.2 (d, 1H), 8.25 (s, 1H).

45) tert-Butyl 4-{5-[1-(tert-Butoxycarbonyl)-4-piperidyl]-3-{[(2-{[(2S)-2-({[2,5-dimethyl-3-furyl]sulphonyl}amino)-3-ethoxy-3-oxopropyl]amino}-2-oxoethyl)amino]carbonyl}pentyl}tetrahydro-1(2H)-pyridinecarboxylate (Compound 73)
Starting Material: 2,5-dimethyl-3-furylsulphonyl chloride
Yield=78%; $^1$H-NMR (400 MHz, CDCl$_3$): δ 1.05 (m, 4H), 1.2 (m, 7H), 1.3 (m, 2H), 1.45 (s, 20H), 1,6 (m, 6H), 2.1 (m, 1H), 2.25 (s, 3H), 2.5 (s, 3H), 2.65 (bt, 4H), 3.45 (m, 1H), 3.75 (m, 1H), 3.85~4.15 (m, 9H), 5.9 (bs, 1H), 6.1 (s, 1H), 6.45 (bt, 1H), 6.85 (bt, 1H).

46) tert-Butyl 4-{5-[1-(tert-Butoxycarbonyl)-4-piperidyl]-3-{[(2-{[(2S)-2-({[4-cyclohexylphenyl]sulphonyl}amino)-3-ethoxy-3-oxopropyl]amino}-2-oxoethyl)amino]carbonyl}pentyl}tetrahydro-1(2H)-pyridinecarboxylate (Compound 74)
Starting Material: 4-cyclohexylphenylsulphonyl chloride
Yield=64%; $^1$H-NMR (400 MHz, CDC$_3$): δ 1.1 (m, 7H), 1.15~1.5 (m, 30H), 1.6 (m, 6H), 1.8 (m, 6H), 2.1 (m, 1H), 2.65 (m, 5H), 3.45 (m, 1H), 3.75 (m, 1H), 3.85~4.15 (m, 9H), 5.9 (bs, 1H), 6.45 (bt, 1H), 6.85 (bt, 1H), 7.35 (d, 2H), 7.75 (d, 2H).

47) tert-Butyl 4-[5-[1-(tert-Butoxycarbonyl)-4-piperidyl]-3-{[(2-{[(2S)-3-ethoxy-2-({[4-fluoro-1-naphthyl]sulphonyl}amino)-3-oxopropyl]amino}-2-oxoethyl)amino]carbonyl}pentyl)tetrahydro-1(2H)-pyridinecarboxylate (Compound 75)
Starting Material: 4-fluoro-1-naphthylsulphonyl chloride
Yield=64%; $^1$H-NMR (400 MHz, CDCl$_3$): δ 0.9 (t, 3H), 1.05 (m, 4H), 1.2 (m,4H), 1.35 (m, 2H), 1.45 (s, 20H), 1.6 (m, 6H), 2.1 (m, 1H), 2.65 (bt, 4H), 3.5 (m, 1H), 3.65 (m, 1H), 3.8 (q, 2H), 3.85 (bd, 2H), 4.05 (m, 5H), 6.3 (bs, 1H), 6.45 (bt, 1H), 6.8 (bt, 1H), 7.2 (t, 1H), 7.7 (t, 1H), 7.75 (t, 1H), 8.23 (t, 1H), 8.65 (d, 1H).

48) tert-Butyl 4-[5-[1-(tert-Butoxycarbonyl)-4-piperidyl]-3-{[(2-{[(2S)-3-ethoxy-2-({[4-chloro-1-naphthyl]sulphonyl}amino)-3-oxopropyl]amino}-2-oxoethyl)amino]carbonyl}pentyl)tetrahydro-1(2H)-pyridinecarboxylate (Compound 76)
Starting Material: 4-chloro-1-naphthylsulphonyl chloride
Yield=63%; $^1$H-NMR (400 MHz, CDCl$_3$): δ 0.9 (t, 3H), 1.1 (m, 4H), 1.2 (m, 4H), 1.35 (m, 2H), 1.45 (s, 20H), 1.6 (m, 6H), 2.1 (m, 1H), 2.65 (bt, 4H), 3.5 (m, 1H), 3.6 (m, 1H), 3.8 (q, 2H), 3.85 (bd, 2H), 3.95~4.15 (m, 5H), 6.4 (bt, 2H), 6.8 (bt, 1H), 7.65 (d, 1H), 7.75 (m, 2H), 8.4 (d, 1H), 8.7 (d, 1H).

49) tert-Butyl 4-{5-[1-(tert-Butoxycarbonyl)-4-piperidyl]-3-{[(2-{[(2S)-2-({[2,3-dihydro-1-benzofuran-5-yl]sulphonyl}amino)-3-ethoxy-3-oxopropyl]amino}-2-oxoethyl)amino]carbonyl}pentyl}tetrahydro-1(2H)-pyridinecarboxylate (Compound 77)
Starting Material: 2,3-dihydro-1-benzofuran-5-ylsulphonyl chloride
Yield=74%; $^1$H-NMR (400 MHz, CDCl$_3$): δ 1.05 (m, 4H), 1.2 (m, 7H), 1.35 (m, 2H), 1.45 (s, 20H), 1.6 (m, 6H), 2.1 (m, 1H), 2.65 (bt, 4H), 3.25 (t, 2H), 3.45 (m, 1H), 3.75 (m, 1H), 3.85~4.1 (m, 9H), 4.65 (t, 2H), 5.8 (d, 1H), 6.45 (bt, 1H), 6.8 (d, 2H), 7.6 (d, 1H), 7.65 (s, 1H).

50) tert-Butyl 4-[5-[1-(tert-Butoxycarbonyl)-4-piperidyl]-3-({[2-({[2S)-3-ethoxy-3-oxo-2-{[4-(2-thienyl)phenylsulphonyl]amino}propyl}amino)-2-oxoethyl]amino}carbonyl)pentyl]tetrahydro-1(2H)-pyridinecarboxylate (Compound 78)
Starting Material: 4-(2-thienyl)-phenylsulphonyl chloride
Yield=78%; $^1$H-NMR (400 MHz, CDCl$_3$): δ 1.1 (m, 7H), 1.2 (m, 4H), 1.35 (m, 2H), 1.45 (s, 20H), 1.6 (m, 6H), 2.1 (m, 1H), 2.65 (bq, 4H), 3.5 (m, 1H), 3.75 (m, 1H), 3.9~4.1 (m, 9H), 6.1 (d, 1H), 6.5 (bt, 1H), 6.9 (bt, 1H), 7.1 (t, 1H), 7.4 (dd, 2H), 7.7 (d, 2H), 7.85 (d, 2H).

51) tert-Butyl 4-[5-[1-(tert-Butoxycarbonyl)-4-piperidyl]-3-({[2-({[2S)-3-ethoxy-3-oxo-2-{[2-(2-thienyl)phenylsulphonyl]amino}propyl}amino)-2-oxoethyl]amino}carbonyl)pentyl]tetrahydro-1(2H)-pyridinecarboxylate (Compound 79)
Starting Material: 2-(2-thienyl)-phenylsulphonyl chloride
Yield=63%; $^1$H-NMR (400 MHz, CDCl$_3$): δ 1.05 (m, 4H), 1.2 (m, 7H), 1.3 (m, 2H), 1.45 (s, 20H), 1.65 (m, 6H), 2.05 (m, 1H), 2.65 (bt, 4H), 3.5 (m, 2H), 3.8~4.1 (m, 9H), 5.3 (d, 1H), 6.25 (bt, 1H), 6.4 (bt, 1H), 7.15 (t, 1H), 7.5 (m, 4H), 7.6 (t, 1H), 8.1 (d, 1H).

52) tert-Butyl 4-[5-[1-(tert-Butoxycarbonyl)-4-piperidyl]-3-({[2-({[2S)-3-ethoxy-3-oxo-2-{[4-(2-furyl)phenylsulphonyl]amino}propyl}amino)-2-oxoethyl]amino}carbonyl)pentyl]tetrahydro-1(2H)-pyridinecarboxylate (Compound 80)
Starting Material: 4-(2-furyl)-phenylsulphonyl chloride
Yield=62%; $^1$H-NMR (400 MHz, CDCl$_3$): δ 1.1 (m, 7H), 1.2 (m, 4H), 1.35 (m, 2H), 1.45 (s, 20H), 1.65 (m, 6H), 2.1 (m, 1H), 2.65 (bt, 4H), 3.5 (m, 1H), 3.75 (m, 1H), 3.85~4.1 (m, 9H), 6.05 (bs, 1H), 6.5 (bt, 1H), 6.55 (d, 1H), 7.5 (s, 1H), 7.75 (d, 2H), 7.8 (d, 2H).

53) tert-Butyl 4-{3-{[(2-{[(2S)-2-({1-Benzofuran-2-ylsulphonyl}amino)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (Compound 81)
Starting Material: 1-benzofuran-2-ylsulphonyl chloride
Yield=52%; $^1$H-NMR (400 MHz, CDCl$_3$): δ 1.1 (m, 7H), 1.2 (m, 4H), 1.3 (m, 2H), 1.45 (s, 20H), 1.6 (m, 6H), 2.1 (m, 1H), 2.65 (bt, 4H), 3.65 (m, 1H), 3.75 (m, 1H), 3.9~4.15 (m, 8H), 4.25 (m, 1H), 6.45 (bt, 1H), 6.9 (bt, 1H), 7.35 (m, 2H), 7.48 (t, 1H), 7.65 (d, 1H), 7.7 (d, 1H).

54) tert-Butyl 4-[5-[1-(tert-Butoxycarbonyl)-4-piperidyl]-3-({[2-({(2S)-3-ethoxy-3-oxo-2-[(2-naphthylmethylsulphonyl)amino]propyl}amino)-2-oxoethyl]amino}carbonyl)pentyl]tetrahydro-1(2H)-pyridinecarboxylate (Compound 82)
Starting Material: 2-naphthylmethanesulphonyl chloride
Yield=61%; $^1$H-NMR (400 MHz, CDCl$_3$): δ 1.05 (m, 4H), 1.1 (t, 3H), 1.2 (m, 4H), 1.3 (m, 2H), 1.45 (s, 20H), 1.6

(m, 6H), 2.05 (m, 1H), 2.65 (bt, 4H), 3.4 (m, 1H), 3.5 (m, 1H), 3.75~4.1 (m, 9H), 4.4 (q, 2H), 5.7 (bs, 1H), 6.4 (bt, 1H), 6.7 (bt, 1H), 7.5 (m, 3H), 7.8 (m, 4H).

55) tert-Butyl 4-{5-[1-(tert-Butoxycarbonyl)-4-piperidyl]-3-{[(2-{[(2S)-2-({[2,3-dihydro-1H-inden-5-yl]sulphonyl}amino)-3-ethoxy-3-oxopropyl]amino}-2-oxoethyl)amino]carbonyl}pentyl}tetrahydro-1(2H)-pyridinecarboxylate (Compound 83)
Starting Material: 5-indanesulphonyl chloride
Yield=62%; $^1$H-NMR (400 MHz, CDCl$_3$): δ 1.05 (m, 4H), 1.1 (t, 3H), 1.2 (m, 4H), 1.35 (m, 2H), 1.45 (s, 20H), 1.6 (m, 6H), 2.05 (m, 1H), 2.1 (t, 2H), 2.65 (bt, 4H), 2.95 (t, 4H), 3.45 (m, 1H), 3.75 (m, 1H), 3.85~4.1 (m, 9H), 5.85 (d, 1H), 6.45 (bt, 1H), 6.8 (bt, 1H), 7.3 (d, 1H), 7.6 (d, 1H), 7.65 (s, 1H).

56) tert-Butyl 4-[5-[1-(tert-Butoxycarbonyl)-4-piperidyl]-3-({[2-({(2S)-3-ethoxy-3-oxo-2-{[(5-phenyl-2-thienyl)sulphonyl]amino}propyl}amino)-2-oxoethyl]amino}carbonyl)pentyl]tetrahydro-1(2H)-pyridinecarboxylate (Compound 84)
Starting Material: 5-phenyl-2-thiophenesulphonyl chloride
Yield=60%; $^1$H-NMR (400 MHz, CDCl$_3$): δ 1.05 (m, 4H), 1.15 (t, 3H), 1.2 (m, 4H), 1.35 (m, 2H), 1.45 (s, 20H), 1.6 (m, 6H), 2.05 (m, 1H), 2.65 (bt, 4H), 3.55 (m, 1H), 3.8 (m, 1H), 3.9~4.15 (m, 9H), 6.4 (bt, 1H), 6.8 (bt, 1H), 7.25 (d, 1H), 7.4 (m, 3H), 7.55 (m, 3H).

57) tert-Butyl 4-[5-[1-(tert-Butoxycarbonyl)-4-piperidyl]-3-({[2-({(2S)-3-ethoxy-3-oxo-2-[(5,6,7,8-tetrahydro-2-naphthenylsulphonyl)amino]propyl}amino)-2-oxoethyl]amino}carbonyl)pentyl]tetrahydro-1(2H)-pyridinecarboxylate (Compound 85)
Starting Material: 5,6,7,8-tetrahydro-2-naphthalenesulphonyl chloride
Yield=12%; $^1$H-NMR (400 MHz, CDCl$_3$): δ 1.05 (m, 4H), 1.1 (t, 3H), 1.2 (m, 4H), 1.3 (m, 2H), 1.45 (s, 20H), 1.6 (m, 6H), 1.8 (bs, 4H), 2.1 (m, 1H), 2.65 (bt, 4H), 2.8 (bs, 4H), 3.45 (m, 1H), 3.75 (m, 1H), 3.85~4.15 (m, 9H), 5.9 (bs, 1H), 6.5 (bt, 1H), 6.85 (bt, 1H), 7.2 (d, 1H), 7.49 (d, 1H), 7.65 (s, 1H).

58) tert-Butyl 4-[(10S,13E)-3-{2-[1-(tert-Butoxycarbonyl)-4-piperidyl]ethyl}-10-(ethoxycarbonyl)-4,7,12,12-tetraoxo-12λ$^6$-thia-5,8,11-triaza-13-heptadecen-1-yl]tetrahydro-1(2H)-pyridinecarboxylate (Compound 86)
Starting Material: (E)-1-pentenylsulphonyl chloride
Yield=21%; $^1$H-NMR (400 MHz, CDCl$_3$): δ 0.9 (t, 3H), 1.05 (m, 4H), 1.2 (m, 4H), 1.27 (t, 3H), 1.30 (m, 2H), 1.45 (s, 20H), 1.6 (m, 6H), 2.05 (m, 1H), 2.2 (q, 2H), 2.65 (bt, 4H), 3.45 (m, 1H), 3.75 (m, 1H), 3.85~4.10 (m, 7H), 4.2 (q, 2H), 5.65 (d, 1H), 6.15 (d, 1H), 6.45 (bt, 1H), 6.7.5 (dt, 1H), 6.8 (bt, 1H).

59) tert-Butyl 4-[5-[1-(tert-Butoxycarbonyl)-4-piperidyl]-3-({[3-({(3S)-3-ethoxy-2-[(2-naphthylsulphonyl)amino]-3-oxopropyl}amino)-3-oxopropyl]amino}carbonyl)pentyl]tetrahydro-1(2H)-pyridinecarboxylate (Compound 87)
Starting Materials: Compound 38 and 2-naphthylsulphonyl chloride
Yield=76%; $^1$H-NMR (400 MHz, CDCl$_3$): δ 0.95 (t, 3H), 1.05 (m, 4H), 1.2 (m, 4H), 1.30 (m, 2H), 1.45 (s, 20H), 1.6 (m, 6H), 2.0 (m, 1H), 2.4 (m, 2H), 2.65 (bq, 4H), 3.45 (m, 1H), 3.55 (m, 2H), 3.7 (m, 1H), 3.85 (q, 2H), 4.0 (bs, 4H), 4.1 (bs, 1H), 6.0 (bd, 1H), 6.75 (m, 2H), 7.65 (m, 2H), 7.8 (d, 1H), 7.9 (d, 1H), 7.95 (d, 2H), 8.4 (s, 1H).

60) tert-Butyl 4-[5-[1-(tert-Butoxycarbonyl)-4-piperidyl]-3-({[3-({(3S)-3-ethoxy-3-oxo-2-[(phenylsulphonyl)amino]propyl}amino)-3-oxopropyl]amino}carbonyl)pentyl]tetrahydro-1(2H)-pyridinecarboxylate (Compound 88)
Starting Materials: Compound 38 and benzenesulphonyl chloride Yield=76%; $^1$H-NMR (400 MHz, CDCl$_3$): δ 1.05 (m, 4H), 1.1 (t, 3H), 1.2 (m, 4H), 1.30 (m, 2H), 1.45 (s, 20H), 1.6 (m, 6H), 2.0 (m, 1H), 2.4 (t, 2H), 2.65 (bt, 4H), 3.4 (m, 1H), 3.55 (m, 2H), 3.7 (m, 1H), 4.0 (q, 2H), 4.05 (bs, 4H), 5.9 (d, 1H), 6.5 (m, 2H), 7.5 (t, 2H), 7.6 (d, 1H), 7.85 (d, 1H).

61) tert-Butyl 4-[(10S)-3-{2-[1-(tert-Butoxycarbonyl)-4-piperidyl]ethyl}-13-(7,7-dimethyl-2-oxobicyclo[2.2.1]hept-1-yl)-10-(ethoxycarbonyl)-4,7,12,12-tetraoxo-12λ$^6$-thia-5,8,11-triazatridec-1-yl]tetrahydro-1(2H)-pyridinecarboxylate (Compound 89)
According to the procedure described for compound 29, starting with ethyl (2S)-3-amino-2-({[(7,7-dimethyl-2-oxobicyclo[2.2.1]hept-1-yl)methyl]sulphonyl}amino)propanoate hydrochloride and compound 4.
Yield=78%; $^1$H-NMR (400 MHz, CDCl$_3$): δ 0.90 (s, 3H), 1.00 (s, 3H), 1.05 (m, 4H), 1.20 (m, 4H), 1.30 (t, 5H), 1.45 (s, 20H), 1.55 (m, 6H), 1.95 (t, 3H), 2.05 (m, 2H), 2.15 (t, 1H), 2.20 (m, 1H), 2.40 (m, 1H), 2.65 (bt, 4H), 3.00 (d, 1H), 3.50 (m, 2H), 3.80 (m, 1H), 3.95 (dq, 2H), 4.05 (bs, 4H), 4.20 (q, 2H), 4.30 (m, 1H), 6.40 (t, 1H), 6.50 (d, 1H), 6.70 (t, 1H).

62) (2R)-3-({2-[(4-[1-(tert-Butoxycarbonyl)-4-piperidyl]-2-{2-[1-(tert-butoxycarbonyl)-4-piperidyl]ethyl}butanoyl)amino]acetyl}amino)-2-[(2-naphthylsulphonyl)amino]propanoic Acid (Compound 90)
Isobutyl chloroformate (3.3 g, 24.2 mmol) is added, at room temperature, to a solution of 2-[(4-[1-(tert-butoxycarbonyl)-4-piperidyl]-2-{2-[1-(tert-butoxycarbonyl)-4-piperidyl]ethyl}butanoyl)amino]acetic acid (compound 4) (10.8 g, 20 mmol) in 200 ml of THF and N-methylmorpholine (5 g, 49.5 mmol). A suspension is obtained. After stirring for 20 minutes, a mixture of (2R)-3-amino-2-[(2-naphthylsulphonyl)amino]propanoic acid (8 g, 25 mmol) and water (80 ml) is added, at 0° C. Stirring is continued at 0~5° C. for 30 minutes and then at room temperature for 18 hours. The THF is evaporated off and the aqueous solution is acidified to pH 2 with 1N hydrochloric acid. The mixture is extracted with ether. The extracts are washed with water, dried over sodium sulphate and evaporated to give the crude product, which is purified by flash chromatography (10/0.5/0.5 dichloromethane/methanol/acetic acid) to give 8.3 g of a beige-coloured solid.
Yield=51%; $^1$H-NMR (400 MHz, CDCl$_3$): δ 1.0 (m, 4H), 1.15 (m, 4H), 1.25 (m, 2H), 1.4 (s, 20H), 1.55 (bd, 6H), 2.1 (m, 1H), 2.6 (bq, 4H), 3.6 (m, 1H), 3.75 (m, 1H), 3.8~4.1 (m, 7H), 6.6 (d, 1H), 6.95 (bt, 1H), 7.25 (bt, 1H), 7.6 (m, 2H), 7.85 (t, 2H), 7.95 (t, 2H), 8.45 (s, 1H).

D—Preparation of the Compounds of Formula Ib According to Route a$_2$

Reaction of an Acid of Formula IV with an Amine of Formula V 63) tert-Butyl 4-[5-[1-(tert-Butoxycarbonyl)-4-piperidyl]-3-({[2-({3-ethoxy-2-[(2-naphthylsulphonyl)amino]-3-oxopropyl}amino)-2-oxo-1-phenylethyl]amino}carbonyl)pentyl]tetrahydro-1(2H)-pyridinecarboxylate (Compound 91)
Ethyl 3-[(2-amino-2-phenylethanoyl)amino]-2-[(2-naphthylsulphonyl)amino]propanoate hydrochloride (1.7 g, 3 mmol) and diisopropylethylamine (0.8 g, 6.2 mmol) are added, at room temperature, to a solution of 4-[1-(tert-butoxycarbonyl)-4-piperidyl]-2-{2-[1-(tert-butoxycarbonyl)-4-piperidyl]ethyl}butanoyl fluoride (ref. synthesis B-1) (1.55 g, 3 mmol) in 50 ml of dichloromethane. After stirring for 3 hours, water is added. The organic phase is washed with water, dried over sodium sulphate and evaporated to give the crude product, which is purified by flash chromatography (20/1 dichloromethane/methanol) to give 1.2 g of a white solid.

Yield=44%; $^1$H-NMR (400 MHz, CDCl$_3$): δ 0.95 (m, 3H), 1.00 (m, 4H), 1.20 (m, 4H), 1.40 (m, 2H), 1.47 (s, 20H), 1.60 (m, 6H), 2.05 (m, 1H), 2.60 (bd, 4H), 3.50 (m, 1H), 3.58 (m, 1H), 3.65 (m, 1H), 3.80 (m, 2H), 3.99 (m, 2H), 5.45 (m, 1H), 5.75 (dd, 1H), 6.40 (dt, 1H), 6.85 (dd, 1H), 7.35 (m, 5H), 7.52 (m, 2H), 7.75 (d, 1H), 7.95 (m, 3H), 8.37 (d, 1H).

This method was used to prepare the following compound:

64) tert-Butyl 4-[5-[1-(tert-Butoxycarbonyl)-4-piperidyl]-3-({[2-({3-ethoxy-2-[(2-naphthylsulphonyl)amino]-3-oxopropyl}amino)-1-methyl-2-oxoethyl]amino}carbonyl)pentyl]tetrahydro-1(2H)-pyridinecarboxylate (Compound 92)
Starting Material: Ethyl 3-[(2-aminopropanoyl)amino]-2-[(2-naphthylsulphonyl)amino]propanoate hydrochloride Yield=71%; $^1$H-NMR (400 MHz, CDCl$_3$): δ 0.95 (t, 3H), 1.05 (m, 4H) 1.20 (m, 4H), 1.30 (d, 5H), 1.45 (s, 20H), 1.60 (m, 6H), 2.00 (m, 1H), 2.65 (bs, 4H), 3.50 (m, 1H), 3.70 (m, 1H), 3.88 (m, 2H), 4.08 (m, 4H), 4.50 (m, 1H), 6.10 (bd, 1H), 6.30 (d, 1H), 6.90 (t, 1H), 7.65 (m, 2H), 7.80 (d, 1H), 7.90 (d, 1H), 8.00 (d, 2H), 8.40 (s, 1H).

EXAMPLE 1

Ethyl 3-(1,3-benzodioxol-5-yl)-3-{[2-({4-(4-piperidyl)-2-[2-(4-piperidyl)ethyl]butanoyl}amino)acetyl]amino}propanoate Hydrochloride (CRL42725)

tert-Butyl 4-{3-{[1-(1,3-benzodioxol-5-yl)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (compound 9) (3.3 g, 4.35 mmol) is dissolved in 5 ml of dioxane and 10 ml of a 4N dioxane-hydrochloric acid solution are then added. The mixture is kept stirring at room temperature for 20 minutes and the dioxane is then separated out by settling. Ether is added and is separated out again by settling, and the resulting material is then evaporated to dryness. A white powder is obtained, which is dissolved in about 150 ml of water and then filtered and the filtrate is freeze-dried to give 2.4 g of a white solid.

Yield=87%; MS(ES): m/z 559 (M+H)$^+$; $^1$H-NMR (400 MHz, CD$_3$OD): δ 1.1 (m, 7H), 1.25 (m, 6H), 1.45 (m, 4H), 1.75 (m, 4H), 2.15 (m, 1H), 2.75 (m, 6H), 3.2 (m, 4H), 3.62 (m, 2H), 4.0 (q, 2H), 5.12 (q, 1H), 6.0 (s, 2H), 6.8 (dd, 2H), 6.95 (s, 1H), 8.1 (t, 1H), 8.45 (d, 1H), 8.8 (bs, 2H), 9.1 (bs, 2H).

The method described in Example 1 was used to prepare the following compounds:

EXAMPLE 2

Ethyl 3-[3-(2-ethoxy-2-oxoethoxy)phenyl]-3-{[2-{(4-(4-piperidyl)-2-[2-(4-piperidyl)ethyl]butanoyl}amino)acetyl]amino}propanoate Dihydrochloride (CRL42640)
Starting Material: Compound 13

Yield=92%; $^1$H-NMR (400 MHz, CD$_3$OD): δ 1.3 (t, 3H), 1.45 (m, 13H), 1.7 (m, 4H), 1.95 (m, 4H), 2.35 (m, 1H), 3.0 (m, 6H), 3.4 (m, 4H), 3.75 (s, 2H), 3.95 (s, 2H), 4.18 (q, 2H), 4.35 (q, 2H), 4.8 (s, 2H), 5.42 (t, 1H), 6.92 (d, 1H), 7.05 (m, 2H), 7.35 (t, 1H).

EXAMPLE 3

Ethyl 3-[3-(3-methoxyphenyl)]-3-{[2-({4-(4-piperidyl)-2-[2-(4-piperidyl)ethyl]butanoyl}amino)acetyl]amino}propanoate Dihydrochloride (CRL42661)
Starting Material: Compound 14

Yield=93%; $^1$H-NMR (400 MHz, CD$_3$OD): δ 1.3 (t, 3H), 1.5 (m, 17H), 2.0 (m, 4H), 2.33 (m, 1H), 3.0 (m, 6H), 3.4 (m, 4H), 3.9 (s, 3H), 3.98 (s, 2H), 4.2 (m, 2H), 5.42 (t, 1H), 6.95 (m, 2H), 7.05 (bs, 2H), 7.32 (t, 1H).

EXAMPLE 4

Ethyl (2S)-2-[(2-naphthylsulphonyl)amino]-3-{[2-({4-(4-piperidyl)-2-[2-(4-piperidyl)ethyl]butanoyl}amino)acetyl]amino}propanoate Dihydrochloride (CRL42968)
Starting Material: Compound 41

Yield=100%; [α]$_D$–16.5 (C=0.97, H$_2$O); MS(ES): m/2 644 (m+H)$^+$; $^1$H-NMR (400 MHz, DMSO-d$_6$): δ 0.85 (t, 3H), 1.1 (m, 4H), 1.25 (m, 6H), 1.45 (m, 4H), 1.7 (bd, 4H), 2.15 (m, 1H), 2.75 (bq, 4H), 3.2 (m, 5H) 3.3 (m, 1H), 3.6 (m, 4H), 3.95 (m, 1H), 7.7 (m, 2H), 7.8 (d, 1H), 8.0–8.2 (m, 5H), 8.4 (s, 1H), 8.55 (d, 1H), 8.85 (bd, 2H), 9.1 (bd, 2H).

EXAMPLE 5

3-(1,3-Benzodioxol-5-yl)-3-{[2-({4-(4-piperidyl)-2-[2-(4-piperidyl)ethyl]butanoyl}amino)acetyl]amino}-propanoic Acid Dihydrochloride (CRL42630)

1 g (23.8 mmol) of lithium hydroxide monohydrate is added to a solution of tert-butyl 4-{3-{[1-(1,3-benzodioxol-5-yl)-3-ethoxy-3-oxopropyl]amino}-2-oxoethyl)amino]carbonyl}-5-[1-(tert-butoxycarbonyl)-4-piperidyl]pentyl}tetrahydro-1(2H)-pyridinecarboxylate (compound 9) (7.6 g, 10 mmol) in 80 ml of tetrahydrofuran and 20 ml of water. After 4 hours at room temperature, the organic solvent is evaporated off. Water is added and the mixture is acidified to pH 2 and then extracted with ethyl acetate. The extracts are washed with water and dried over sodium sulphate. The filtrate is evaporated to give 6.3 g of acid.

The acid thus obtained is dissolved in 10 ml of ethyl acetate and 50 ml of a 3N ethyl acetate-hydrochloric acid solution are then added. Stirring is continued for 30 minutes at room temperature. The mixture is separated by settling. After addition of water (about 200 ml) followed by freeze-drying, 4.7 g of a white solid are obtained.

Yield=78%; MS(ES): m/z 531 (M+H)$^+$; $^1$H-NMR (400 MHz, CD$_3$OD): δ 1.5 (m, 12H), 1.95 (m, 4H), 2.25 (m, 1H), 2.75 (bs, 2H), 2.9 (m, 4H), 3.3 (m, 4H), 3.85 (s, 2H), 5.29 (bs, 1H), 5.95 (s, 2H), 6.8 (d, 2H), 6.85 (m, 3H).

The method described in Example 5 was used to prepare the following compounds:

EXAMPLE 6

3-(4-Isopropylphenyl)-3-{[2-({4-(4-piperidyl)-2-[2-(4-piperidyl)ethyl]butanoyl}amino)acetyl]amino}propanoic Acid Dihydrochloride (CRL42548)
Starting Material: Compound 10

Yield=98%; MS-Cl: m/z 529 (M+H)$^+$; $^1$H-NMR (400 MHz, CD$_3$OD): δ 1.5 (m, 16H), 1.65 (m, 4H), 1.95 (m, 5H), 2.35 (m, 1H), 3.0 (m, 6H), 3.4 (m, 4H), 3.95 (m, 2H), 5.4 (t, 1H), 7.25 (d, 2H), 7.38 (d, 2H).

EXAMPLE 7

3-(4-Methoxyphenyl)-3-{[2-({4-(4-piperidyl)-2-[2-(4-piperidyl)ethyl]butanoyl}amino)acetyl]amino}propanoic Acid Dihydrochloride (CRL42549)
Starting Material: Compound 11

Yield=98%; MS-Cl: m/z 517 (M+H)$^+$; $^1$H-NMR (400 MHz, CD$_3$OD): δ 1.5 (m, 14H), 1.95 (m, 4H), 2.16 (m, 1H), 2.9 (dq, 2H), 3.0 (m, 4H), 3.4 (m,4H), 3.85 (s, 3H), 3.95 (s,2H), 5.35 (t, 1H), 6.92 (d, 2H), 7.35 (d, 2H).

EXAMPLE 8

3-(3,4-Dimethoxyphenyl)-3-{[2-({4-(4-piperidyl)-2-[2-(4-piperidyl)ethyl]butanoyl}amino)acetyl]amino}propanoic Acid Dihydrochloride (CRL42590)

Starting Material: Compound 12

Yield=80%; MS-Cl: m/z: 547 (M+H)$^+$; $^1$H-NMR (400 MHz, CD$_3$OD): δ 1.15~1.65 (m, 14H), 1.8 (m, 4H), 2.25 (m, 1H), 2.85 (m, 6H), 3.3 (bs, 4H), 3.78 (s, 3H), 3.8 (s, 3H), 3.85 (m, 2H), 5.25 (t, 1H), 6.85 (d, 2H), 6.95 (d, 1H).

EXAMPLE 9

3-[(3-Carboxymethoxy)phenyl]-3-{[2-({4-(4-piperidyl)-2-[2-(4-piperidyl)ethyl]butanoyl}amino)acetyl]amino}-propanoic Acid Dihydrochloride (CRL42639)

Starting Material: Compound 13

Yield=79%; $^1$H-NMR (400 MHz, CD$_3$OD): δ 1.2~1.65 (m, 14H), 1.85 (m, 4H), 2.25 (m, 1H), 2.7~3.0 (m, 6H), 3.3 (bs, 4H), 3.78 (d, 2H), 4.68 (s, 2H), 5.3 (t, 1H), 6.82 (d, 1H), 6.95 (m, 2H), 7.25 (t, 1H).

EXAMPLE 10

3-(3-Methoxyphenyl)-3-{[2-({4-(4-piperidyl)-2-[2-(4-piperidyl)ethyl]butanoyl}amino)acetyl]amino}propanoic Acid Dihydrochloride (CRL42660)

Starting Material: Compound 14

Yield=81%; MS (ES): m/2 517 (M+H)$^+$; $^1$H-NMR (400 MHz, CD$_3$OD): δ 1.4 (m, 8H), 1.55 (m, 2H), 1.68 (m, 4H), 1.95 (bs, 4H), 2.3 (m, 1H), 2.9 (dd, 2H), 3.0 (m, 4H), 3.4 (m, 4H), 3.86 (s, 3H), 3.95 (s, 2H), 5.4 (m, 1H), 6.9 (m, 1H), 7.0 (m, 2H), 7.3 (t, 1H).

EXAMPLE 11

3-(2,3-Dihydro-1,4-benzodioxin-6-yl)-3-{[2-({4-(4-piperidyl)-2-[2-(4-piperidyl)ethyl]butanoyl}amino)acetyl]amino}propanoic Acid Dihydrochloride (CRL42718)

Starting Material: Compound 15

Yield=84%; MS(ES): m/z 545 (M+H)$^+$; $^1$H-NMR (400 MHz, DMSO-d$_6$+D$_2$O): δ 1.1 (m, 4H), 1.25 (m, 6H), 1.4 (m, 4H), 1.7 (m, 4H), 2.15 (m, 1H), 2.6 (t, 2H), 2.75 (m, 4H), 3.15 (bd, 4H), 3.7 (s, 2H), 4.05 (s, 4H), 5.05 (m, 1H), 6.72 (s, 1H), 6.78 (d, 2H)

EXAMPLE 12

3-(3-Pyridyl)-3-{[2-({4-(4-piperidyl)-2-[2-(4-piperidyl)ethyl]butanoyl}amino)acetyl]amino}propanoic Acid Trihydrochloride (CRL42722)

Starting Material: Compound 16

Yield=95%; MS(ES): m/z 488 (M+H)$^+$; $^1$H-NMR (400 MHz, DMSO-d$_6$): δ 1.1 (m, 4H), 1.25 (m, 6H), 1.4 (m, 4H), 1.65 (m, 4H), 2.15 (m, 1H), 2.85 (m, 4H), 2.9 (bd, 2H), 3.15 (m, 4H), 3.7 (m, 2H), 5.25 (m, 1H), 8.1 (bs, 1H), 8.25 (bs, 2H), 8.65 (d, 1H), 8.85 (bs, 1H), 8.95 (m, 4H), 9.2 (bs, 2H).

EXAMPLE 13

3-{[2-({4-(4-Piperidyl)-2-[2-(4-piperidyl)ethyl]butanoyl}amino)acetyl]amino}propanoic Acid Dihydrochloride (CRL43040)

Starting Material: Compound 17

Yield=100%; MS(ES): m/z 411 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.35 (t, 2H), 2.75 (bq, 4H), 3.15 (bd, 4H), 3.25 (q, 2H), 3.65 (d, 2H), 7.9 (t, 1H), 8.15 (t, 1H), 8.85 (bq, 2H), 9.15 (bd, 2H).

EXAMPLE 14

3-{[2-({4-(4-Piperidyl)-2-[2-(4-piperidyl)ethyl]butanoyl}amino)acetyl]amino}butanoic Acid Dihydrochloride (CRL43041)

Starting Material: Compound 18

Yield=100%; MS(ES): m/z 425 (M+H)$^+$; $^1$H-NMR (400 MHz, DMSO-d$_6$): δ 1.1 (d, 3H), 1.15 (m, 4H), 1.3 (m, 6H), 1.4 (m, 4H), 1.7 (bd, 4H), 2.15 (m, 1H), 2.25 (q, 1H), 2.45 (q, 1H), 2.75 (bq, 4H), 3.15 (bd, 4H), 3.6 (m, 2H), 4.05 (m, 1H), 7.85 (d, 1H), 8.1 (t, 1H), 8.8 (bq, 2H), 9.1 (bd, 2H).

EXAMPLE 15

5-Phenyl-3-{[2-({4-(4-piperidyl)-2-[2-(4-piperidyl)ethyl]butanoyl}amino)acetyl]amino}pentanoic Acid Dihydrochloride (CRL43042)

Starting Material: Compound 19

Yield=100%; MS(ES): m/z 515 (M+H)$^+$; $^1$H-NMR (400 MHz, DMSO-d$_6$): δ 1.15 (m, 4H), 1.25 (m, 6H), 1.45 (m, 4H), 1.75 (m, 6H), 2.2 (m, 1H), 2.4 (m, 2H), 2.5 (m, 1H), 2.65 (m, 1H), 2.75 (bq, 4H), 3.15 (bd, 4H), 3.7 (bq, 2H), 4.05 (m, 1H), 7.2 (m, 3H), 7.25 (t, 2H), 7.95 (d, 1H), 8.2 (t, 1H), 8.8 (bs, 2H), 9.15 (bd, 2H).

EXAMPLE 16

(3S)-4-(1-Adamantylamino)-4-oxo-3-{[2-({4-(4-piperidyl)-2-[2-(4-piperidyl)ethyl]butanoyl}amino)acetyl]amino}butanoic Acid Dihydrochloride (CRL42592)

Starting Material: Compound 20

Yield=94%; MS(ES): m/z 588 (M+H)$^+$; $^1$H-NMR (400 MHz, CD$_3$OD): δ 1.25 (m, 10H), 1.5 (m, 4H), 1.6 (s, 6H), 1.82 (bd, 4H), 1.9 (bs, 9H), 2.2 (m, 1H), 2.6 (m, 2H), 2.86 (bt, 4H), 3.25 (bd, 4H), 3.7 (d, 2H), 4.5 (t, 1H).

EXAMPLE 17

(3S)-4-{[2-(1H-Indol-4-yl)ethyl]amino}-4-oxo-3-{[2-({4-(4-piperidyl)-2-[2-( 4-piperidyl)ethyl]butanoyl}amino)acetyl]amino}butanoic Acid Dihydrochloride (CRL42678)

Starting Material: Compound 21

Yield=100%; MS(ES): m/z 597 (M+H)$^+$; $^1$H-NMR (400 MHz, DMSO-d$_6$): δ 1.15 (m, 4H), 1.3 (m, 6H), 1.45 (m, 4H), 1.75 (m, 4H), 2.2 (m, 1H), 2.55 (m, 2H), 2.75 (m, 6H), 3.15 (m, 4H), 3.35 (m, 2H),3.75 (bs, 2H), 4.6 (m, 1H), 6.98 (t, 1H), 7.08 (t, 1H), 7.16 (s, 1H), 7.35 (m, 1H), 7.55 (d, 1H), 8.1 (d, 1H), 8.2 (bs, 2H), 8.9 (bs, 2H), 9.2 (bs, 2H), 10.9 (bs, 1H).

EXAMPLE 18

(3S)-4-[(4-Methoxyphenyl)ethylamino]-4-oxo-3-{[2-({4-(4-piperidyl)-2-[2-(4-piperidyl)ethyl]butanoyl}amino)acetyl]amino}butanoic Acid Dihydrochloride (CRL42694)

Starting Material: Compound 22

Yield=97%; $^1$H-NMR (400 MHz, DMSO-d$_6$): δ 1.15 (m, 4H), 1.25 (m, 6H) 1.45 (m, 4H), 1.8 (bd, 4H), 2.15 (m, 1H), 2.5 (m, 2H), 2.65 (t, 2H), 2.75 (bd, 4H), 3.15 (bd, 6H), 3.7

(s, 5H), 4.55 (m, 1H), 6.85 (d, 2H), 7.15 (d, 2H), 8.1 (d, 1H), 8.15 (m, 2H), 8.95 (bd, 2H), 9.2 (bd, 2H).

EXAMPLE 19

(3S)-4-(3-Phenylpropylamino)-4-oxo-3-{[2-({4-(4-piperidyl)-2-[2-(4-piperidyl)ethyl]butanoyl}amino)acetyl]amino}butanoic Acid Dihydrochloride (CRL42719)

Starting Material: Compound 23

Yield=100%; MS(ES): m/z 572 (M+H)$^+$; $^1$H-NMR (400 MHz, DMSO-d$_6$): δ 1.15 (m, 4H), 1.3 (m, 6H), 1.4 (m, 4H), 1.7 (m, 6H), 2.15 (m, 1H), 2.55 (m, 4H), 2.75 (bd, 4H), 3.05 (m, 2H), 3.2 (bd, 4H), 3.7 (d, 2H), 4.55 (m, 1H), 7.2 (m, 5H), 8.15 (m, 3H), 8.9 (bs, 2H), 9.15 (bs, 2H).

EXAMPLE 20

(3S)-4-[(1,3-Benzodioxol-5-ylmethyl)amino]-4-oxo-3-{[2-({4-(4-piperidyl)-2-[2-(4-piperidyl)ethyl]butanoyl}amino)acetyl]amino}butanoic Acid Dihydrochloride (CRL42720)

Starting Material: Compound 24

Yield=90%; MS(ES): m/z 588 (M+H)$^+$; $^1$H-NMR (400 MHz, DMSO-d$_6$): δ 1.15 (m, 4H), 1.3 (m, 6H), 1.4 (m, 4H), 1.7 (m, 4H), 2.15 (m, 1H), 2.55 (bs, 2H), 2.75 (bd, 4H), 3.15 (d, 4H), 3.7 (d, 2H), 4.15 (d, 2H), 4.6 (m, 1H), 5.95 (s, 2H), 6.7 (d, 1H), 6.8 (s, 1H), 6.81 (d, 1H), 8.2 (m, 2H), 8.55 (t, 1H), 8.9 (bs, 2H), 9.15 (bs, 2H).

EXAMPLE 21

(3S)-4-[(3-Methoxyphenyl)amino]-4-oxo-3-{[2-({4-(4-piperidyl)-2-[2-(4-piperidyl)ethyl]butanoyl}amino)acetyl]amino}butanoic Acid Dihydrochloride (CRL42721)

Starting Material: Compound 25

Yield=100%; $^1$H-NMR (400 MHz, DMSO-d$_6$): δ 1.15 (m, 4H), 1.3 (m, 6H), 1.4 (m, 4H), 1.7 (m, 4H), 2.15 (m, 1H), 2.5 (m, 4H), 2.7 (m, 6H), 3.15 (m, 6H), 3.7 (s, 5H), 4.55 (m, 1H), 6.75 (s, 3H), 7.15 (t, 1H), 8.1 (d, 1H), 8.2 (bs, 2H), 8.9 (bs, 2H), 9.15 (bs, 2H).

EXAMPLE 22

(3S)-4-[(2-Hydroxy-1,1-dimethylethyl)amino]-4-oxo-3-{[2-({4-(4-piperidyl)-2-[2-(4-piperidyl)ethyl]butanoyl}amino)acetyl]amino}butanoic Acid Dihydrochloride (CRL42726)

Starting Material: Compound 26

Yield=100%; MS(ES): m/z 526 (M+H)$^+$; $^1$H-NMR (400 MHz, DMSO-d$_6$): δ 1.1 (m, 7H), 1.25 (m, 7H), 1.4 (m, 4H), 1.7 (m, 4H), 2.15 (m, 1H), 2.5 (m, 2H), 2.6 (m, 1H), 2.7 (bd, 4H), 3.1 (bd, 4H), 3.3 (q, 1H), 3.7 (bs, 2H), 4.05 (m, 1H), 4.45 (m, 1H), 4.65 (m, 1H), 8.05~8.5 (m, 3H), 8.9 (bs, 2H), 9.15 (bs, 2H).

EXAMPLE 23

(3S)-4-[(1-Isopropyl)-2-methylpropyl)amino]-4-oxo-3-{[2-({4-(4-piperidyl)-2-[2-(4-piperidyl)ethyl]butanoyl}amino)acetyl]amino}butanoic Acid Dihydrochloride (CRL42727)

Starting Material: Compound 27

Yield=89%; MS(ES): m/z 552 (M+H)$^+$; $^1$H-NMR (400 MHz, DMSO-d$_6$): δ 0.8 (m, 9H), 1.15 (m, 11H), 1.25 (m, 4H), 1.85 (m, 6H), 2.15 (m, 1H), 2.6 (m, 4H), 2.75 (m, 4H), 3.15 (m, 4H), 3.4 (m, 4H), 3.7 (m, 2H), 4.55 (m, 1H), 7.3 (d, 1H), 8.3 (m, 2H), 8.95 (bs, 2H), 9.2 (bs, 2H).

EXAMPLE 24

(2S)-2-{[(Benzyloxy)carboyl]amino}-3-{[2-({4-(4-piperidyl)-2-[2-(4-piperidyl)ethyl]butanoyl}amino)acetyl]amino}propanoic Acid Dihydrochloride (CRL42717)

Starting Material: Compound 29

Yield=97%; [α]$_D$ −8 (C=2.2, H$_2$O); MS(ES): m/z 560 (M+H)$^+$; $^1$H-NMR (400 MHz, DMSO-d$_6$): δ 1.15 (m, 4H), 1.3 (m, 6H), 1.45 (m, 4H), 1.75 (m, 4H), 2.15 (m, 1H), 2.8 (bd, 4H), 3.2 (bd, 4H), 3.3 (m, 1H), 3.5 (m, 1H), 3.7 (m, 2H), 4.1 (q, 1H), 5.05 (s, 2H), 7.35 (m, 4H), 7.55 (d, 1H), 8.05 (s, 1H), 8.15 (s, 1H), 8.9 (bs, 2H), 9.2 (bs, 2H).

EXAMPLE 25

2-[(1,3-Benzodioxol-5-ylcarbonyl)amino]-3-{[2-({4-(4-piperidyl)-2-[2-(4-piperidyl)ethyl]butanoyl}amino)acetyl]amino}propanoic Acid Dihydrochloride (CRL42731)

Starting Material: Compound 40

Yield=100%; MS(ES): m/z 574 (M+H)$^+$; $^1$H-NMR (400 MHz, DMSO-d$_6$): δ 1.15 (m, 4H), 1.25 (m, 6H), 1.45 (m, 4H), 1.75 (m, 4H), 2.2 (m, 1H), 2.75 (m, 4H), 3.2 (bd, 4H), 3.48 (m, 1H), 3.65 (m, 3H), 4.45 (m, 1H), 6.1 (s, 1H), 7.0 (d, 1H), 7.5 (s, 1H), 7.55 (d, 1H), 8.25 (bd, 2H), 8.65 (d, 1H), 8.95 (bs, 2H), 9.2 (bs, 2H).

EXAMPLE 26

2-[(Phenylsulphonyl)amino]-3-{[2-({4-(4-piperidyl)-2-[2-(4-piperidyl)ethyl]butanoyl}amino)acetyl]amino}propanoic Acid Dihydrochloride (CRL42724)

Starting Material: Compound 39

Yield=95%; MS-Cl: m/z 566 (M)$^+$; $^1$H-NMR (400 MHz, DMSO-d$_6$): δ 1.15 (m, 4H), 1.25 (m, 6H), 1.45 (m, 4H), 1.75 (m, 4H), 2.2 (m, 1H), 2.75 (m, 4H), 3.15 (bd, 4H), 3.25 (m, 1H), 3.5 (m, 2H), 3.8 (m, 1H), 7.6 (m, 3H), 7.8 (m, 2H), 8.05 (bd, 2H), 8.25 (d, 1H), 9.0 (bd, 2H), 9.25 (bd, 2H).

EXAMPLE 27

(2S)-2-[(2-Naphthylsulphonyl)amino]-3-{[2-({4-(4-piperidyl)-2-[2-(4-piperidyl)ethyl]butanoyl}amino)acetyl]amino}propanoic Acid Dihydrochloride (CRL42796)

Starting Material: Compound 41

Yield=91%; [α]$_D$ −10.1 (C=0.86, H$_2$O); MS(ES): m/z 616 (M+H)$^+$; $^1$H-NMR (400 MHz, DMSO-d$_6$): δ 1.1 (m, 4H), 1.25 (m, 6H), 1.45 (m, 4H), 1.7 (m, 4H), 2.15 (m, 1H), 2.75 (bd, 4H), 3.2 (bd, 5H), 3.4 (m, 1H), 3.55 (dq, 2H), 3.95 (q, 1H), 7.7 (m, 2H), 7.8 (d, 1H), 8.0 (m, 3H), 8.15 (dd, 2H), 8.35 (d, 1H), 8.4 (s, 1H), 8.7 (bs, 2H), 8.95 (bd, 2H).

EXAMPLE 28

2-{[(4-Propylphenyl)sulphonyl]amino}-3-{[2-({4-(4-piperidyl)-2-[2-(4-piperidyl)ethyl]butanoyl}amino)acetyl]amino}propanoic Acid Dihydrochloride (CRL42811)

Starting Material: Compound 42

Yield=94%; MS(ES): m/z 608 (M+H)$^+$; $^1$H-NMR (400 MHz, DMSO-d$_6$): δ 0.85 (t, 3H), 1.15 (m, 4H), 1.25 (m, 6H), 1.35 (m, 4H), 1.6 (q, 2H), 1.7 (m, 4H), 2.1 (m, 1H), 2.65 (t, 2H), 2.75 (m, 4H), 3.15 (m, 4H), 3.25 (m, 1H), 3.5 (m, 2H), 3.8 (m, 1H), 7.35 (d, 2H), 7.65 (d, 2H), 8.0 (t, 1H), 8.05 (m, 1H), 8.1 (d, 1H), 8.8 (bd, 2H), 9.05 (bd, 2H).

EXAMPLE 29

(3S)-4-oxo-4-(4-Benzylpiperidino)-3-{[2-({4-(4-piperidyl)-2-[2-(4-piperidyl)ethyl]butanoyl}amino)acetyl]amino}-butanoic Acid Dihydrochloride (CRL42591)

Starting Material: Compound 28

Yield=89%; MS(ES): m/z 612 (M+H)$^+$; $^1$H-NMR (400 MHz, CD$_3$OD): δ 1.3~1.6 (m, 12H), 1.9 (m, 6H), 2.26 (m, 1H), 2.55 (m, 4H), 2.92 (m, 6H), 3.45 (m, 6H), 3.85 (bd, 2H), 4 (bt, 1H), 4.4 (bd, 1H), 5.2 (bs, 1H), 7.15 (m, 3H), 7.25 (t, 2H).

EXAMPLE 30

2-[([1,1-Biphenyl]-4-ylsulphonyl)amino]-3-{[2-({4-(4-piperidyl)-2-[2-(4-piperidyl)ethyl]butanoyl}amino)acetyl]amino}propanoic Acid Dihydrochloride (CRL42913)

Starting Material: Compound 43

Yield=96%; MS(ES): m/z 642 (M+H)$^+$; $^1$H-NMR (400 MHz, DMSO-d$_6$): δ 1.15 (m, 4H), 1.30 (m, 6H), 1.45 (m, 4H), 1.75 (bd, 4H), 2.15 (m, 1H), 2.75 (bq, 4H), 3.20 (bd, 5H), 3.40 (m, 1H), 3.60 (dq, 2H), 3.9 (m, 1H), 7.45 (t, 1H), 7.5 (t, 2H), 7.75 (d, 2H), 7.85 (s, 4H), 8.05 (bs, 2H), 8.3 (d, 1H), 8.9 (bq, 2H), 9.15 (bd, 2H).

EXAMPLE 31

2-[(1-Naphthylsulphonyl)amino]-3-{[2-({4-(4-piperidyl)-2-[2-(4-piperidyl)ethyl]butanoyl}amino)acetyl]amino}propanoic Acid Dihydrochloride (CRL42914)

Starting Material: Compound 44

Yield=96%; MS (ES): m/z 616 (M+H)$^+$; $^1$H-NMR (400 MHz, DMSO-d$_6$): δ 1.05 (m, 4H), 1.2 (m, 6H), 1.4 (m, 4H), 1.7 (bd, 4H), 2.1 (m, 1H), 2.75 (bq, 4H), 3.15 (bd, 5H), 3.3 (m, 1H), 3.45 (dq, 2H), 3.85 (q, 1H), 7.65 (m, 3H), 7.95 (m, 2H), 8.05 (d, 1H), 8.1 (d, 1H), 8.2 (d, 1H), 8.5 (d, 1H), 8.65 (d, 1H), 8.75 (bs, 2H), 9.0 (bd, 2H).

EXAMPLE 32

2-({[4-(Methylsulphonyl)phenyl]sulphonyl}amino)-3-{[2-({4-(4-piperidyl)-2-[2-(4-piperidyl)ethyl]butanoyl}amino)acetyl]amino}propanoic Acid Dihydrochloride (CRL42969)

Starting Material: Compound 45

Yield=91%; MS(ES): m/z 644 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.1 (m, 1H), 2.7 (bq, 4H), 3.15 (bd, 5H), 3.25 (s, 3H), 3.35 (m, 1H), 3.55 (dq, 2H), 3.9 (m, 1H), 7.95~8.1 (m, 6H), 8.55 (d, 1H), 8.8 (bq, 2H), 9.05 (bd, 2H).

EXAMPLE 33

2-[(2-Thienylsulphonyl)amino]-3-{[2-({4-(4-piperidyl)-2-[2-(4-piperidyl)ethyl]butanoyl}amino)acetyl]amino}propanoic Acid Dihydrochloride (CRL42985)

Starting Material: Compound 46

Yield=97%; MS (ES): m/z 572 (M+H)$^+$; $^1$H-NMR (400 MHz, DMSO-d$_6$): δ 1.05 (m, 4H), 1.25 (m, 6H), 1.4 (m, 4H), 1.7 (bd, 4H), 2.15 (m, 1H), 2.7 (bq, 4H), 3.15 (bd, 5H), 3.35 (m, 1H), 3.55 (dq, 2H), 3.85 (q, 1H), 7.15 (dd, 1H), 7.5 (t, 1H), 7.9 (t, 1H), 8.0 (t, 1H), 8.05 (t, 1H), 8.4 (d, 1H), 8.8 (bq, 2H), 9.1 (bd, 2H).

EXAMPLE 34

2-([(4-Chlorophenyl)sulphonyl]amino)-3-{[2-({4-(4-piperidyl)-2-[2-(4-piperidyl)ethyl]butanoyl}amino)acetyl]amino}propanoic Acid Dihydrochloride (CRL42986)

Starting Material: Compound 47

Yield=92%; MS(ES): m/z 600 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.1 (m, 1H), 2.7 (bq, 4H), 3.15 (bd, 5H), 3.3 (m, 1H), 3.55 (dq, 2H), 3.8 (q, 1H), 7.6 (d, 2H), 7.75 (d, 2H), 8.05 (m, 2H), 8.35 (d, 1H), 8.85 (bq, 2H), 9.1 (bd, 2H).

EXAMPLE 35

2-{[(4-Fluorophenyl)sulphonyl]amino}-3-{[2-({4-(4-piperidyl)-2-[2-(4-piperidyl)ethyl]butanoyl}amino)acetyl]amino}propanoic Acid Dihydrochloride (CRL42999)

Starting Material: Compound 48

Yield=97%; MS(ES): m/z 584 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.75 (bq, 4H), 3.2 (bd, 5H), 3.35 (m, 1H), 3.6 (dq, 2H), 3.85 (m, 1H), 7.4 (t, 2H), 7.85 (dd, 2H), 8.05 (m, 2H), 8.30 (d, 1H), 8.8 (bq, 2H), 9.1 (bd, 2H).

EXAMPLE 36

(2S)-2-{[(6-Methoxy-2-naphthyl)sulphonyl]amino}-3-{[2-({4-(4-piperidyl)-2-[2-(4-piperidyl)ethyl]butanoyl}amino)acetyl]amino}propanoic Acid Dihydrochloride (CRL43000)

Starting Material: Compound 49

Yield=90%; [α]$_D$ −10 (C=1, H$_2$O); MS(ES): m/z 646 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.2 (bd, 5H), 3.35 (m, 1H), 3.6 (dq, 2H), 3.85 (m, 1H), 3.9 (s, 3H), 7.3 (d, 1H), 7.45 (s, 1H), 7.75 (d, 1H), 8.0 (d, 1H), 8.05 (m, 3H), 8.25 (d, 1H), 8.3 (s, 1H), 8.8 (bq, 2H), 9.1 (bd, 2H).

EXAMPLE 37

2-[(Mesitylsulphonyl)amino]-3-{[2-({4-(4-piperidyl)-2-[2-(4-piperidyl)ethyl]butanoyl}amino)acetyl]amino}propanoic Acid Dihydrochloride (CRL43031)

Starting Material: Compound 50

Yield=98%; MS(ES): m/z 608 (M+H)$^+$; $^1$H-NMR (400 MHz, DMSO-d$_6$): δ 1.15 (m, 4H), 1.3 (m, 6H), 1.4 (m, 4H), 1.7 (bd, 4H), 2.15 (m, 1H), 2.25 (s, 3H), 2.55 (s, 6H), 2.75 (bq, 4H), 3.2 (bd, 5H), 3.35 (m, 1H), 3.55 (dq, 2H), 3.8 (q, 1H), 7.0 (s, 2H), 8.0 (m, 3H), 8.85 (bq, 2H), 9.15 (bd, 2H).

EXAMPLE 38

(2S)-2-[(Butylsulphonyl)amino]-3-{[2-({4-(4-piperidyl)-2-[2-(4-piperidyl)ethyl]butanoyl}amino)acetyl]amino}propanoic Acid Dihydrochloride (CRL43032)

Starting Material: Compound 51

Yield=90%; [α]$_D$ −10.5 (C=1, H$_2$O); MS(ES): m/z 546 (M+H)$^+$; $^1$H-NMR (400 MHz, DMSO-d$_6$): δ 0.9 (t, 3H), 1.15 (m, 4H). 1.25~1.5 (m, 12H), 1.6~1.75 (m, 6H), 2.15 (m, 1H), 2.75 (bq, 4H), 3.0 (m, 2H), 3.15 (bd, 4H), 3.25 (m, 1H), 3.45 (m, 1H), 3.7 (dq, 2H), 3.95 (m, 1H), 7.6 (d, 1H), 8.05 (t, 1H), 8.15 (t, 1H), 8.85 (bq, 2H), 9.1 (bd, 2H).

EXAMPLE 39

2-{[(4-Methylphenyl)sulphonyl]amino}-3-{[2-({4-(4-piperidyl)-2-[2-(4-piperidyl)ethyl]butanoyl}amino)acetyl]amino}propanoic Acid Dihydrochloride (CRL43033)

Starting Material: Compound 52

Yield=87%; MS(ES): m/z 580 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.4 (s, 3H), 2.75 (bq, 4H), 3.15 (bd, 5H), 3.35 (m, 1H), 3.55 (dq, 2H), 3.8 (q, 1H), 7.35 (d, 2H), 7.7 (d, 2H), 8.0 (t, 1H), 8.05 (t, 1H), 8.1 (d, 1H), 8.8 (bq, 2H), 9.1 (bd, 2H).

EXAMPLE 40

2-{[(3-Methylphenyl)sulphonyl]amino}-3-{[2-({4-(4-piperidyl)-2-[2-(4-piperidyl)ethyl]butanoyl}amino)acetyl]amino}propanoic Acid Dihydrochloride (CRL43043)

Starting Material: Compound 53

Yield=99%; MS(ES): m/z 580 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.1 (m, 1H), 2.35 (s, 3H), 2.7 (bq, 4H), 3.15 (bd, 5H), 3.3 (m, 1H), 3.5 (dq, 2H), 3.8 (m, 1H), 7.4 (m, 2H), 7.55 (m, 2H), 8.0 (m, 2H), 8.15 (d, 1H), 8.8 (bq, 2H), 9.1 (bd, 2H).

EXAMPLE 41

2-[(Benzylsulphonyl)amino]-3-{[2-({4-(4-piperidyl)-2-[2-(4-piperidyl)ethyl]butanoyl}amino)acetyl]amino}propanoic Acid Dihydrochloride (CRL43055)

Starting Material: Compound 54

Yield=99%; MS(ES): m/z 580 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.75 (bq, 4H), 3.15 (bd, 4H), 3.35 (m, 1H), 3.45 (m, 1H), 3.7 (d, 2H), 3.95 (m, 1H), 4.35 (s, 2H), 7.35 (m, 5H), 7.6 (d, 1H), 8.1 (t, 1H), 8.15 (t, 1H), 8.85 (bq, 2H), 9.1 (bd, 2H).

EXAMPLE 42

2-({[(E)-2-Phenylethenyl]sulphonyl}amino)-3-{[2-({4-(4-piperidyl)-2-[2-(4-piperidyl)ethyl]butanoyl}amino)acetyl]amino}propanoic Acid Dihydrochloride (CRL43057)

Starting Material: Compound 55

Yield=100%; MS(ES): m/z 592 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.75 (bq, 4H), 3.15 (bd, 4H), 3.3 (m, 1H), 3.45 (m, 1H), 3.65 (m, 2H), 3.9 (m, 1H), 7.15 (d, 1H), 7.35 (d, 1H), 7.45 (m, 3H), 7.7 (m, 2H), 7.9 (d, 1H), 8.1 (m, 2H), 8.9 (bq, 2H), 9.15 (bd, 2H).

EXAMPLE 43

2-[(2-Phenethylsulphonyl)amino]-3-{[2-({4-(4-piperidyl)-2-[2-(4-piperidyl)ethyl]butanoyl}amino)acetyl]amino}propanoic Acid Dihydrochloride (CRL43056)

Starting Material: Compound 56

Yield=96%; MS(ES): m/z 594 (M+H)$^+$; $^1$H-NMR (400 MHz, DMSO-d$_6$): δ 1.15 (m, 4H), 1.3 (m, 6H), 1.45 (m, 4H), 1.7 (bd, 4H), 2.15 (m, 1H), 2.75 (bq, 4H), 2.95 (m, 1H), 3.1 (m, 1H), 3.15 (bd, 5H), 3.3 (m, 2H), 3.5 (m, 1H), 3.7 (m, 2H), 4.05 (m, 1H), 7.3 (m, 5H), 7.8 (m, 1H), 8.1 (m, 2H), 8.9 (bq, 2H), 9.15 (bd, 2H).

EXAMPLE 44

2-({[3-(Trifluoromethyl)phenyl]sulphonyl}amino)-3-{[2-({4-(4-piperidyl)-2-[2-(4-piperidyl)ethyl]butanoyl}amino)acetyl]amino}propanoic Acid Dihydrochloride (CRL43058)

Starting Material: Compound 57

Yield=93%; MS(ES): m/z 634 (M+H)$^+$; $^1$H-NMR (400 MHz, DMSO): δ 1.15 (m, 4H), 1.3 (m, 6H), 1.4 (m, 4H), 1.75 (bd, 4H), 2.15 (m, 1H), 2.75 (bq, 4H), 3.2 (bd, 5H), 3.4 (m, 1H), 3.6 (dq, 2H), 3.95 (m, 1H), 7.85 (t, 1H), 8.0 (d, 1H), 8.05 (m, 4H), 8.6 (t, 1H), 8.85 (bq, 2H), 9.1 (bd, 2H).

EXAMPLE 45

2-{[(3-Nitrophenyl)sulphonyl]amino}-3-{[2-({4-(4-piperidyl)-2-[2-(4-piperidyl)ethyl]butanoyl}amino)acetyl]amino}propanoic Acid Dihydrochloride (CRL43059)

Starting Material: Compound 58

Yield=90%; MS(ES): m/z 611 (M+H)$^+$; $^1$H-NMR (400 MHz, DMSO-d6): δ 1.15 (m, 4H), 1.3 (m, 6H), 1.45 (m, 4H), 1.75 (bd, 4H), 2.15 (m, 1H), 2.75 (bq, 4H), 3.2 (bd, 5H), 3.35 (m, 1H), 3.6 (dq, 2H), 3.9 (m, 1H), 7.9 (t, 1H), 8.1 (m, 2H), 8.2 (d, 1H), 8.45 (dd, 1H), 8.55 (s, 1H), 8.75 (d, 1H), 8.85 (bq, 2H), 9.1 (bd, 2H).

EXAMPLE 46

2-{[(4-Methoxyphenyl)sulphonyl]amino}-3-{[2-({4-(4-piperidyl)-2-[2-(4-piperidyl)ethyl]butanoyl}amino)acetyl]amino}propanoic Acid Dihydrochloride (CRL43060)

Starting Material: Compound 59

Yield=95%; MS(ES): m/z 596 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.75 (bq, 4H), 3.2 (bd, 5H), 3.35 (m, 1H), 3.6 (dq, 2H), 3.8 (m, 1H), 3.85 (s, 3H), 7.1 (d, 2H), 7.7 (d, 2H), 8.05 (m, 3H), 8.85 (bq, 2H), 9.1 (bd, 2H).

EXAMPLE 47

2-[(8-Quinolinylsulphonyl)amino]-3-{[2-({4-(4-piperidyl)-2-[2-(4-piperidyl)ethyl]butanoyl}amino)acetyl]amino}propanoic Acid Trihydrochloride (CRL43061)

Starting Material: Compound 60

Yield=100%; MS(ES): m/z 617 (M+H)$^+$; $^1$H-NMR (400 MHz, DMSO): δ 1.15 (m, 4H), 1.25 (m, 6H), 1.45 (m, 4H), 1.75 (bd, 4H), 2.15 (m, 1H), 2.75 (bq, 4H), 3.2 (bd, 4H), 3.35 (m, 2H), 3.55 (dq, 2H), 4.25 (m, 1H), 7.75 (m, 3H), 8.0 (t, 1H), 8.1 (t, 1H), 8.3 (m, 2H), 8.6 (d, 1H), 8.9 (bd, 2H), 9.1 (m, 1H), 9, (bd, 2H).

EXAMPLE 48

2-{[(3,5-Dimethyl-4-isoxazolyl)sulphonyl]amino}-3-{[2-({4-(4-piperidyl)-2-[2-(4-piperidyl)ethyl]butanoyl}amino)acetyl]amino}propanoic Acid Dihydrochloride (CRL43068)

Starting Material: Compound 61

Yield=85%; MS(ES): m/z 585 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.35 (s, 3H), 2.6 (s, 3H), 2.75 (bq, 4H), 3.2 (bd, 5H), 3.4 (m, 1H), 3.6 (dq, 2H), 3.85 (m, 1H), 8.1 (t, 2H), 8.6 (d, 1H), 8.9 (bq, 2H), 9.15 (bd, 2H).

EXAMPLE 49

2-({[5-(Dimethylamino)-1-naphthyl)sulphonyl}amino)-3-{[2-({4-(4-piperidyl)-2-[2-(4-piperidyl)ethyl]butanoyl}amino)acetyl]amino}propanoic Acid Trihydrochloride (CRL43069)

Starting Material: Compound 62

Yield 100%; MS(ES): m/z 659 (M+H)$^+$; $^1$H-NMR (400 MHz, DMSO-d$_6$): δ 1.1 (m, 4H), 1.3 (m, 6H), 1.45 (m, 4H), 1.7 (bd, 4H), 2.15 (m, 1H), 2.75 (bq, 4H), 3.2 (bs, 11H), 3.35 (m, 2H), 3.5 (q, 1H), 3.9 (q, 1H), 7.75 (q, 2H), 7.9 (bs, 1H), 7.95 (t, 1H), 8.05 (t, 1H), 8.7 (dd, 2H), 8.9 (bq, 2H), 9.15 (bd, 2H).

EXAMPLE 50

2-({[2-(Acetylamino)-4-methyl-1,3-thiazol-5-yl]sulphonyl}amino)-3-{[2-({4-(4-piperidyl)-2-[2-(4-piperidyl)ethyl]butanoyl}amino)acetyl]amino}propanoic Acid Dihydrochloride (CRL43070)

Starting Material: Compound 63

Yield 100%; MS(ES): m/z 644 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.2 (s, 3H), 2.45 (s, 3H), 2.8 (bq, 4H), 3.2 (bd, 5H), 3.4 (m, 1H), 3.6 (dq, 2H), 3.9 (m, 1H), 8.1 (m, 2H), 8.45 (d, 1H), 8.85 (bq, 2H), 9.1 (bd, 2H).

EXAMPLE 51

2-{[(3-Chloropropyl)sulphonyl]amino}-3-{[2-({4-(4-piperidyl)-2-[2-(4-piperidyl)ethyl]butanoyl}amino)acetyl]amino}propanoic Acid Dihydrochloride (CRL43078)

Starting Material: Compound 64

Yield=100%; MS(ES): m/z 566 (M+H)$^+$; $^1$H-NMR (400 MHz, DMSO-d$_6$): δ 1.15 (m, 4H), 1.25 (m, 6H), 1.45 (m, 4H), 1.75 (bd, 4H), 2.15 (m, 3H), 2.75 (bq, 4H), 3.15 (m, 7H), 3.45 (m, 1H), 3.65 (m, 2H), 3.75 (t, 2H), 3.95 (m, 1H), 7.75 (d, 1H), 8.1 (m, 2H), 8.8 (bq, 2H), 9.1 (bd, 2H).

EXAMPLE 52

2-([(4-Methoxy-1-naphthyl)sulphonyl]amino)-3-{[2-({4-(4-piperidyl)-2-[2-( 4-piperidyl)ethyl]butanoyl}amino)acetyl]amino}propanoic Acid Dihydrochloride (CRL43079)

Starting Material: Compound 65

Yield=95%; MS(ES): m/z 646 (M+H)$^+$; $^1$H-NMR (400 MHz, DMSO-d$_6$): δ 1.15 (m, 4H), 1.3 (m, 6H), 1.45 (m, 4H), 1.7 (bd, 4H), 2.1 (m, 1H), 2.75 (bq, 4H), 3.15 (bd, 5H), 3.3 (m, 1H), 3.45 (dq, 2H), 3.8 (m, 1H), 4.05 (s, 3H), 7.1 (d, 2H), 7.60 (t, 1H), 7.7 (t, 1H), 7.9 (t, 1H), 8.0 (t, 1H), 8.1 (d, 2H), 8.3 (d, 1H), 8.35 (d, 1H), 8.6 (d, 1H), 8.85 (bs, 2H), 9.1 (bs, 2H).

EXAMPLE 53

2-{[(6,7-Dimethoxy-2-naphthyl)sulphonyl]amino}-3-{[2-({4-(4-piperidyl)-2-[2-(4-piperidyl)ethyl]butanoyl}amino)acetyl]amino}propanoic Acid Dihydrochloride (CRL43080)

Starting Material: Compound 66

Yield=86%; MS(ES): m/z 676 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.75 (bq, 4H), 3.15 (bd, 5H), 3.35 (m, 1H), 3.55 (dq, 2H), 3.85 (m, 1H), 3.9 (s, 3H), 3.92 (s, 3H), 7.45 (s, 1H), 7.55 (s, 1H), 7.65 (d, 1H), 7.9 (d, 1H), 8.05 (bs, 2H), 8.20 (d, 1H), 8.25 (s, 1H), 8.85 (bq, 2H), 9.1 (bd, 2H).

EXAMPLE 54

2-{[(2,4-Dimethyl-1,3-thiazol-5-yl)sulphonyl]amino}-3-{[2-({4-(4-piperidyl)-2-[2-(4-piperidyl)ethyl]butanoyl}amino)acetyl]amino}propanoic Acid Dihydrochloride (CRL43120)

Starting Material: Compound 67

Yield=94%; MS(ES): m/z 601 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.5 (s, 3H), 2.65 (s, 3H), 2.75 (bq, 4H), 3.2 (bd, 5H), 3.4 (m, 1H), 3.6 (dq, 2H), 3.9 (q, 1H), 8.1 (m, 2H), 8.7 (d, 1H), 8.9 (bq, 2H), 9.15 (bd, 2H).

EXAMPLE 55

2-{[(3,5-Dimethyl-1H-pyrazol-4-yl)sulphonyl]amino}-3-{[2-({4-(4-piperidyl)-2-[2-(4-piperidyl)ethyl]butanoyl}amino)acetyl]amino}propanoic Acid Dihydrochloride (CRL43121)

Starting Material: Compound 68

Yield=98%; MS(ES): m/z 584 (M+H)$^+$; $^1$H-NMR (400 MHz, DMSO-d$_6$): δ 1.15 (m, 4H), 1.25 (m, 6H), 1.4 (m, 4H), 1.7 (bd, 4H), 2.15 (m, 1H), 2.3 (s, 6H), 2.75 (bq, 4H), 3.15 (bd, 5H), 3.3 (m, 1H), 3.6 (dq, 2H), 3.75 (m, 1H), 7.8 (d, 1H), 8.0 (bt, 1H), 8.1 (bt, 1H), 8.8 (bq, 2H), 9.15 (bd, 2H).

EXAMPLE 56

2-[(3-Pyridylsulphonyl)amino]3-{[2-({4-(4-piperidyl)-2-[2-(4-piperidyl)ethyl]butanoyl}amino)acetyl]amino}propanoic Acid Trihydrochloride (CRL43122)

Starting Material: Compound 69

Yield=69%; MS(ES): m/z 567 (M+H)$^+$; $^1$H-NMR (400 MHz, DMSO): δ 1.1 (m, 4H), 1.3 (m, 6H), 1.45 (m, 4H), 1.7 (bd, 4H), 2.15 (m, 1H), 2.75 (bd, 4H), 3.15 (bd, 5H), 3.45 (m, 1H), 3.55 (dq, 2H), 3.95 (q, 1H), 7.75 (t, 1H), 8.15 (bd, 2H), 8.35 (d, 1H), 8.75 (d, 1H), 8.9 (bd, 1H), 8.95 (bd, 2H), 9.0 (s, 1H), 9.2 (bd, 2H).

EXAMPLE 57

2-[(1,3-Benzodioxol-5-ylsulphonyl)amino]-3-{[2-({4-(4-piperidyl)-2-[2-(4-piperidyl)ethyl]butanoyl}amino)acetyl]amino}propanoic Acid Dihydrochloride (CRL43123)

Starting Material: Compound 70

Yield=91%; MS(ES): m/z 610 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.15 (bd, 5H), 3.3 (m, 1H), 3.6 (dq, 2H), 3.75 (m, 1H), 6.1 (d, 2H), 7.0 (d, 1H), 7.2 (s, 1H), 7.25 (d, 1H), 8.05 (m, 3H), 8.75 (bd, 2H), 9.05 (bd, 2H).

EXAMPLE 58

2-[(2,3-Dihydro-1,4-benzodioxin-6-ylsulphonyl)amino]-3-{[2-({4-(4-piperidyl)-2-[2-(4-piperidyl)ethyl]butanoyl}amino)acetyl]amino}propanoic Acid Dihydrochloride (CRL43124)

Starting Material: Compound 71

Yield=91%; MS(ES): m/z 624 (M+H)$^+$; $^1$H-NMR (400 MHz, DMSO-d$_6$): δ 1.1 (m, 4H), 1.3 (m, 6H), 1.4 (m, 4H), 1.7 (bd, 4H), 2.15 (m, 1H), 2.75 (bq, 4H), 3.15 (bd, 5H), 3.3

(m, 1H), 3.6 (dq, 2H), 3.75 (q, 1H), 4.3 (dd, 2H), 6.95 (d, 1H), 7.2 (d, 1H), 7.22 (s, 1H), 8.05 (m, 3H), 8.85 (bq, 2H), 9.1 (bd, 2H).

EXAMPLE 59

2-[(1-Benzothiophen-2-ylsulphonyl)amino]-3-{[2-({4-(4-piperidyl)-2-[2-(4-piperidyl)ethyl]butanoyl}amino)acetyl]amino}propanoic Acid Dihydrochloride (CRL43125)

Starting Material: Compound 72

Yield=99%; MS(ES): m/z 622 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.15 (bd, 5H), 3.3 (m, 1H), 3.45 (dq, 2H), 3.9 (q, 1H), 7.5 (m, 2H), 8.0 (m, 2H), 8.1 (d, 1H), 8.2 (d, 1H), 8.45 (s, 1H), 8.55 (d, 1H), 8.9 (bq, 2H), 9.15 (bd, 2H).

EXAMPLE 60

2-{[(2,5-Dimethyl-3-furyl)sulphonyl]amino}-3-{[2-({4-(4-piperidyl)-2-[2-( 4-piperidyl)ethyl]butanoyl}amino)acetyl]amino}propanoic Acid Dihydrochloride (CRL43131)

Starting Material: Compound 73

Yield=99%; MS(ES): m/z 584 (M+H)$^+$; $^1$H-NMR (400 MHz, DMSO-d$_6$): δ 1.15 (m, 4H), 1.3 (m, 6H), 1.45 (m, 4H), 1.75 (bd, 4H), 2.15 (m, 1H), 2.25 (s, 3H), 2.4 (s, 3H), 2.75 (bq, 4H), 3.2 (bd, 5H), 3.35 (m, 1H), 3.6 (dq, 2H), 3.8 (m, 1H), 6.2 (s, 1H), 8.05 (m, 3H), 8.8 (bq, 2H), 9.05 (bd, 2H).

EXAMPLE 61

2-{[(4-Cyclohexylphenyl)sulphonyl]amino)-3-{[2-({4-(4-piperidyl)-2-[2-(4-piperidyl)ethyl]butanoyl}amino)acetyl]amino}propanoic Acid Dihydrochloride (CRL43132)

Starting Material: Compound 74

Yield=94%; MS(ES): m/z 648 (M+H)$^+$; $^1$H-NMR (400 MHz, DMSO-d$_6$): δ 1.0~1.5 (m, 20H), 1.75 (m, 8H), 2.15 (m, 1H), 2.6 (bt, 1H), 2.75 (bq, 4H), 3.2 (bd, 5H), 3.35 (m, 1H), 3.5 (dq, 2H), 3.85 (q, 1H), 7.15 (d, 2H), 7.7 (d, 2H), 7.98 (t, 1H), 8.04 (t, 1H), 8.1 (d, 1H), 8.8 (bq, 2H), 9.05 (bd, 2H).

EXAMPLE 62

2-{[(4-Fluoro-1-naphthyl)sulphonyl]amino}-3-{[2-({4-(4-piperidyl)-2-[2-(4-piperidyl)ethyl]butanoyl}amino)acetyl]amino}propanoic Acid Dihydrochloride (CRL43133)

Starting Material: Compound 75

Yield=90%; MS(ES): m/z 634 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.1 (m, 1H), 2.75 (bq, 4H), 3.15 (bd, 5H), 3.3 (m, 1H), 3.5 (dq, 2H), 3.85 (q, 1H), 7.5 (t, 1H), 7.8 (m, 2H), 8.0 (m, 2H), 8.15 (m, 2H), 8.65 (d, 1H), 8.7 (d, 1H), 8.8 (bq, 2H), 9.05 (bd, 2H).

EXAMPLE 63

2-{[(4-Chloro-1-naphthyl)sulphonyl]amino}-3-{[2-({4-(4-piperidyl)-2-[2-(4-piperidyl)ethyl]butanoyl}amino)acetyl]amino}propanoic Acid Dihydrochloride (CRL43134)

Starting Material: Compound 76

Yield=91%; MS(ES): m/z 650 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.15 (bd, 5H), 3.35 (m, 1H), 3.5 (dq, 2H), 3.85 (q, 1H), 7.85 (m, 3H), 8.0 (m, 2H), 8.1 (t, 1H), 8.75 (m, 4H), 9.0 (bd, 2H).

EXAMPLE 64

2-[(2,3-Dihydro-1-benzofuran-5-ylsulphonyl)amino]-3-{[2-({4-(4-piperidyl)-2-[2-(4-piperidyl)ethyl]butanoyl}amino)acetyl]amino}propanoic Acid Dihydrochloride (CRL43142)

Starting Material: Compound 77

Yield=94%; MS(ES): m/z 608 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.2 (m, 7H), 3.3 (m, 1H), 3.6 (dq, 2H), 3.75 (q, 1H), 4.65 (t, 2H), 6.9 (d, 1H), 7.52 (d, 1H), 7.6 (s, 1H), 8.0 (d, 1H), 8.05 (t, 1H), 8.10 (t, 1H), 8.85 (bq, 2H), 9.1 (bd, 2H).

EXAMPLE 65

2-({[4-(2-Thienyl)phenyl]sulphonyl}amino) 3-{[2-({4-(4-piperidyl)-2-[2-(4-piperidyl)ethyl]butanoyl}amino)acetyl]amino}propanoic Acid Dihydrochloride (CRL43143)

Starting Material: Compound 78

Yield=66%; MS(ES): m/z 648 (M+H)$^+$; $^1$H-NMR (400 MHz, DMSO-d$_6$): δ 1.1 (m, 4H), 1.25 (m, 6H), 1.35 (m, 4H), 1.7 (bd, 4H), 2.15 (m, 1H), 2.75 (bq, 4H), 3.1 (bd, 5H), 3.3 (m, 1H), 3.55 (dq, 2H), 3.85 (m, 1H), 7.2 (bs, 1H), 7.65 (bs, 2H), 7.75 (dd, 4H), 8.05 (m, 2H), 8.30 (d, 1H), 8.85 (bq, 2H), 9.1 (bd, 2H).

EXAMPLE 66

2-({[2-(2-Thienyl)phenyl]sulphonyl}amino) 3-{[2-({4-(4-piperidyl)-2-[2-(4-piperidyl)ethyl]butanoyl}amino)acetyl]amino}propanoic Acid Dihydrochloride (CRL43144)

Starting Material: Compound 79

Yield=97%; MS(ES): m/z 648 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.1 (m, 1H), 2.75 (bq, 4H), 3.15 (bd, 4H), 3.3 (m, 1H), 3.35 (m, 1H), 3.65 (dq, 2H), 3.8 (q, 1H), 7.1 (t, 1H), 7.35 (d, 1H), 7.5 (d, 2H), 7.6 (m, 3H), 7.85 (d, 1H), 8.0 (d, 1H), 8.1 (m, 2H), 8.8 (bq, 2H), 9.1 (bd, 2H).

EXAMPLE 67

2-({[4-(2-Furyl)phenyl]sulphonyl}amino)-3-{[2-({4-(4-piperidyl)-2-[2-(4-piperidyl)ethyl]butanoyl}amino)acetyl]amino}propanoic Acid Dihydrochloride (CRL43146)

Starting Material: Compound 80

Yield=84%; MS(ES): m/z 632 (M+H)$^+$; $^1$H-NMR (400 MHz, DMSO-d$_6$): δ 1.1 (m, 4H), 1.25 (m, 6H), 1.45 (m, 4H), 1.75 (bd, 4H), 2.15 (m, 1H), 2.75 (bq, 4H), 3.2 (bd, 5H), 3.35 (m, 1H), 3.6 (dq, 2H), 3.85 (q, 1H), 6.7 (d, 1H), 7.2 (d, 1H), 7.8 (d, 2H), 7.85 (m, 3H), 8.1 (m, 2H), 8.25 (d, 1H), 8.85 (bq, 2H), 9.1 (bd, 2H).

EXAMPLE 68

2-[(1-Benzofuran-2-ylsulphonyl)amino]-3-{[2-({4-(4-piperidyl)-2-[2-(4-piperidyl)ethyl]butanoyl}amino)acetyl]amino}propanoic Acid Dihydrochloride (CRL43147)

Starting Material: Compound 81

Yield=94%; MS(ES): m/z 606 (M+H)$^+$; $^1$H-NMR (400 MHz, DMSO-d$_6$): δ 1.1 (m, 4H), 1.2 (m, 6H), 1.4 (m, 4H), 1.75 (bd, 4H), 2.15 (m, 1H), 2.75 (bq, 4H), 3.15 (bd, 5H), 3.5 (m, 1H), 3.55 (dq, 2H), 4.05 (m, 1H), 7.4 (t, 1H), 7.5 (m, 2H), 7.7 (d, 1H), 7.75 (d, 1H), 8.05 (bs, 2H), 8.8 (bd, 3H), 9.1 (bd, 2H).

EXAMPLE 69

2-{[(2-Naphthylmethyl)sulphonyl]amino}-3-{[2-({4-(4-piperidyl)-2-[2-(4-piperidyl)ethyl]butanoyl}amino)acetyl]amino}propanoic Acid Dihydrochloride (CRL43158)

Starting Material: Compound 82

Yield=88%; MS(ES): m/z 630 (M+H)$^+$; $^1$H-NMR (400 MHz, DMSO-d$_6$): δ 1.2 (m, 7H), 1.45 (m, 4H), 1.7 (m, 4H), 2.15 (m, 1H), 2.75 (bq, 4H), 3.1 (bd, 4H), 3.4 (m, 2H), 3.7 (d, 2H), 4.05 (q, 1H), 4.5 (s, 2H), 7.55 (d, 2H), 7.65 (d, 1H), 7.95 (m, 4H), 8.05 (t, 1H), 8.1 (t, 1H), 8.6 (bq, 2H), 8.85 (bd, 2H).

EXAMPLE 70

2-[(2,3-Dihydro-1H-inden-5-ylsulphonyl)amino]-3-{[2-({4-(4-piperidyl)-2-[2-(4-piperidyl)ethyl]butanoyl}amino)acetyl]amino}propanoic Acid Dihydrochloride (CRL43159)

Starting Material: Compound 83

Yield=94%; MS(ES): m/z 606 (M+H)$^+$; $^1$H-NMR (400 MHz, DMSO-d$_6$): δ 1.15 (m, 4H), 1.25 (m, 6H), 1.4 (m, 4H), 1.7 (bd, 4H), 2.05 (m, 2H), 2.15 (m, 1H), 2.75 (bq, 4H), 2.9 (t, 4H), 3.15 (bd, 5H), 3.35 (m, 1H), 3.5 (dq, 2H), 3.8 (q, 1H), 7.4 (d, 1H), 7.55 (d, 1H), 7.6 (s, 1H), 8.0 (m, 4H), 8.75 (bq, 2H), 9.0 (bd, 2H).

EXAMPLE 71

2-{[(5-Phenyl-2-thienyl))sulphonyl]amino}-3-{[2-({4-(4-piperidyl)-2-[2-(4-piperidyl)ethyl]butanoyl}amino)acetyl]amino}propanoic Acid Dihydrochloride (CRL43160)

Starting Material: Compound 84

Yield=97%; MS(ES): m/z 648 (M+H)$^+$; $^1$H-NMR (400 MHz, DMSO-d$_6$): δ 1.1 (m, 4H), 1.25 (m, 6H), 1.4 (m, 4H), 1.7 (bd, 4H), 2.15 (m, 1H), 2.75 (bq, 4H), 3.15 (bd, 5H), 3.4 (m, 1H), 3.6 (dq, 2H), 3.95 (q, 1H), 7.4 (m, 3H), 7.55 (s, 2H), 7.75 (d, 2H), 8.05 (bs, 2H), 8.55 (d, 1H), 8.85 (bq, 2H), 9.1 (bd, 2H).

EXAMPLE 72

2-[(5,6,7,8-Tetrahydro-2-naphthalenylsulphonyl)amino]3-{[2-({4-(4-piperidyl)-2-[2-(4-piperidyl)ethyl]butanoyl}amino)acetyl]amino}propanoic Acid Dihydrochloride (CRL43161)

Starting Material: Compound 85

Yield=97%; MS(ES): m/z 620 (M+H)$^+$; $^1$H-NMR (400 MHz, DMSO-d$_6$): δ 1.1 (m, 4H), 1.25 (m, 6H), 1.45 (m, 4H), 1.75 (bs, 8H), 2.15 (m, 1H), 2.75 (bs, 8H), 3.2 (bd, 5H), 3.35 (m, 1H), 3.55 (dq, 2H), 3.8 (q, 1H), 7.2 (d, 1H), 7.45 (d, 2H), 8.0 (m, 3H), 8.75 (bq, 2H), 9.0 (bd, 2H).

EXAMPLE 73

2-{[(E)-1-Pentenylsulphonyl]amino}-3-{[2-({4-(4-piperidyl)-2-[2-(4-piperidyl)ethyl]butanoyl}amino)acetyl]amino}propanoic Acid Dihydrochloride (CRL43176)

Starting Material: Compound 86

Yield=93%; MS(ES): m/z 558 (M+H)$^+$; $^1$H-NMR (400 MHz, DMSO-d$_6$): δ 0.9 (t, 3H), 1.15 (m, 4H), 1.25 (m, 6H), 1.45 (m, 6H), 1.75 (bd, 4H), 2.15 (q, 3H), 2.75 (bq, 4H), 3.2 (bd, 5H), 3.4~3.75 (m, 4H), 6.3 (d, 1H), 6.5 (dt, 1H), 7.65 (d, 1H), 8.0 (t, 1H), 8.1 (t, 1H), 8.75 (bq, 2H), 9.0 (bd, 2H).

EXAMPLE 74

2-[(Cyclohexylsulphonyl)amino]-3-{[2-({4-(4-piperidyl)-2-[2-(4-piperidyl)ethyl]butanoyl}amino)acetyl]amino}propanoic Acid Dihydrochloride (CRL43190)

Starting Material: Compound 30

Yield=93%; MS(ES): m/z 572 (M+H)$^+$; $^1$H-NMR (400 MHz, DMSO-d$_6$): δ 1.05~1.40 (m, 15H), 1.45 (m, 4H), 1.60 (bd, 1H), 1.75 (m, 6H), 2.0~2.25 (m, 3H), 2.75 (bq, 4H), 2.85 (m, 1H), 3.15 (bd, 4H), 3.25 (m, 1H), 3.45 (m, 1H), 3.70 (m, 2H), 3.95 (m, 1H), 7.5 (d, 1H), 8.10 (m, 2H), 8.85 (bd, 2H), 9.1 (bd, 2H).

EXAMPLE 75

2-[(Isopropylsulphonyl)amino]-3-{[2-({4-(4-piperidyl)-2-[2-(4-piperidyl)ethyl]butanoyl}amino)acetyl]amino}propanoic Acid Dihydrochloride (CRL43191)

Starting Material: Compound 31

Yield=97%; MS(ES): m/z 532 (M+H)$^+$; $^1$H-NMR (400 MHz, DMSO-d$_6$): δ 1.1~1.35 (m, 16H), 1.45 (m, 4H), 1.75 (bd, 4H), 2.15 (m, 1H), 2.75 (bq, 4H), 3.1 (m, 1H), 3.2 (bd, 4H), 3.3 (m, 1H), 3.45 (m, 1H), 3.70 (m, 2H), 3.95 (m, 1H), 7.5 (d, 1H), 8.05 (t, 1H), 8.10 (t, 1H), 8.8 (bq, 2H), 9.05 (bd, 2H).

EXAMPLE 76

2-[(1,3-Benzothiazol-2-ylsulphonyl)amino]-3-{[2-({4-(4-piperidyl)-2-[2-(4-piperidyl)ethyl]butanoyl}amino)acetyl]amino}propanoic Acid Dihydrochloride (CRL43194)

Starting Material: Compound 32

Yield=98%; MS (ES): m/z 623 (M+H)$^+$; $^1$H-NMR (400 MHz, DMSO-d$_6$): δ 1.15 (m, 4H), 1.30 (m, 6H), 1.45 (m, 4H), 1.70 (m, 4H), 2.15 (m, 1H), 2.75 (bd, 4H), 3.15 (bd, 4H), 3.25 (m, 1H), 3.60 (m, 3H), 4.20 (q, 1H), 7.70 (m, 2H), 8.05 (bd, 2H), 8.20 (d, 1H), 8.30 (d, 1H), 8.90 (bd, 2H), 9.20 (bd, 2H), 9.25 (d, 1H).

EXAMPLE 77

(2S)-2-{[(Benzyloxy)carbonyl]amino}-3-{[3-({4-(4-piperidyl)-2-[2-(4-piperidyl)ethyl]butanoyl}amino)propanoyl]amino}propanoic Acid Dihydrochloride (CRL43022)

Starting Material: Compound 33

Yield=88%; MS(ES): m/z 574 (M+H)$^+$; $^1$H-NMR (400 MHz, DMSO-d$_6$): δ 1.10 (m, 4H), 1.25 (m, 6H), 1.45 (m, 4H), 1.75 (bd, 4H), 2.05 (m, 1H), 2.25 (t, 2H), 2.75 (bq, 4H), 3.15 (bd, 6H), 3.3 (m, 1H), 3.45 (m, 1H), 4.1 (m, 1H), 5.05 (s, 2H), 7.35 (s, 5H), 7.55 (d, 1H), 7.95 (t, 1H), 8.15 (t, 1H), 8.95 (bq, 2H), 9.15 (bs, 2H).

EXAMPLE 78

2-[(2-Naphthylsulphonyl)amino]-3-{[3-({4-(4-piperidyl)-2-[2-(4-piperidyl)ethyl]butanoyl}amino)propanoyl]amino}propanoic Acid Dihydrochloride (CRL43021)

Starting Material: Compound 87

Yield=84%; MS(ES): m/z 630 (M+H)$^+$; $^1$H-NMR (400 MHz, DMSO-d$_6$): δ 1.05 (m, 4H), 1.25 (m, 6H), 1.40 (m, 4H), 1.75 (bd, 4H), 2.05 (m, 3H), 2.75 (bq, 4H), 3.15 (m, 7H), 3.3 (m, 1H), 3.95 (q, 1H), 7.7 (m, 2H), 7.8 (d, 1H), 7.9 (t, 1H), 8.05 (d, 1H), 8.1 (m, 3H), 8.3 (d, 1H), 8.4 (s, 1H), 9.0 (bd, 2H), 9.25 (bd, 2H).

EXAMPLE 79

2-[(Phenylsulphonyl)amino]-3-{[3-({4-(4-piperidyl)-2-[2-(4-piperidyl)ethyl]butanoyl}amino)propanoyl]amino}propanoic Acid Dihydrochloride (CRL43145)

Starting Material: Compound 88

Yield=86%; MS(ES): m/z 580 (M+H)$^+$; $^1$H-NMR (400 MHz, DMSO-d$_6$): δ 1.05 (m, 4H), 1.25 (m, 6H), 1.40 (m, 4H), 1.70 (bd, 4H), 2.05 (m, 1H), 2.1 (q, 2H), 2.75 (bq, 4H), 3.15 (m, 1H), 3.30 (m, 1H), 3.85 (q, 1H), 7.55 (m, 3H), 7.8 (d, 1H), 7.9 (t, 1H), 8.1 (t, 1H), 8.25 (d, 1H), 8.9 (bd, 2H), 9.10 (bd, 2H).

EXAMPLE 80

2-[(2-Naphthylsulphonyl)amino]-3-{[3-({4-(4-piperidyl)-2-[2-(4-piperidyl)ethyl]butanoyl}amino)butanoyl]amino}propanoic Acid Dihydrochloride (CRL43195)

Starting Material: Compound 34

Yield=100%; MS(ES): m/z 644 (M+H)$^+$; $^1$H-NMR (400 MHz, DMSO-d$_6$): δ 0.9 (d, 3H), 1.05 (m, 4H), 1.25 (m, 6H), 1.40 (m, 4H), 1.70 (m, 4H), 1.95 (m, 1H), 2.00 (m, 1H), 2.15 (dd, 1H), 2.75 (bq, 4H), 3.05 (m, 1H), 3.20 (bd, 4H), 3.35 (m, 1H), 3.95 (m, 2H), 7.70 (m, 3H), 7.8 (d, 1H), 8.05 (m, 2H), 8.10 (dd, 2H), 8.30 (d, 1H), 8.35 (s, 1H), 8.75 (bt, 2H), 9.0 (bd, 2H).

EXAMPLE 81

2-[(2-Naphthylsulphonyl)amino]-3-{[3-phenyl-3-({4-(4-piperidyl)-2-[2-(4-piperidyl)ethyl]butanoyl}amino)butanoyl]amino}propanoic Acid Dihydrochloride (CRL43196)

Starting Material: Compound 35

Yield=87%; MS(ES): m/z 706 (M+H)$^+$; $^1$H-NMR (400 MHz, DMSO-d$_6$): δ 1.00 (m, 4H), 1.25 (m, 6H), 1.40 (m, 4H), 1.65 (dd, 4H), 2.10 (m, 1H), 2.40 (m, 1H), 2.75 (bd, 4H), 3.00 (m, 1H), 3.10 (bs, 4H), 3.25 (m, 1H), 3.75 (m, 1H), 3.98 (q, 1H), 7.25 (m, 5H), 7.65 (m, 2H), 7.80 (m, 1H), 8.00 (t, 1H), 8.10 (m, 3H), 8.30 (t, 1H), 8.45 (d, 1H), 8.48 (m, 1H), 8.75 (bt, 2H), 9.05 (bt, 2H).

EXAMPLE 82

2-[(2-Naphthylsulphonyl)amino]-3-{[((3R)-1-{4-(4-piperidyl)-2-[2-(4-piperidyl)ethyl]butanoyl}hexahydro-3-pyridyl)carbonyl]amino}propanoic Acid Dihydrochloride (CRL43197)

Starting Material: Compound 36

Yield=93%; MS(ES): m/z 670 (M+H)$^+$; $^1$H-NMR (400 MHz, DMSO-d$_6$): δ 1.05 (m, 4H), 1.25~1.60 (m, 14H), 1.73 (bt, 4H), 2.00 (m, 1H), 2.45 (m, 1H), 2.75 (m, 6H), 3.10 (m, 5H), 3.35 (m, 1H), 3.90 (m, 2H), 4.30 (dd, 1H), 7.70 (m, 2H), 7.80 (m, 1H), 8.00 (m, 1H), 8.10 (m, 3H), 8.40 (m, 2H), 8.85~9.25 (m, 4H).

EXAMPLE 83

2-[(2-Naphthylsulphonyl)amino]-3-{[2-phenyl-2-({4-(4-piperidyl)-2-[2-(4-piperidyl)ethyl]butanoyl}amino)ethanoyl]amino}propanoic Acid Dihydrochloride (CRL43210)

Starting Material: Compound 91

Yield=94%; $^1$H-NMR (400 MHz, DMSO-d$_6$): δ 0.95 (m, 1H), 1.0~1.5 (m, 13H), 1.60 (bd, 2H), 1.70 (bd, 2H), 2.35 (m, 1H), 2.70 (m, 4H), 3.15 (m, 5H), 3.25 (m, 1H), 3.95 (m, 1H), 5.50 (t, 1H), 7.25 (m, 5H), 7.65 (m, 2H), 7.80 (d, 1H), 8.01 (d, 1H), 8.10 (m, 1H), 8.15 (d, 1H), 8.30 (q, 1H), 8.40 (s, 1H), 8.50 (t, 2H), 8.75 (bs, 2H), 9.00 (bs, 2H).

EXAMPLE 84

2-[(2-Naphthylsulphonyl)amino]-3-([2-({4-(4-piperidyl)-2-[2-(4-piperidyl)ethyl]butanoyl}amino)propanoyl]amino}propanoic Acid Dihydrochloride (CRL43214)

Starting Material: Compound 92

Yield=89%; $^1$H-NMR (400 MHz, DMSO-d$_6$): δ 1.00 (d, 3H), 1.08 (m, 4H), 1.27 (m, 6H), 1.42 (m, 4H), 1.70 (bd, 4H), 2.12 (m, 1H), 2.73 (bd, 4H), 3.00 (m, 1H), 3.20 (bs, 4H), 3.48 (m, 1H), 3.89 (q, 1H), 4.18 (t, 1H), 7.65 (m, 2H), 7.82 (d, 1H), 7.95 (d, 1H), 8.06 (d, 2H), 8.15 (q, 2H), 8.35 (d, 1H), 8.40 (s, 1H), 8.85 (m, 2H), 9.10 (bs, 2H).

EXAMPLE 85

2-({[(7,7-Dimethyl-2-oxobicyclo[2.2.1]hept-1-yl)methyl]sulphonyl}amino)-3-{[2-({4-(4-piperidyl)-2-[2-(4-piperidyl)ethyl]butanoyl}amino)acetyl]amino}propanoic Acid Dihydrochloride (CRL43215)

Starting Material: Compound 89

Yield=90%; $^1$H-NMR (400 MHz, DMSO-d$_6$): δ 0.80 (s, 3H), 1.05 (s, 3H), 1.15 (m, 4H), 1.30 (m, 6H), 1.45 (m, 6H), 1.75 (bd, 4H), 1.90 (m, 2H), 2.05 (t, 1H), 2.15 (m, 1H), 2.35 (m, 2H), 2.75 (bq, 4H), 3.05 (d, 1H), 3.20 (bd, 4H), 3.30 (m, 1H), 3.35 (d, 1H), 3.50 (m, 1H), 3.70 (dq, 2H), 4.00 (m, 1H), 7.65 (d, 1H), 8.10 (m, 2H), 8.85 (bs, 2H), 9.10 (bs, 2H).

EXAMPLE 86

(2R)-2-[(2-naphthylsulphonyl)amino]-3-{[2-({4-(4-piperidyl)-2-[2-(4-piperidyl)ethyl]butanoyl}amino)acetyl]amino}propanoic Acid Dihydrochloride (CRL42956)

(2R)-3-({2-[(4-[1-(tert-Butoxycarbonyl)-4-piperidyl]-2-{2-[1-(tert-butoxycarbonyl)-4-piperidyl]ethyl}butanoyl)amino]acetyl}amino)-2-[(2-naphthylsulphonyl)amino]propanoic acid (compound 90) (8 g, 9.8 mmol) is dissolved in 30 ml of ethyl acetate and 150 ml of 3N ethyl acetate-hydrochloric acid are then added at room temperature. Stirring is continued for 40 minutes and ethyl acetate is then added. A white powder is obtained by drying under vacuum. After addition of 500 ml of water, 5.92 g of a white solid are obtained by freeze-drying.

Yield=98%; [α]$_D$ +9.5 (C=0.15, H$_2$O); MS(ES): m/z 616 (M+H)$^+$; $^1$H-NMR (400 MHz, DMSO-d$_6$): δ 1.1 (m, 4H), 1.25 (m, 6H), 1.45 (m, 4H), 1.7 (m, 4H), 2.15 (m, 1H), 2.75 (bd, 4H), 3.2 (bd, 5H), 3.4 (m, 1H), 3.55 (dq, 2H), 3.95 (q, 1H), 7.7 (m, 2H), 7.8 (d, 1H), 8.0 (m, 3H), 8.15 (dd, 2H), 8.35 (d, 1H), 8.4 (s, 1H), 8.7 (bs, 2H), 8.95 (bd, 2H).

A study of the inhibitory activity of the compounds of formula I on platelet aggregation was carried out in vitro, i.e.

by direct contact of solutions of variable concentrations of the compounds with platelets freshly separated from a sample of total blood, taken under standardized conditions, from laboratory animals (guinea pigs) and from healthy human subjects who have not received any substances or drugs that might interfere with blood clotting. The anti-platelet-aggregating activity was also studied ex vivo/vitro, i.e. after administration of the substances claimed to guinea pigs to measure the intensity and duration of the anti-aggregating action induced by the fraction of the test product absorbed and circulating in the blood.

1. In Vitro Pharmacological Studies

1.1. Studies on Guinea Pig Platelets

Blood is taken by intracardiac puncture from male Dunkin-Hartley guinea pigs (weighing about 330 g), at a rate of 4.5 ml per 0.5 ml of trisodium citrate (concentration of the aqueous solution: 1.55%) in order to prevent all trace of clotting. The platelet-rich plasma (PRP) is obtained by centrifuging the tubes of total blood for 15 minutes at 150 g.

The PRPs are collected as "pools". The platelets contained in these pools are counted using a Coulter ZM haematology automatic device: if necessary, a dilution is carried out in order for the platelet concentration in the plasma to be between 200,000 and 400,000 platelets/mm$^3$. Simultaneously, other samples of these pools serve to prepare the platelet-poor plasma (PPP) by centrifugation at 1500 g for 15 minutes.

The kinetic study of the platelet aggregation is carried out by adding a collagen solution (1 $\mu$g/ml) to a volume of PRP, using a Chrono-log Corporation aggregometer (490-D$_1$ or 560 VS) which uses an optical detection of the appearance of the thrombus.

The determination of the 50% inhibitory concentration (IC$_{50}$) is carried out by adding a given volume of solvent (control reference) and increasing concentrations: $1.5 \times 10^{-8}$ M, $7 \times 10^{-8}$ M, $1.5 \times 10^{-7}$ M, $3 \times 10^{-7}$ M, $7 \times 10^{-7}$ M, $1.5 \times 10^{-6}$ M and $7 \times 10^{-5}$ M, of the compounds to samples of the pools of PRP. The measurements of the aggregation inhibition are carried out after 3 minutes of contact at 37° C. with agitation.

1.2 Study on Human Patelets

Venous blood is taken from a group of ten healthy human subjects of the same age, by puncture into a vein of the fold of the elbow and is collected in a glass tube containing aqueous 0.129 M sodium citrate solution (1 volume of citrate solution per 9 volumes of blood). Each tube is then centrifuged a first time at 20° C. and 100 g for 15 minutes in order to obtain the platelet-rich plasma (PRP); after removing this PRP, the tube is again centrifuged at 2000 g for 15 minutes in order this time to remove the platelet-poor plasma (PPP).

For each identified sample of PRP, the platelets are counted using a Coulter ZM counter. Each sample is then used to study the variation in inhibition of the platelet aggregation triggered by the addition of a Chromo-par Reagent collagen glucose solution from Coultronics (used at a concentration of 5 $\mu$g/ml) as a function of the addition of increasing concentrations of each compound in a range covering the interval $10^{-8}$ M→$10^{-5}$ M, (example of concentrations: $10^{-8}$ M, $5 \times 10^{-7}$ M, $3 \times 10^{-7}$ M, $10^{-7}$ M, $8 \times 10^{-6}$ M, $6 \times 10^{-6}$ M, $4 \times 10^{-6}$ M, $2 \times 10^{-6}$ M, $10^{-6}$ M, $5 \times 10^{-5}$ M, $10^{-5}$ M). Beforehand, for each compound, an aqueous $10^{-3}$ M solution is prepared. A control test intended to check the possible effect of the solvents (reference value) on the platelet aggregation is introduced into each measurement series, and is measured after 3 minutes of contact at 37° C. with agitation.

From the percentages of inhibition of the platelet aggregation measured for each concentration of each compound, the 50% inhibitory concentration (IC$_{50}$) is calculated.

2. Ex Vivo/Vitro Pharmacological Study in Guinea Pigs

Evaluation of the anti-platelet-aggregating activity of the compounds is carried out in the same guinea pigs as those mentioned above (Dunkin-Hartley strain). The administration of each product in a range of doses from 150 mg/kg to 10 mg/kg and of each vehicle (5 ml/kg) is carried out via the gastric route (g.r.) 1 h, 2 h, 4 h, 6 h, 8 h or 12 h before blood is taken from the fasted guinea pigs. The allocation of the treatments to the animals is random.

The blood is taken and then treated under the same conditions as those described above for the in vitro studies.

The results of the inhibition of the platelet aggregation obtained for each test concentration make it possible to calculate the IC$_{50}$ concentration of each test product and the kinetics of the inhibitory effect and its duration of action.

The results are collated in the following table:

| | | | | % of g.r. inhibition guinea pig ex vivo | | | |
|---|---|---|---|---|---|---|---|
| | | IC$_{50}$ (M) in vitro | | d = 150 mg/kg | | d = 10 mg/kg | |
| Examples | Compound CRL | Guinea pig | Man | 1 h | 2 h | 1 h | 2 h |
| 6 | 42548 | $1.4 \times 10^{-5}$ | $2.7 \times 10^{-6}$ | −9 | −4 | — | — |
| 7 | 42549 | $10^{-5}$ | | −39 | 0 | — | — |
| 8 | 42590 | $3.5 \times 10^{-5}$ | $1.6 \times 10^{-6}$ | −10 | −31 | — | — |
| 29 | 42591 | $1.3 \times 10^{-5}$ | $10^{-5}$ | −35 | −23 | | |
| 16 | 42592 | $3.5 \times 10^{-6}$ | $8.5 \times 10^{-7}$ | −54 | −47 | −5 | — |
| 5 | 42630 | $2.0 \times 10^{-6}$ | $2.8 \times 10^{-7}$ | −63 | −66 | −15 | — |
| 9 | 42639 | $5.0 \times 10^{-6}$ | — | −53 | −5 | | |
| 10 | 42660 | $1.3 \times 10^{-5}$ | $9.2 \times 10^{-7}$ | −14 | −18 | — | — |
| 17 | 42678 | $7.4 \times 10^{-6}$ | $6.0 \times 10^{-6}$ | −19 | — | — | — |
| 12 | 42722 | $9.8 \times 10^{-7}$ | $1.5 \times 10^{-6}$ | −74 | −68 | — | — |
| 26 | 42724 | $4.4 \times 10^{-7}$ | $5.3 \times 10^{-7}$ | −77 | −68 | −41 | −20 |
| 25 | 42731 | $2.9 \times 10^{-5}$ | — | −33 | −48 | — | — |
| 27 | 42796 | $1.9 \times 10^{-8}$ | $4.4 \times 10^{-8}$ | — | — | — | — |
| 28 | 42811 | $1.5 \times 10^{-6}$ | $1.1 \times 10^{-6}$ | −73 | −75 | −18 | — |
| 30 | 42913 | $1.2 \times 10^{-7}$ | $1.4 \times 10^{-7}$ | — | −72 | −67 | — |
| 31 | 42914 | $4.4 \times 10^{-8}$ | $5.8 \times 10^{-7}$ | — | — | −81 | −81 |
| 32 | 42969 | $1.2 \times 10^{-5}$ | | — | — | −8 | −8 |
| 33 | 42985 | $7.1 \times 10^{-7}$ | $4.9 \times 10^{-7}$ | — | — | −14 | −5 |
| 34 | 42986 | $5.0 \times 10^{-7}$ | $8.9 \times 10^{-7}$ | — | — | −19 | −8 |
| 35 | 42999 | $1.8 \times 10^{-8}$ | $1.3 \times 10^{-8}$ | — | — | −5 | 0 |
| 36 | 43000 | $4.1 \times 10^{-8}$ | $7.2 \times 10^{-8}$ | — | — | −63 | −69 |
| 78 | 43021 | $4.6 \times 10^{-8}$ | $10^{-7}$ | — | — | −65 | −73 |
| 37 | 43031 | $1.4 \times 10^{-7}$ | $1.3 \times 10^{-7}$ | — | — | −9 | −16 |
| 39 | 43033 | $2.5 \times 10^{-7}$ | — | — | — | −32 | −10 |
| 15 | 43042 | $4.3 \times 10^{-6}$ | $1.5 \times 10^{-7}$ | −84 | −26 | — | — |
| 40 | 43043 | $4.0 \times 10^{-7}$ | — | — | — | −32 | −10 |
| 41 | 43055 | $8.6 \times 10^{-6}$ | — | — | — | 13 | 1 |
| 46 | 43056 | $1.2 \times 10^{-6}$ | — | — | — | −15 | −4 |
| 42 | 43057 | $4.2 \times 10^{-7}$ | | — | — | −14 | −26 |
| 44 | 43058 | $5.1 \times 10^{-7}$ | | — | — | −22 | −35 |
| 45 | 43059 | $5.0 \times 10^{-7}$ | — | — | — | −36 | −51 |
| 46 | 43060 | $3.8 \times 10^{-7}$ | — | — | — | −18 | −31 |
| 47 | 43061 | $1.9 \times 10^{-6}$ | — | — | — | −4 | −17 |
| 48 | 43068 | $4.2 \times 10^{-7}$ | — | — | — | −61 | −15 |
| 49 | 43069 | $4.9 \times 10^{-8}$ | $5.6 \times 10^{-8}$ | — | — | −69 | −68 |
| 50 | 43070 | $3.3 \times 10^{-6}$ | — | — | — | −22 | −39 |
| 51 | 43078 | $1.1 \times 10^{-5}$ | — | — | — | 4 | −21 |

-continued

| Examples | Compound CRL | IC$_{50}$ (M) in vitro Guinea pig | IC$_{50}$ (M) in vitro Man | % of g.r. inhibition guinea pig ex vivo d = 150 mg/kg 1 h | d = 150 mg/kg 2 h | d = 10 mg/kg 1 h | d = 10 mg/kg 2 h |
|---|---|---|---|---|---|---|---|
| 52 | 43079 | $3.5 \times 10^{-8}$ | $9.3 \times 10^{-8}$ | — | — | −58 | −30 |
| 53 | 43080 | $3.7 \times 10^{-8}$ | $7.3 \times 10^{-8}$ | — | — | −73 | −9 |
| 54 | 43120 | $1.3 \times 10^{-6}$ | — | — | −40 | −15 | |
| 55 | 43121 | $3.5 \times 10^{-6}$ | — | — | — | −21 | −17 |
| 56 | 43122 | $2.3 \times 10^{-7}$ | — | — | — | −61 | −50 |
| 57 | 43123 | $8.3 \times 10^{-7}$ | — | — | — | −38 | −24 |
| 58 | 43124 | $5.9 \times 10^{-7}$ | — | — | — | −36 | −21 |
| 59 | 43125 | $6.6 \times 10^{-8}$ | $1.5 \times 10^{-7}$ | — | — | −66 | −34 |
| 60 | 43131 | $6.6 \times 10^{-7}$ | — | — | −53 | −32 | |
| 61 | 43132 | $1.4 \times 10^{-6}$ | — | — | — | −21 | −9 |
| 62 | 43133 | $9.5 \times 10^{-8}$ | — | — | — | −69 | −33 |
| 63 | 43134 | $5.3 \times 10^{-8}$ | $10^{-6}$ | — | — | −69 | −50 |
| 64 | 43142 | $3.7 \times 10^{-7}$ | — | — | — | −65 | −5 |
| 65 | 43143 | $2.0 \times 10^{-7}$ | — | — | — | −65 | −12 |
| 66 | 43144 | $3.5 \times 10^{-7}$ | — | — | — | −18 | 0 |
| 68 | 43147 | $1.8 \times 10^{-7}$ | — | — | — | −72 | −71 |
| 69 | 43158 | $1.9 \times 10^{-6}$ | — | — | — | −69 | −3 |
| 70 | 43159 | $4.0 \times 10^{-7}$ | — | — | — | −32 | −34 |
| 71 | 43160 | $6.3 \times 10^{-8}$ | $1.9 \times 10^{-7}$ | — | — | −72 | −70 |
| 72 | 43161 | $3.4 \times 10^{-7}$ | — | — | — | −60 | −67 |

—: data not available.

A subject of the present invention is thus also pharmaceutical compositions comprising an effective amount of a compound of formula (I) or of a salt thereof with pharmaceutically acceptable acids.

A subject of the invention is, more particularly, compounds for inhibiting the aggregation of blood platelets, comprising an effective amount of one of these compounds.

A subject of the invention is also
- a process for inhibiting the binding of fibrinogen to blood platelets in a mammal, comprising the administration to this mammal of an effective amount of one of these compounds,
- a process for treating a thrombus in a patient, comprising the administration to this patient of an effective amount of one of these compounds,
- a process for preventing the thrombotic risk in a patient, comprising the administration to this patient of an effective amount of one of these compounds.

The compounds of formula (I) can be used, in particular, in the following fields:

i) Acute prevention of the arterial thrombotic risk in the course of heart surgery (coronary bypass) or interventional cardiology (transluminal percutaneous angioplasty, endarterectomy, insertion of a stent): in these situations, the compounds are added to the recognized preventive treatment of the arterial thrombotic risk; oral administration of acetylsalicylic acid starting before the intervention (150 to 500 mg/j orally) and then continues as follows; intravenous infusion of non-fractionated heparin starting during the intervention and then continuing for 48 to 96 hours. The administration of the compound of formula I can then be carried out either orally (0.5 to 1.5 mg/kg) at the same time as the administration of aspirin, or by intravenous infusion (0.25 to 1 mg/kg/24 h) combined or not combined with a bolus. After the 48$^{th}$ hour, if the treatment was administered intravenously, it will be relayed by the oral administration (0.25 to 10 mg/kg in two dosage intakes with an interval of 12 hours) in order to facilitate the hospitalization care and then the ambulatory treatment.

(ii) Secondary prophylaxis of the arterial thrombotic risk in patients liable to exhibit episodes of unstable angina or a myocardial infarction: in these situations, the large bioavailability of the compounds claimed, i.e. the possibility of rapidly obtaining circulating concentrations that are effective since they are capable of inhibiting the binding of fibrinogen to platelets, makes it possible to use the medicinal products claimed orally during the period in which the patients show this risk of arterial thrombosis. In these situations, these compounds may be administered advantageously at a rate of 1 to 3 oral doses per day, by virtue of their high bioavailability and their long duration of action, the dose being chosen in the range 0.5–10 mg/kg.

The pharmaceutical compositions which comprise one of the active principles described in the present patent application incorporate the active substance either in the form of base or in the form of a pharmaceutically acceptable salt, or alternatively in the form of a prodrug comprising an ester function, this function then being released in vivo after oral administration. These pharmaceutical compositions incorporate the manufacturing adjuvants and vehicles that are known to those skilled in the art. The latter are chosen from the range of pharmaceutical tools recognized by the Pharmacopoeias. Examples which may be mentioned for the preparation of pharmaceutical forms intended for the oral route are: starch, magnesium stearate, talc, gelatin, agar, pectin, lactose, polyethylene glycols, etc. The pharmaceutical forms which can be used will be chosen from the following possibilities: splittable or non-splittable tablets, gel capsules, lozenges, granules, powders. According to the characteristics of the pathology to be treated and the morphology of each patient, the daily oral dose will be between 0.02 and 50 mg/kg/day taken in 1 to 3 doses uniformly spaced in order to maintain an effective level of occupation of the platelet GpIIb/IIIa receptors. Via the intravenous route, the pharmaceutical forms intended for the acute phase of the treatment are designed so as to allow an individual dosage adaptation on the basis of the inhibition of platelet aggregation which is most efficient as a function of the immediate evolution of the operation follow-ups. In this context, the lyophilizate and the ready-to-use solution for infusion make it possible to individually modify the dosage within the dosage range 0.01 mg/kg/day-20 mg/kg/day.

What is claimed is:

1. Compounds of formula:

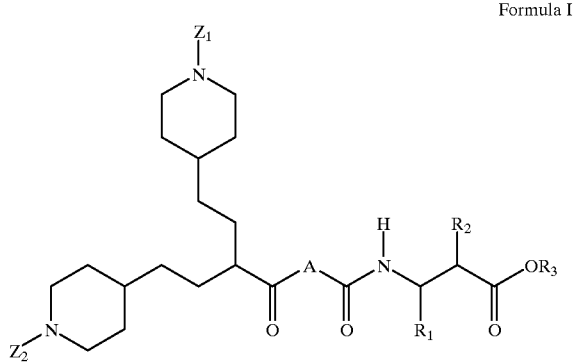

Formula I in which:

i) either R$_1$ is chosen from:

C$_1$–C$_4$ alkyl, C$_3$–C$_{12}$ mono- or bicyclic cycloalkyl, C$_2$–C$_4$ alkenyl or C$_2$–C$_4$ alkynyl groups, these groups optionally being substituted with groups chosen from halogens and the hydroxyl group;

mono-, bi- or tricyclic C$_6$–C$_{14}$ aryl groups, heteroaryl groups chosen from pyridyl, thienyl, furyl, quinolyl, benzodioxanyl, benzodioxolyl, benzothienyl, benzofuryl and pyrazinyl groups;

phenyl (C$_1$–C$_4$)alkyl and naphthyl(C$_1$–C$_4$)alkyl groups optionally substituted on the aryl nucleus, the aryl and heteroaryl groups possibly being substituted with one or more groups chosen independently from halogens, C$_1$–C$_4$ alkyl, trifluoromethyl, C$_1$–C$_4$ alkylthio, C$_1$–C$_4$ alkylsulfonyl, C$_1$–C$_4$ alkyloxy, nitro and groups —COOR, —CH$_2$COOR or —O—CH$_2$—COOR, R being a C$_1$–C$_4$ alkyl group, the groups of formula:

$$-\underset{\underset{O}{\parallel}}{C}-NR_4R'_4$$

in which R$_4$ and R'$_4$ are chosen from C$_1$–C$_8$ alkyl and mono- or polycyclic C$_3$–C$_{12}$ cycloalkyl groups, these groups optionally being substituted with groups chosen from halogens and the hydroxyl group, R'$_4$ also possibly being hydrogen, or alternatively R$_4$ and R'$_4$ together form a tetramethylene or pentamethylene group, these last two groups themselves possibly being substituted, in particular with a C$_6$–C$_{14}$ aryl or (C$_6$–C$_{14}$)aryl (C$_1$–C$_4$)alkyl residue;

the groups of formula:

$$-\underset{\underset{O}{\parallel}}{C}-NH-(CH_2)_{\overline{m}}-R_5$$

in which m=1 to 4 and R$_5$ is chosen from phenyl, methoxyphenyl, indolyl, benzodioxolyl, benzodioxanyl, benzothienyl and benzofuryl groups, and R$_2$ is hydrogen, ii) or R$_1$ is hydrogen and R$_2$ is chosen from the groups of formula:

—NH—CO—R$_6$,

R$_6$ being chosen from C$_1$–C$_4$ alkoxy, C$_3$–C$_7$ cycloalkoxy, benzyloxy, methoxyphenyl, dimethoxyphenyl, benzodioxolyl and benzodioxanyl groups, and the groups of formula:

—NH—SO$_2$—R$_7$,

R$_7$ being chosen from:

C$_1$–C$_5$ alkyl groups optionally substituted with one or more groups chosen from halogens, hydroxyl groups and the trifluoromethyl group;

C$_2$–C$_5$ alkenyl groups;

mono- or bicyclic C$_3$–C$_{12}$ cycloalkyl groups;

mono-, bi- or tricyclic C$_6$–C$_{14}$ aryl groups;

heteroaryl groups chosen from pyridyl, furyl, thienyl, quinolyl, benzodioxanyl, benzodioxolyl, isoxazolyl, benzodioxinyl, benzothienyl, thiazolyl, pyrazolyl, benzofuryl and benzothiazolyl groups;

phenyl(C$_1$–C$_4$)alkyl and naphthyl(C$_1$–C$_4$)alkyl groups; and the groups of formula:

in which n=1, 2 or 3 and B is chosen from —CH$_2$—, O or S and —NH—, the aryl or heteroaryl groups optionally being substituted with one or more groups chosen independently from halogens, C$_1$–C$_4$ alkyl, C$_3$–C$_7$ cycloalkyl, trifluoromethyl, C$_1$–C$_4$ alkylthio, C$_1$–C$_4$ alkyloxy, C$_1$–C$_4$ alkylsulfonyl, nitro, di((C$_1$–C$_4$)alkyl)amino and groups —COOR, —CH$_2$—COOR or —O—CH$_2$COOR, R being a C$_1$–C$_4$ alkyl group, phenyl and naphthyl groups and heteroaryl groups chosen from thienyl, furyl and pyridyl groups, iii) R$_3$ is chosen from a hydrogen atom, a C$_1$–C$_4$ alkyl group and a phenyl (C$_1$–C$_4$) alkyl group;

iv) A is chosen from groups —NH—CHR$_{10}$—, —NH—CHR$_{10}$—CH$_2$— and with p=1 or 2, R$_{10}$ being chosen from hydrogen, a C$_1$–C$_4$ alkyl group and a C$_6$–C$_{14}$ aryl group, v) and Z$_1$ and Z$_2$ are hydrogen or an amine-protecting group, and the addition salts thereof with pharmaceutically acceptable acids.

2. Compounds according to claim 1, of formula

Formula Ia in which:

i) either R$_1$ is chosen from:

C$_1$–C$_4$ alkyl, C$_3$–C$_{12}$ mono- or bicyclic cycloalkyl, C$_2$–C$_4$ alkenyl or C$_2$–C$_4$ alkynyl groups, these groups optionally being substituted with groups chosen from halogens and the hydroxyl group;

mono-, bi- or tricyclic C$_6$–C$_{14}$ aryl groups, heteroaryl groups chosen from pyridyl, thienyl, furyl, quinclyl, benzodioxanyl, benzodioxolyl, benzothienyl, benzofuryl and pyrazinyl groups;

phenyl(C$_1$–C$_4$)alkyl and naphthyl (C$_1$–C$_4$)alkyl groups optionally substituted on the aryl nucleus, the aryl and heteroaryl groups possibly being substituted with one or more groups chosen independently from halogens, $C_1$–$C_4$ alkyl, trifluoromethyl, $C_1$–$C_4$ alkylthio, $C_1$–$C_4$ alkylsulfonyl, $C_1$–$C_4$ alkyloxy, nitro and groups —COOR, —CH$_2$OOR or —OH$_2$—COOR, R being a $C_1$–$C_4$ alkyl group, the groups of formula:

$$-\underset{\underset{O}{\|}}{C}-NR_4R'_4$$

in which $R_4$ and $R'_4$ are chosen from $C_1$–$C_8$ alkyl and mono- or polycyclic $C_3$–$C_{12}$ cycloalkyl groups, these groups optionally being substituted with groups chosen from halogens and the hydroxyl group, $R'_4$ also possibly being hydrogen, or alternatively $R_4$ and $R'_4$ together form a tetramethylene or pentamethylene group, these last two groups themselves possibly being substituted, in particular with $C_6$–$C_{14}$ aryl or ($C_6$–$C_{14}$)aryl($C_1$–$C_4$) alkyl residue;

the groups of formula:

$$-\underset{\underset{O}{\|}}{C}-NH-(CH_2)_{\overline{m}}-R_5$$

in which m=1 to 4 and $R_5$ is chosen from phenyl, methoxyphenyl, indolyl, benzodioxolyl, benzodioxanyl, benzothienyl and benzofuryl groups, and $R_2$ is hydrogen, ii) or $R_1$ is hydrogen and $R_2$ is chosen from the groups of formula:

—NH—CO—$R_6$, $R_6$ being chosen from $C_1$–$C_4$ alkoxy, $C_3$–$C_7$ cycloalkoxy, benzyloxy, methoxyphenyl, dimethoxyphenyl, benzodioxolyl and benzodioxanyl groups, and the groups of formula:

—NH—SO$_2$—$R_7$, $R_7$ being chosen from:
$C_1$–$C_5$ alkyl groups optionally substituted with one or more groups chosen from halogens, hydroxyl groups and the trifluoromethyl group;
mono- or bicyclic $C_3$–$C_{12}$ cycloalkyl groups;
mono-, bi- or tricyclic $C_6$–$C_{14}$ aryl groups;
heteroaryl groups chosen from pyridyl, thienyl, quinolyl, benzodioxanyl, benzodioxolyl and isoxazolyl groups;
phenyl ($C_1$–$C_4$) alkyl and naphthyl ($C_1$–$C_4$) alkyl groups;
and the groups of formula:

$$-\underset{\underset{O}{\|}}{C}-NR_4R'_4$$

in which n=1, 2 or 3;
the aryl or heteroaryl groups optionally being substituted with one or more groups chosen independently from halogens, $C_1$–$C_4$ alkyl, triflucromethyl, $C_1$–$C_4$ alkylthio, $C_1$–$C_4$ alkyloxy, $C_1$–$C_4$ alkylsulfonyl, nitro, di(($C_1$–$C_4$)alkyl)amino and groups —COOR, —CH$_2$—COOR or —O—CH$_2$COOR, R being a $C_1$–$C_4$ alkyl group, iii) $R_3$ is chosen from a hydrogen atom, a $C_1$–$C_4$ alkyl group and a phenyl($C_1$–$C_4$)alkyl group, iv) and $Z_1$ and $Z_2$ are hydrogen or an amine-protecting group, and the addition salts thereof with pharmaceutically acceptable acids.

3. Compounds according to claim 1, in which $R_1$=H and $R_2$ is a group of formula

—NH—SO$_2$—$R_7$.

4. Compounds according to claim 3, in which $R_7$ is chosen from naphthyl, substituted naphthyl, phenylthienyl and biphenyl groups.

5. Compounds according to claim 1, in which $R_7$ is chosen from naphthyl, substituted naphthyl, phenylthienyl and biphenyl groups.

6. Compounds according to claim 1, which are: ethyl (2S)-2-[(2-naphthylsulfonyl)amino]-3-{[2-({4-(4-piperidyl)-2-[2-(4-piperidyl)ethyl]butanoyl}amino)acetyl]amino}propanoate; 3-(1,3-benzodioxol-5-yl)-3-{[2-({4-(4-piperidyl)-2-[2-(4-piperidyl)ethyl]butanoyl}amino)acetyl]amino}propanoic acid; 2-[(phenylsulfonyl)amino]-3-{[2-({4-(4-piperidyl)-2-[2-(4-piperidyl)ethyl]butanoyl}amino)acetyl]amino}propanoic acid; (2S)-2-[(2-naphthylsulfonyl)amino]-3-{[2-({4-(4-piperidyl)-2-[2-(4-piperidyl)ethyl]butanoyl}amino)acetyl]amino}propanoic acid; 2-[([1,1'biphenyl]-4-ylsulfonyl)amino]-3-{[2-({4-(4-piperidyl)-2-[2-(4-piperidyl)ethyl]butanoyl}amino)acetyl]amino}propanoic acid; 2-[(1-naphthylsulfonyl)amino]-3-{[2-({4-(4-piperidyl)-2-[2-(4-piperidyl)ethyl]butanoyl}amino)acetyl]amino}propanoic acid; 2-[(2-thienylsulfonyl)amino]-3-{[2-({4-(4-piperidyl)-2-[2-(4-piperidyl)ethyl]butanoyl}amino)acetyl]amino}propanoic acid; (2S)-2-{[(6-methoxy-2-naphthyl)sulfonyl]amino}-3-{[2-({4-(4-piperidyl)-2-[2-(4-piperidyl)ethyl]butanoyl}amino)acetyl]amino}propanoic acid; 2-[(mesitylsulfonyl)amino]-3-{[2-({4-(4-piperidyl)-2-[2-(4-piperidyl)ethyl]butanoyl}amino)acetyl]amino}propanoic acid; 2-{[(4-methylphenyl)sulfonyl]amino}-3-{[2-({4-(4-piperidyl)-2-[2-(4-piperidyl)ethyl]butanoyl}amino)acetyl]amino}propanoic acid; 2-({[3-(trifluoromethyl)phenyl]sulfonyl}amino)3-{[2-({4-(4-piperidyl)-2-[2-(4-piperidyl)ethyl]butanoyl}amino)acetyl]amino}propanoic acid; 2-{[(3-nitrophenyl)sulfonyl]amino}-3-{[2-({4-(4-piperidyl)-2-[2-(4-piperidyl)ethyl]butanoyl}amino)acetyl]amino}-propanoic acid; 2-{[(3,5-dimethyl-4-isoxazolyl)sulfonyl]amino}-3-{[2-({4-(4-piperidyl)-2-[2-(4-piperidyl)ethyl]butanoyl}amino)acetyl]amino}propanoic acid; 2-({[5-(dimethylamino)-1-naphthyl)sulfonyl}amino)-3-{[2-({4-(4-piperidyl)-2-[2-(4-piperidyl)ethyl]butanoyl}amino)acetyl]amino}propanoic acid; 2-{[(6,7-dimethoxy-2-naphthyl)sulfonyl]amino)-3-{[2-({4-(4-piperidyl)-2-[2-(4-piperidyl)ethyl]butanoyl}amino)acetyl]amino}propanoic acid; 2-[(3-pyridylsulfonyl)amino]3-{[2-({4-(4-piperidyl)-2-[2-(4-piperidyl)ethyl]butanoyl}amino)acetyl]amino}propanoic acid; 2-[(1,3-benzodioxol-5-ylsulfonyl)amino]-3-{[2-({4-(4-piperidyl)-2-[2-(4-piperidyl)ethyl]butanoyl}amino)acetyl]amino}propanoic acid; 2-[(2,3-dihydro-1,4-benzodioxin-6-ylsulfonyl)amino]-3-{[2-({4-(4-piperidyl)-2-[2-(4-piperidyl)ethyl]butanoyl}amino)acetyl]amino}propanoic acid; 2-[(1-benzothiophen-2-ylsulfonyl)amino]-3-{[2-({4-(4-piperidyl)-2-[2-(4-piperidyl)ethyl]

butanoyl}amino)acetyl]amino}propanoic acid; 2-{[(2,5-dimethyl-3-furyl)sulfonyl]amino}-3-{[2-({4-(4-piperidyl)-2-[2-(4-piperidyl)ethyl]butanoyl}amino)acetyl]amino}propanoic acid; 2-{[(4-fluoro-1-naphthyl)sulfonyl]amino}-3-{[2-({4-(4-piperidyl)-2-[2-(4-piperidyl)ethyl]butanoyl}amino)-acetyl]amino}propanoic acid; 2-{[(4-chloro-1-naphthyl)sulfonyl]-amino}-3-{[2-({4-(4-piperidyl)-2-[2-(4-piperidyl)ethyl]butanoyl}amino)acetyl]amino}propanoic acid; 2-[(1-benzofuran-2-ylsulfonyl)amino]-3-{[2-({4-(4-piperidyl)-2-[2-(4-piperidyl)ethyl]butanoyl}amino)acetyl]amino}propanoic acid; 2-[(2,3-dihydro-1H-inden-5-ylsulfonyl)amino]-3-{[2-({4-(4-piperidyl)-2-[2-(4-piperidyl)ethyl]butanoyl}amino)-acetyl]amino}propanoic acid; 2-{[(5-phenyl-2-thienyl))sulfonyl]-amino}-3-{[2-({4-(4-piperidyl)-2-[2-(4-piperidyl)ethyl]butanoyl}amino)acetyl]amino}propanoic acid; 2-[(5,6,7,8-tetrahydro-2-naphthalenylsulfonyl)amino]3-{[2-({4-(4-piperidyl)-2-[2-(4-piperidyl)ethyl]butanoyl}amino)acetyl]amino}propanoic acid; 2-[(2-naphthylsulfonyl)amino]-3-{[3-({4-(4-piperidyl)-2-[2-(4-piperidyl)ethyl]butanoyl}amino)propanoyl]amino}propanoic acid; (2R)-2-[(2-naphthylsulfonyl)amino]-3-{[2-({4-(4-piperidyl)-2-[2-(4-piperidyl)ethyl]butanoyl}amino)acetyl]amino}propanoic acid and the addition salts thereof with pharmaceutically acceptable acids.

7. A method of preparing compounds of formula (I) by a$_1$) reacting an acid of formula:

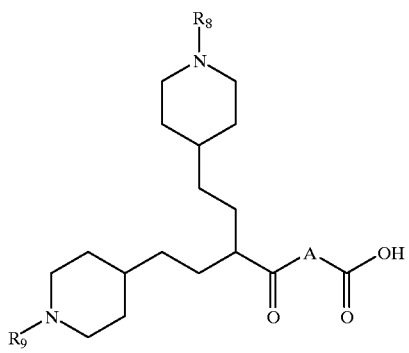

Formula II in which R$_8$ and R$_9$ are protecting groups, with an amine of formula

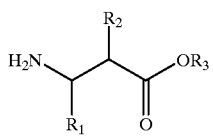

Formula III or a$_2$) reacting an acid of formula

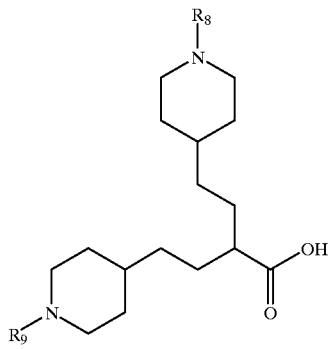

Formula IV in which R$_8$ and R$_9$ are protecting groups, with an amine of formula

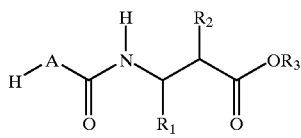

Formula V to give compounds of formula (Ib):

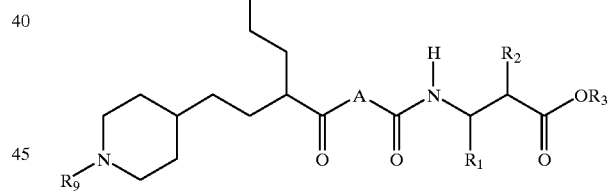

Formula Ib b) and, optionally, removing the protecting groups.

8. Antithrombotic composition which comprises, an effective amount of a compound as defined in claim 1.

9. A method of inhibiting the binding of fibrinogen to the blood platelets of a mammal, comprising the administration to this mammal of an effective amount of a compound according to claim 1.

10. A method of inhibiting the aggregation of the blood platelets of a patient, comprising the administration to this patient of an effective amount of a compound according to claim 1.

11. A method of treating a thrombosis in a patient, comprising the administration to this patient of an effective amount of a compound according to claim 1.

12. A method of preventing thrombotic risk in a patient, comprising the administration to this patient of an effective amount of a compound according to claim 1.

13. Compounds of formula:
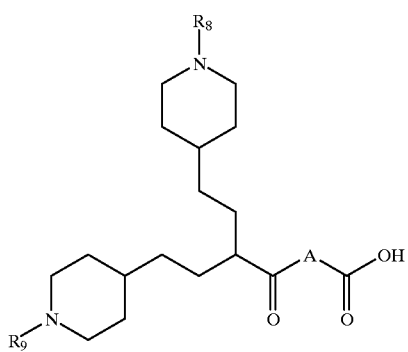
Formula II
in which $R_8$ and $R_9$ are protecting groups and A has the meaning given in claim 1.
14. Compounds of formula:
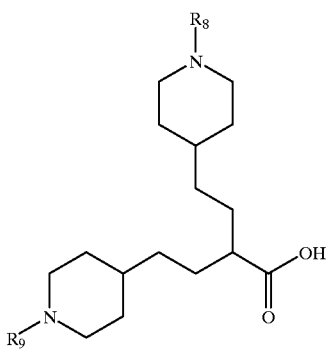
Formula IV
in which $R_8$ and $R_9$ are protecting groups.
* * * * *